(12) United States Patent
Zahn et al.

(10) Patent No.: US 8,501,787 B2
(45) Date of Patent: Aug. 6, 2013

(54) COMPOUNDS FOR THE INHIBITION OF ANGIOGENESIS AND USE THEREOF

(75) Inventors: Grit Zahn, Berlin (DE); Roland Stragies, Berlin (DE); Frank Osterkamp, Berlin (DE); Gunther Zischinsky, Berlin (DE); Jochen Knolle, Berlin (DE); Gerd Hummel, Berlin (DE); Sascha Birkner, Essen (DE); Ulrich Reineke, Berlin (DE)

(73) Assignee: Shire Orphan Therapies GmbH, Berlin (DE)

( * ) Notice: Subject to any disclaimer, the term of this patent is extended or adjusted under 35 U.S.C. 154(b) by 1595 days.

(21) Appl. No.: 10/593,801

(22) PCT Filed: Mar. 24, 2005

(86) PCT No.: PCT/EP2005/003163
§ 371 (c)(1),
(2), (4) Date: Sep. 21, 2006

(87) PCT Pub. No.: WO2005/090329
PCT Pub. Date: Sep. 29, 2005

(65) Prior Publication Data
US 2007/0155712 A1 Jul. 5, 2007

(30) Foreign Application Priority Data
Mar. 24, 2004 (EP) .................................. 04007067

(51) Int. Cl.
A61K 31/4439 (2006.01)
C07D 401/12 (2006.01)

(52) U.S. Cl.
USPC ................... 514/343; 546/278.4; 546/278.7

(58) Field of Classification Search
USPC ................... 546/278.4, 278.7; 514/343
See application file for complete search history.

(56) References Cited

U.S. PATENT DOCUMENTS

| | | | |
|---|---|---|---|
| 5,399,570 A | 3/1995 | Klingler et al. | |
| 5,936,065 A | 8/1999 | Arrhenius et al. | |
| 6,069,254 A | 5/2000 | Costanzo et al. | |
| 6,685,617 B1 | 2/2004 | Blinn et al. | |
| 2003/0171304 A1 | 9/2003 | Hoelzeman et al. | |
| 2004/0110945 A1 | 6/2004 | Nakayama et al. | |

FOREIGN PATENT DOCUMENTS

| | | |
|---|---|---|
| EP | 1 346 982 A | 9/2003 |
| JP | 7109256 | 4/1995 |
| WO | WO 97/41102 | 11/1997 |
| WO | WO 99/37621 A | 7/1999 |
| WO | WO 99/67230 | 12/1999 |

OTHER PUBLICATIONS

Vippagunta et al., "Crystalline Solids", Advanced Drug Delivery Reviews 48 (2001) 3-26.*
Guillory (in Brittain ed.), "Polymorphism, etc.," NY: Marcel Dekker, Inc., 1999, 1-2, 183-226.*
Miller et al., "Identification and in vivo efficacy of small-molecule antagonists of integrin alphavbeta3 (the vitronectin receptor)", Drug Discovery Today, vol. 5, No. 9, Sep. 2000, pp. 397-408.
Austrian Search Report for Singapore Application No. 200901998-5, dated Sep. 26, 2011.

* cited by examiner

*Primary Examiner* — Patricia L Morris
(74) *Attorney, Agent, or Firm* — Morse, Barnes-Brown & Pendleton, P.C.; Lisa M. Treannie, Esq.

(57) ABSTRACT

This invention is directed to compounds of structure (I). Particularly this invention is directed to compounds of structure (VIII) wherein the variables are defined as in the description. These compounds are integrin inhibitors and are useful in the treatment of diseases in which an inhibition of angiogenesis is desired.

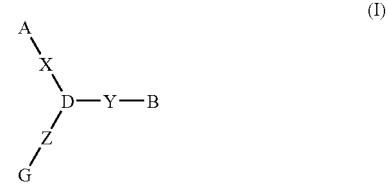

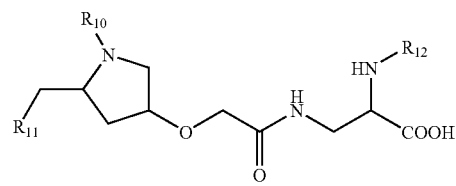

23 Claims, 7 Drawing Sheets

COMPOUNDS FOR THE INHIBITION OF ANGIOGENESIS AND USE THEREOF

CROSS REFERENCE TO RELATED APPLICATION

This application is a 35 USC §371 National Phase Entry Application from PCT/EP2005/003163, filed Mar. 24, 2005, and designating the United States.

The present invention is related to new compounds and the use of said compounds for the manufacture of medicaments and diagnostics.

Angiogenesis, also called neovascularization, is a fundamental process whereby new blood vessels are formed. Under normal physiological conditions angiogenesis is highly regulated and essential for reproduction, embryonic development and wound healing (Folkman and Shing, 1992, JBC, 267, 10931). However angiogenesis also occurs under various pathological conditions, including ocular neovascularization such as in diabetic retinopathy, age related macular degeneration and various other eye diseases, inflammatory disorders like rheumatoid arthritis and tumor growth and metastasis (Folkman and Shing, 1992, JBC, 267, 10931).

During neovascular disorders in cancer newly formed blood vessels provide the tumor cells with oxygen and nutrients which are necessary for further growth above 1-2 $mm^3$ and form a gateway for tumor cells to enter the circulation and to metastasize to distant sites of the body (Folkman and Shing, 1992, JBC, 267, 10931).

During ocular neovascular disorders the pathological growth of new blood vessels cause the loss of vision. The leading cause of blindness in individuals over the age of 65 is the age related macular degeneration (AMD), characterized by the growth of new blood vessels from the choroid, which remain beneath the retinal pigment epithelium (RPE), or breach the RPE and enter the subretinal space, leading to hemorrhage, detachment of RPE and formation of subretinal scars followed by blindness (Ambati, 2003, Survey of Ophthalmology, 48, 257). The leading cause of blindness in individuals under the age of 55 years is proliferative diabetic retinopathy (PDR), whereby retinal blood vessels proliferate along the surface of the retina and into the posterior vitreous due to ischaemic stimuli (Klein, 1994, Arch Ophthalmol. 112, Friedlander, 1996, PNAS, 93, 9764).

Angiogenesis is also associated with inflammatory diseases, including rheumatoid arthritis, psoriasis, osteoarthritis, inflammatory bowel disease, Crohn's disease, ulcerative colitis and others. The influx of lymphocytes into the inflammatory region stimulates angiogenesis and following this, the increased vasculature enables a greater influx of leukocytes, which promote the inflammatory process, such as destruction of cartilage and bone in the joint during arthritis. Angiogenesis is a highly regulated process which occurs in response to various proangiogenic stimuli like growth factors, cytokines and other physiological molecules as well as other factors like hypoxia and low pH (Folkman and Shing, 1992, JBC, 267, 10931). The angiogenic cascade for development of new blood vessels requires the cooperation of a variety of molecules that regulate necessary cellular processes such as extracellular matrix (ECM) remodelling, invasion, migration, proliferation, differentiation and tube formation (Brooks, 1996, Eur. J. Cancer, 32A, 2423). After an initiation phase proangiogenic molecules like VEGF, bFGF, PDGF and others activate endothelial cells via stimulation of their cell surface receptors (for example VEGFR1-Flt-1 and VEGFR2-Flk1/KDR). These activated cells undergo a process of cellular proliferation, elevated expression of cell adhesion molecules, increased secretion of proteolytic enzymes and increased cellular migration and invasion. A number of distinct molecules are involved to promote proliferation and invasion, including members of the integrin, selectin and immunoglobulin gene super family for adhesion as well as proteolytic enzymes such as matrix metalloproteinases and serine proteinases for degrading the ECM (Brooks, 1996, Eur. J. Cancer, 32A, 2423). Finally, a complex cascade of biochemical signals derived from cell surface receptors interacting with ECM components and soluble factors, leading to lumen formation and differentiation into mature blood vessels.

Inhibition of different molecules involved in the angiogenic cascade has been shown to be active in inhibition of angiogenesis and treatment of neovascular diseases in animal models and clinical studies (Madhusudan, 2002, Curr. Op. Pharm., 2, 403; Folkman, 2001, Thromb Haemost, 86, 23; Eyetech Study Group, 2003, Ophthalmology, 110, 979; Ferrara, 2002, Semin Oncol. 6 Suppl 16, 10) for cancer and age related macular degeneration (AMD). Most of these angiogenic inhibitors are directed towards blocking the initial growth factor mediated activation step induced by VEGF or PDGF. These approaches target only one molecule of the multiple set of pro-angiogenic stimuli. However, angiogenesis takes place in response to various growth factors such as VEGF, bFGF, PDGF and others (Folkman and Shing, 1992, JBC, 267, 10931). Therefore, a more general approach for inhibiting angiogenesis due to this variety of stimuli would be more beneficial.

Inhibition of cell adhesion to the ECM, the fundamental step for activation, survival, targeting and migration of activated endothelial cells (EC), is the most promising target mechanism for anti-angiogenesis. Most of these interactions are mediated by integrins, a family of multifunctional cell adhesion receptors.

Members of the integrin family are non-covalently associated alpha/beta heterodimers that mediate cell-cell, cell-extracellular matrix and cell-pathogene interactions. These type I transmembrane proteins are expressed on a variety of cells and require bivalent cations for their physiological function. Until now, 19 different integrin alpha subunits and 8 different beta subunits are known that combine to form at least 25 different alpha/beta heterodimers with different ligand specificity. The ligands for the extracellular domain of many integrins are the proteins of the extracellular matrix, whereby mostly a consensus motif with the amino acid sequence RGD (arginine-glycine-aspartate) is recognized. The intracellular domains of the integrins are either directly or indirectly connected to intracellular components such as kinases and the cytoskeleton. Integrins serve as bidirectional signalling receptors, whereby protein activities and gene expression are changed by integrins in response to ligand binding to the extracellular domain thereof, which is also referred to as outside-in signalling. On the other hand, the affinity of the integrins is modulated in response to intracellular changes such as binding of proteins to the intracellular domain of the integrin, which is referred to as inside-out signalling (Humphries, 2000, Biochem. Soc. Trans., 28, 311; Hynes, 2002, Cell 110, 673).

A multitude of studies on the integrin pattern on activated endothelial cells, mice gene knockouts and inhibition studies in angiogenic animal models with antibodies, peptides and small molecules provided information about the integrins and ECM proteins involved in critical steps of angiogenesis (Brooks, 1994, Science, 264, 569; Brooks, 1996, Eur. J. Cancer, 32A, 2423; Mousa, 2002, Curr. Opin. Chem Biol, 6, 534; Hynes, 2002, Cell, 110, 673; Hynes, 2002, Nature Medicine, 8, 918; Kim, 2000, Am. J. Path., 156, 1345). Thereby it becomes clear that above all the vitronectin receptors alphav-beta3, alphavbeta5 and the fibronectin receptor alpha5beta1 play a critical role in angiogenesis. Gene deletion studies of integrins attributed essential roles for almost all integrins. The deletion driven defects suggest widespread contributions of the various integrins to both the maintenance of tissue integrity and the promotion of cellular migration. But only the deletion of alpha5 and beta1 and its ligand fibronectin, leads to embryogenic lethality with major vascular effects, whereas ablation of alphav, beta3 and beta5 genes fail to block angiogenesis and in some cases even enhance angiogenesis (Hynes, 2002, Nature Medicine, 8, 918).

Additionally, experimental studies established a fundamental role of alpha5beta1 in the regulation of alphavbeta3 mediated angiogenesis (Kim, 2000, JBC, 275, 33920).

Only alpha5beta1 genetic and pharmacological data are consistent and confirm the fundamental role of alpha5beta1 for angiogenesis. Therefore, alpha5beta1 should be the preferred target for the development of anti-angiogenic drugs. Consequently, antagonists of integrin alpha5beta1 have a great therapeutic potential for the treatment of neovascularization in tumors, in the eye and of inflammatory processes.

Several other diseases also involve integrin mediated effects and processes, such as in atherosclerosis progression and restenosis. Particularly, angiogenesis and migration are the critical features of plaque development during atherosclerosis (Hoshiga, 1995, Circ. Res. 77, 1129) and undesired vascular repair processes in vessels of atherosclerotic patients cause coronary restenosis (Panda, 1997, PNAS, 94, 9308). An integrin mediated eye disease is proliferative vitreoretinopathy with pathological proliferation of retinal pigment epithelium cells (Proulx, 2003, Molecular Vision, 9, 473).

There is a lot of evidence suggesting a central role for alpha5beta1 in angiogenesis, e.g. mice knockout data. Thus, genetic ablation of either of the monomers of alpha5beta1 leads to embryonic lethality with major vascular defects (Hynes, 2002, Nature Medicine, 8, 918). Additionally, alpha5beta1 is poorly expressed in quiescent endothelium but strongly expressed in proliferating endothelium. Its expression is significantly upregulated on blood vessels in human tumors and after stimulation with growth factors (Kim, 2000, Am. J. Path, 156, 1345; Collo, 1999, J. Cell Sc., 112, 569). Once expressed, alpha5beta1 regulates the survival and migration of endothelial cells in vitro and in vivo (Kim, 2002, J. Clin. Invest., 110, 933; Kim, 2000, JBC, 275, 33920). Angiogenesis induced by multiple growth factors in several models was blocked with alpha5beta1 antagonists (Varner, 1998, 98 (suppI), I-795, 4166; Kim, 2000, Am. J. Path, 156, 1345). Additionally, these antagonists also inhibit tumor angiogenesis, thereby causing regression of human tumors in animal models (Kim, 2000, Am. J. Path, 156, 1345).

Given the importance of integrins in angiogenesis, serious efforts have been undertaken to develop inhibitors thereto.

There are at least three major classes of reagents developed as integrin, especially alpha5beta1 integrin antagonists. These include antibodies such as monoclonal antibodies, polyclonal antibodies, and antibody fragments (Kim, 2000, Am. J. Path., 156, 1345), natural peptides such as venom derived "disintegrin" peptides (Marcinkiewicz, 1999, Biochemistry, 38, 13302), synthetic peptides (Koivunen, 1994, JBC, 124, 373) and non-peptidic small molecules such as spiro compounds (WO97/33887).

Although these compounds are in principle suitable as alpha5beta1 antagonists, they have some drawbacks. For example, antibodies are complex biological molecules with usually high activity and specificity for the targeted molecule. But the mainly non-human source of antibodies could cause an immune response during later treatment of humans or the molecules have to be humanized with special additional procedures. Additionally, the human immune system could develop antibodies against the antigen binding region of the therapeutic antibody (anti-idiotypic antibodies). The development of an immune response against the therapeutic antibody could cause immunological problems in humans and decreases the effectivity of the antibody. Also the production of antibodies requires special treatment so as to avoid any contaminants such as prions or other proteinaceous material, which might have a detrimental effect upon application to a patient. Additionally, the high molecular weight of these molecules constrict the possible administration routes of the medicament during treatment of patients, usually to intra venous route.

There are several peptidic alpha5beta1 inhibitors known that are based on the natural ligand derived RGD-sequence, but these inhibitors show mostly no or only limited specificity against other integrins. Furthermore, peptidic molecules are generally disadvantageous concerning their application as a medicament. One aspect thereof resides in the limited stability against naturally occurring proteases. Another one is the limitation of possible administration routes.

One fibronectin derived peptide (U.S. Pat. No. 6,001,965) proposed to act via alpha5beta1 showed anti-metastatic activity in mouse tumor models (Stoeltzing, 2003, Int. J. Cancer 104, 496) and inhibition of cell invasion (Livant, 2000, Cancer Res., 60, 309), but no direct inhibition of alpha5beta1-fibronectin interaction could be shown. It only binds to alpha5beta1 (without effecting the fibronectin binding) and alphavbeta3 integrin (conference talk at $6^{th}$ international symposium on anti-angiogenic agents, San Diego, 30 Jan.-1 Feb. 2004). Therefore, the molecular mechanism of action and the specificity remain unclear and shed some further doubt on the usage of fibronectin, non-RGD sequence derived peptides as inhibitors to alpha5beta1 (so called synergistic sequence).

The small molecules synthesized in the art are e.g. described in the international patent application WO 97/33887 which discloses compounds comprising a spiro moiety as a core element. However, due to the spiro moiety contained in these compounds they are rather rigid in their structure and difficult to synthesize. In contrast thereto, international patent application WO 95/32710 discloses the use of a benzyl residue as a core element. These compounds, however, seem to lack the required specificity for an integrin particularly relevant in the pathomechanism of the aforementioned diseases.

The problem underlying the present invention is thus to provide chemical compounds which are suitable to interact with integrins, more particularly specifically interact with certain integrin species such as integrin alpha5beta1. A further problem underlying the present invention is to provide antagonists for alpha5beta1, which preferably show enhanced activity, stability, selectivity, and synthetic accessibility. A further problem underlying the present invention is to provide new modes of treatment for diseases, preferably for diseases involving integrin mediated effects and processes.

In a first aspect the problem underlying the present invention is solved by a compound of the formula (I)

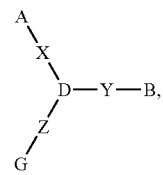

wherein
D is a radical selected from the group comprising heterocyclic and homocyclic rings, X is a radical selected from the group comprising, C=O, SO$_2$, NH—(C=O), (C=O)—NH, C=S, CH$_2$, O—(C=O), (C=O)—O, (C=S)—NH, NH—(C=S), NR$^a$—(C=O), (C=O)—NR$^a$, (C=S)—NR$^a$ and NR$^a$—(C=S), Y is a radical selected from the group comprising —(CH$_2$)$_n$-E-(CH$_2$)$_m$-L-(CH$_2$)$_k$ and —(CH$_2$)$_m$-L-(CH$_2$)$_k$,
  wherein E is a radical selected from the group comprising O, S and NR$^b$,
k, m and n are individually and independently 0, 1, 2 and 3,
Z is a radical selected from the group comprising C=O, and alkyl, whereby preferably alkyl is CH$_2$ or CH$_2$CH$_2$,
A is a radical selected from the group comprising benzyl, substituted benzyl, phenyl, substituted phenyl, alkyl and substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl,
B is a radical having formula (II)

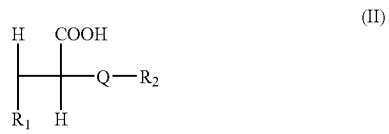

wherein
  R$_1$ is selected from the group comprising H, benzyl, substituted benzyl, phenyl, substituted phenyl, alkyl and substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl,
  R$_2$ is selected from the group comprising H, benzyl, substituted benzyl, phenyl, substituted phenyl, alkyl and substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl,
G is a radical comprising at least one nitrogen atom, and
  wherein Q and L are each and independently from each other a radical selected from the group comprising (C=O)—NH, C=O, C=S, NH, O, S, CH$_2$, NH—NH, N=N, CH—N, N=CH, NH—(C=O)—NH, NH—(C=O), O—(C=O)—NH, NH—(C=O)—O, (C=O)—O, O—(C=O), NH—(C=S), (C=S)—NH, NH—(C=S)—NH, SO$_2$, NH—SO$_2$, SO$_2$—NH, NR$^c$, (C=O)—NR$^c$, NR$^c$, NR$^c$—(C=O)—NH, NH—(C=O)—NR$^c$, NR$^c$—(C=O)—NR$^d$, NR$^c$—(C=O), O—(C=O)—NR$^c$, NR$^c$—(C=O)—O, NR$^c$—(C=S), (C=S)—NR$^c$, NR$^c$—(C=S)—NH, NH—(C=S)—NR$^c$, NR$^c$—(C=S)—NR$^d$, NR$^c$—SO$_2$ and SO$_2$—NR$^c$, and
  wherein any of R$^a$, R$^b$, R$^c$ and R$^d$ is each and independently a radical selected from the group comprising H, alkyl, substituted alkyl, cycloalkyl, substituted cycloalkyl, heterocycloyl, substituted heterocycloyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-alkyl, substituted alkyloxy-alkyl, alkyloxy-cycloalkyl, substituted alkyloxy-cycloalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, alkylthio-alkyl, substituted alkylthio-alkyl, alkylthio-cycloalkyl and substituted alkylthio-cycloalkyl.

In an embodiment the ring in D is an aromatic or a non-aromatic ring.

In an embodiment the ring in D is selected from the group comprising five-membered rings, six-membered rings, seven-membered rings, eight-membered rings, nine-membered rings and ten-membered rings or the ring in D is a condensed ring system selected from the group comprising four-four-membered rings, four-five-membered rings, five-five-membered rings, five-six-membered rings, six six-membered rings, six-seven-membered rings, seven-seven-membered rings.

In an embodiment the ring in D is a heterocyclic ring comprising at least one nitrogen atom.

In a preferred embodiment any of X, Y, Z is attached to the nitrogen atom.

In an embodiment the compound is of the formulae (III a, III b)

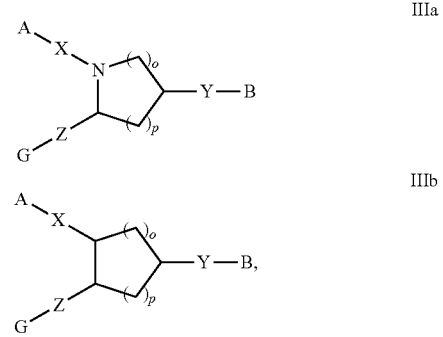

wherein o and p are independently and individually 0, 1, 2 or 3.

In an embodiment D is selected from the group comprising pyrrole, pyrrolidine, indole, pyridine, piperidine, quinoline, isoquinoline, imidazole, pyrimidine, purine, pyridazine piperazine, 1,3,5-triazine, 1,2,3-triazole, imidazolidine, and pyrazole and any derivatives of each thereof.

In an embodiment D is a radical selected from the group comprising thiophene, thiazole, isothiazole, 1,4 dithiane, 1,3,5 trithiane, and thiomorpholine.

In an embodiment D is a radical selected from the group comprising furane, dioxane, pyrane and derivatives of each thereof.

In an embodiment D is a radical selected from the group comprising oxazole, isoxazole, and thiazole and derivatives of each thereof.

In an embodiment
n is 0, E is O, m is 1, L is (C=O)—NH and k is 0; or
n is 1, E is O, m is 1, L is (C=O)—NH and k is 0; or
n is 0, E is O, m is 2, L is (C=O)—NH and k is 0; or
n is 0, E is $CH_2$, m is 1, L is (C=O)—NH and k is 0; or
n is 1, E is O, m is 2, L is (C=O)—NH and k is 0.

In an embodiment Z is $CH_2$.

In an embodiment A is selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl and substituted alkylthio-cycloalkyl.

In an embodiment A is selected from the group comprising benzyl, substituted benzyl, phenyl, substituted phenyl, heterocyclyl, substituted heterocyclyl, aryl, substituted aryl, heterocyclyl, substituted heterocyclyl, arylalkyl substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, arylthio-alkyl, substituted arylthio-alkyl, arylthio-cycloalkyl and substituted arylthio-cycloalkyl.

In an embodiment A is a phenyl derivative or a benzyl derivative having the formula (IV) or (V)

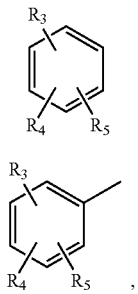

wherein $R_3$, $R_4$, and $R_5$ is each and independently a radical selected from the group comprising H, halogen, alkyl, substituted alkyl, alkoxy and substituted alkoxy.

In a preferred embodiment alkyl is selected from the group comprising methyl, ethyl, propyl, butyl, pentyl, hexyl, whereby any of the residues is straight, branched, branched-linear or branched non-linear.

In a further preferred embodiment alkoxy is selected from the group comprising methoxy, ethoxy, propoxy, butoxy, pentoxy, hexoxy.

In an alternate embodiment the substituted alkyl is an alkyl having at least one halogen, $NO_2$, OH, CN residue.

In a preferred embodiment the substituted alkyl is selected from the group comprising $CF_3$ and $CCl_3$.

In an embodiment A is a linear alkyl or non-linear alkyl, preferable A is 2,2-dimethyl-butyl.

In an embodiment the halogen is independently selected from the group comprising I, Br, Cl and F.

In an embodiment $R_2$ is selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl and substituted alkylthio-cycloalkyl, more preferably selected from the group comprising cycloalkyl and substituted cycloalkyl, and more preferably $R_2$ is

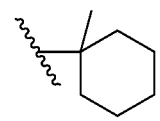

In an alternate embodiment $R_2$ is selected from the group comprising benzyl, substituted benzyl, phenyl, substituted phenyl, heterocyclyl, substituted heterocyclyl, aryl, substituted aryl, heterocyclyl, substituted heterocyclyl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, arylthio-alkyl, substituted arylthio-alkyl, arylthio-cycloalkyl and substituted arylthio-cycloalkyl.

In an embodiment $R_2$ is a radical having the following formula (VI)

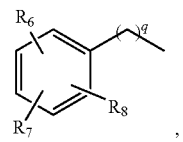

wherein q is 0, 1, 2, 3, or 4,
$R_6$, $R_7$ and $R_8$ are each individually and independently selected from the group of radicals comprising halogen, alkyl, substituted alkyl, alkoxy and substituted alkoxy.

In a preferred embodiment alkyl and/or the substituted alkyl is selected from the group comprising methyl, ethyl, propyl, butyl, pentyl, hexyl, whereby any of the residues is straight, branched, branched-linear or branched non-linear.

In a further preferred embodiment alkoxy is selected from the group comprising methoxy, ethoxy, propoxy, butoxy, pentoxy, hexoxy.

In a still further preferred embodiment the substituted alkyl is an alkyl having at least one halogen $NO_2$, OH, CN residue.

In a more preferred embodiment the substituted alkyl is selected from the group comprising $CF_3$ and $CCl_3$.

In an alternate preferred embodiment $R_2$ is mesitylene.

In an embodiment Q of B is C=O.
In an alternate embodiment Q of B is $SO_2$.
In an embodiment G is a radical of formula (VII).

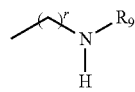

wherein $R_9$ is a heterocyclic ring and r is 0, 1, 2, 3 or 4.

In a preferred embodiment $R_7$ is a three-membered, four-membered, five-membered, six-membered, seven-membered, eight-membered, nine-membered or ten-membered ring, preferably having at least one nitrogen atom in the ring.

In an alternate preferred embodiment $R_7$ is a condensed ring, preferably having at least one nitrogen atom.

It is within the present invention that any of the aforementioned rings, preferably those of the three last mentioned embodiments, can comprise one or more substituents thus creating derivatives of the respective rings. Such derivatives comprise, but are not limited to the alkl derivatives, alkoxy derivatives, thioalkyl derivatives and halogen derivatives. In other words, the respective rings are in further embodiments alkyl substituted rings, alkoxy substituted rings, thioalkyl substituted rings and halogen substituted rings.

In an embodiment G is a guanidine radical.

In an embodiment G is (C=O)—NH$_2$ or NH—(C=O)—NH$_2$.

In an embodiment G is selected from the group comprising pyridin-2-ylamine, pyrimidin-2-ylamine, 1(2)H-imidazol-2-ylamine, 4,5-dihydro-1H-imidazol-2-ylamine, 1,4,5,6-tetrahydro-pyrimidin-2-ylamine, 4,5,6,7-tetrahydro-1H-[1,3]diazepin-2-ylamine, 1,4,5,6,7,8-hexahydro-[1,3]diazocine, 1,4,5,6,7,8,9,10-octahydro-[1,3]diazecin-2-ylamine, 4,5-dihydro-3H-pyrrol-2-ylamine, 3,4,5,6-tetrahydro-pyridin-2-ylamine, 4,5,6,7-tetrahydro-3H-azepin-2-ylamine, 3,4,5,6,7,8-hexahydro-azocin-2-ylamine, 3,4,5,6,7,8,9,10-octahydro-azecin-2-ylamine, 1H-benzoimidazol-2-ylamine, 2(3)H-pyrazol-3-ylamine, 1H-indol-2-ylamine, 1,2,3,4-tetrahydro-[1,8]naphthyridine, pyrazin-2-ylamine and any derivative of each thereof, whereby preferably such derivative is selected from the group comprising the alky derivative, the alkoxy derivative, the thioalkyl derivative and the halogen derivative.

In an embodiment G is selected from the group comprising pyridin-2-ylamine, 4-methoxy-pyridin-2-ylamine, 1(2)H-imidazol-2-ylamine, 2(3)H-pyrazol-3-ylamine.

In a second aspect the problem underlying the present invention is solved by a compound having the formula (VIII)

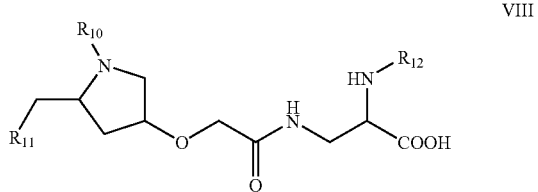

VIII wherein $R_{10}$ is —CO—$R_{13}$ or —CO—O—$R_{13}$,
wherein $R_{11}$ is a substituted pyridine-2-ylamine,
wherein $R_{12}$ is —CO—$R_{13}$, —SO$_2$—$R_{13}$, and
wherein $R_{13}$ is a radical selected from the group comprising alkyl, substituted alkyl, cycloalkyl, aryl, substituted aryl, heteroaryl, substituted heteroaryl,
whereby the compound is preferably a compound according to the first aspect of the present invention.

In an embodiment of the second aspect the compound has the formula (IX)

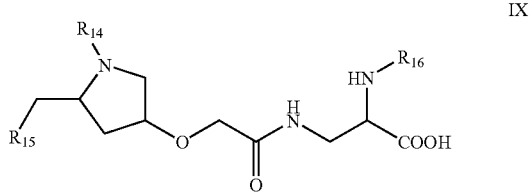

IX wherein $R_{14}$ is 3,3-dimethyl-butyryl or 3-carboxy-phenyl,
wherein $R_{15}$ is pyridin-2-ylamine, 4-methoxy-pyridin-2-ylamine, wherein $R_{16}$ is —CO—$R_{17}$, and
wherein $R_{17}$ is mesitylene or 1-methyl cyclohexyl, In a third aspect the problem underlying the present invention is solved by a compound selected from the group comprising
compound 5: [2-Carboxy-2-(2,4,6-trimethyl-benzenesulfonylamino)-ethylcarbamoyl]-methoxy-2-(pyridin-2-ylaminomethyl)-pyrrolidine-1-carboxylic acid benzyl ester
compound 9: 2-[1-Phenylacetyl-5-(pyridin-2-ylaminomethyl)-pyrrolidin-3-yloxy]-acetylamino-2-(2,4,6-trimethyl-benzenesulfonylamino)-propionic acid
compound 10: (2-Benzenesulfonylamino-2-carboxy-ethylcarbamoyl)-methoxy-2-(pyridin-2-ylaminomethyl)-pyrrolidine-1-carboxylic acid benzyl ester)
compound 13: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid butyl ester
compound 14: 3-{2-[1-(3-Phenyl-propionyl)-5-(pyridin-2-ylaminomethyl)-pyrrolidin-3-yloxy]-acetylamino}-2-(2,4,6-trimethyl-benzenesulfonylamino)-propionic acid
compound 15: 3-{2-[1-Phenylmethanesulfonyl-5-(pyridin-2-ylaminomethyl)-pyrrolidin-3-yloxy]-acetylamino}-2-(2,4,6-trimethyl-benzenesulfonylamino)-propionic acid
compound 16: 3-{2-[1-(Butane-1-sulfonyl)-5-(pyridin-2-ylaminomethyl)-pyrrolidin-3-yloxy]-acetylamino}-2-(2,4,6-trimethyl-benzenesulfonylamino)-propionic acid
compound 17: 3-{2-[1-Methyl-5-(pyridin-2-ylaminomethyl)-pyrrolidin-3-yloxy]-acetylamino}-2-(2,4,6-trimethyl-benzenesulfonylamino)-propionic acid
compound 18: 3-{2-[1-(3-Phenyl-propyl)-5-(pyridin-2-ylaminomethyl)-pyrrolidin-3-yloxy]-acetylamino}-2-(2,4,6-trimethyl-benzenesulfonylamino)-propionic acid
compound 19: 3-{2-[5-(Pyridin-2-ylaminomethyl)-pyrrolidin-3-yloxy]-acetylamino}-2-(2,4,6-trimethyl-benzenesulfonylamino)-propionic acid
compound 20: 3-{2-[1-Cyclopentylcarbamoyl-5-(pyridin-2-ylaminomethyl)-pyrrolidin-3-yloxy]-acetylamino}-2-(2,4,6-trimethyl-benzenesulfonylamino)-propionic acid
compound 21: 3-{2-[1-Cyclohexylcarbamoyl-5-(pyridin-2-ylaminomethyl)-pyrrolidin-3-yloxy]-acetylamino}-2-(2,4,6-trimethyl-benzenesulfonylamino)-propionic acid
compound 22: 3-{2-[1-Butylcarbamoyl-5-(pyridin-2-ylaminomethyl)-pyrrolidin-3-yloxy]-acetylamino}-2-(2,4,6-trimethyl-benzenesulfonylamino)-propionic acid
compound 23: 3-{2-[1-Pentylcarbamoyl-5-(pyridin-2-ylaminomethyl)-pyrrolidin-3-yloxy]-acetylamino}-2-(2,4,6-trimethyl-benzenesulfonylamino)-propionic acid
compound 24: 3-{2-[1-(2-Fluoro-benzylcarbamoyl)-5-(pyridin-2-ylaminomethyl)-pyrrolidin-3-yloxy]-acetylamino}-2-(2,4,6-trimethyl-benzenesulfonylamino)-propionic acid
compound 25: 3-{2-[1-(4-Methyl-benzylcarbamoyl)-5-(pyridin-2-ylaminomethyl)-pyrrolidin-3-yloxy]-acetylamino}-2-(2,4,6-trimethyl-benzenesulfonylamino)-propionic acid
compound 26: 3-{2-[1-Phenethylcarbamoyl-5-(pyridin-2-ylaminomethyl)-pyrrolidin-3-yloxy]-acetylamino}-2-(2,4,6-trimethyl-benzenesulfonylamino)-propionic acid
compound 27: 3-{2-[1-(3-Methyl-benzylcarbamoyl)-5-(pyridin-2-ylaminomethyl)-pyrrolidin-3-yloxy]-acetylamino}-2-(2,4,6-trimethyl-benzenesulfonylamino)-propionic acid
compound 28: 3-{2-[1-Phenylcarbamoyl-5-(pyridin-2-ylaminomethyl)-pyrrolidin-3-yloxy]-acetylamino}-2-(2,4,6-trimethyl-benzenesulfonylamino)-propionic acid
compound 29: 3-{2-[1-(2-Methyl-pentanoyl)-5-(pyridin-2-ylaminomethyl)-pyrrolidin-3-yloxy]-acetylamino}-2-(2,4,6-trimethyl-benzenesulfonylamino)-propionic acid compound 30: 3-{2-[1-(3-Cyclopentyl-propionyl)-5-(pyridin-2-ylaminomethyl)-pyrrolidin-3-yloxy]-acetylamino}-2-(2,4,6-trimethyl-benzenesulfonylamino)-propionic acid compound 31: 3-{2-[1-(3,3-Dimethyl-butyryl)-5-(pyridin-2-ylaminomethyl)-pyrrolidin-3-yloxy]-acetylamino}-2-(2,4,6-trimethyl-benzenesulfonylamino)-propionic acid compound 32: 3-{2-[1-Cyclohexanecarbonyl-5-(pyridin-2-ylaminomethyl)-pyrrolidin-3-yloxy]-acetylamino}-2-(2,4,6-trimethyl-benzenesulfonylamino)-propionic acid compound 33: 3-{2-[5-(Pyridin-2-ylaminomethyl)-1-(3,5,5-trimethyl-hexanoyl)-pyrrolidin-3-yloxy]-acetylamino}-2-(2,4,6-trimethyl-benzenesulfonylamino)-propionic acid compound 34: 3-{2-[5-(Pyridin-2-ylaminomethyl)-1-(2-thiophen-2-yl-acetyl)-pyrrolidin-3-yloxy]-acetylamino}-2-(2,4,6-trimethyl-benzenesulfonylamino)-propionic acid compound 35: 3-{2-[1-(2-Cyclopentyl-acetyl)-5-(pyridin-2-ylaminomethyl)-pyrrolidin-3-yloxy]-acetylamino}-2-(2,4,6-trimethyl-benzenesulfonylamino)-propionic acid compound 36: 3-{2-[1-[2-(3-Methoxy-phenyl)-acetyl]-5-(pyridin-2-ylaminomethyl)-pyrrolidin-3-yloxy]-acetylamino}-2-(2,4,6-trimethyl-benzenesulfonylamino)-propionic acid compound 37: 3-{2-[1-Isobutyryl-5-(pyridin-2-ylaminomethyl)-pyrrolidin-3-yloxy]-acetylamino}-2-(2,4,6-trimethyl-benzenesulfonylamino)-propionic acid compound 38: 3-{2-[1-Propionyl-5-(pyridin-2-ylaminomethyl)-pyrrolidin-3-yloxy]-acetylamino}-2-(2,4,6-trimethyl-benzenesulfonylamino)-propionic acid compound 39: 3-{2-[1-(2-Phenoxy-acetyl)-5-(pyridin-2-ylaminomethyl)-pyrrolidin-3-yloxy]-acetylamino}-2-(2,4,6-trimethyl-benzenesulfonylamino)-propionic acid compound 40: 3-{2-[1-Benzoyl-5-(pyridin-2-ylaminomethyl)-pyrrolidin-3-yloxy]-acetylamino}-2-(2,4,6-trimethyl-benzenesulfonylamino)-propionic acid compound 41: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid isobutyl ester compound 42: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid ethyl ester compound 43: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid hexyl ester compound 44: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid prop-2-ynyl ester compound 45: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid but-3-enyl ester compound 46: 3-{2-[1-Benzylcarbamoyl-5-(pyridin-2-ylaminomethyl)-pyrrolidin-3-yloxy]-acetylamino}-2-(2,4,6-trimethyl-benzenesulfonylamino)-propionic acid compound 47: 3-{2-[1-Carbamoyl-5-(pyridin-2-ylaminomethyl)-pyrrolidin-3-yloxy]-acetylamino}-2-(2,4,6-trimethyl-benzenesulfonylamino)-propionic acid compound 48: 3-{2-[5-(Pyridin-2-ylaminomethyl)-1-(2-trifluoromethyl-phenylcarbamoyl)-pyrrolidin-3-yloxy]-acetylamino}-2-(2,4,6-trimethyl-benzenesulfonylamino)-propionic acid compound 49: 3-{2-[1-(Benzo[1,3]dioxol-5-ylcarbamoyl)-5-(pyridin-2-ylaminomethyl)-pyrrolidin-3-yloxy]-acetylamino}-2-(2,4,6-trimethyl-benzenesulfonylamino)-propionic acid compound 50: 3-{2-[1-(Biphenyl-4-ylcarbamoyl)-5-(pyridin-2-ylaminomethyl)-pyrrolidin-3-yloxy]-acetylamino}-2-(2,4,6-trimethyl-benzenesulfonylamino)-propionic acid compound 51: 3-{2-[1-Benzylthiocarbamoyl-5-(pyridin-2-ylaminomethyl)-pyrrolidin-3-yloxy]-acetylamino}-2-(2,4,6-trimethyl-benzenesulfonylamino)-propionic acid compound 52: 3-{2-[1-Acetyl-5-(pyridin-2-ylaminomethyl)-pyrrolidin-3-yloxy]-acetylamino}-2-(2,4,6-trimethyl-benzenesulfonylamino)-propionic acid compound 53: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid methyl ester compound 54: 3-{2-[1-[2-(2-Methoxy-ethoxy)-acetyl]-5-(pyridin-2-ylaminomethyl)-pyrrolidin-3-yloxy]-acetylamino}-2-(2,4,6-trimethyl-benzenesulfonylamino)-propionic acid compound 55: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid 4-fluoro-benzyl ester compound 56: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid 4-chloro-benzyl ester compound 57: 3-{2-[1-[3-(4-Fluoro-phenyl)-propionyl]-5-(pyridin-2-ylaminomethyl)-pyrrolidin-3-yloxy]-acetylamino}-2-(2,4,6-trimethyl-benzenesulfonylamino)-propionic acid compound 58: 3-{2-[1-[3-(4-Chloro-phenyl)-propionyl]-5-(pyridin-2-ylaminomethyl)-pyrrolidin-3-yloxy]-acetylamino}-2-(2,4,6-trimethyl-benzenesulfonylamino)-propionic acid compound 59: 4-{[2-Ethoxycarbonyl-2-(2,4,6-trimethyl-benzenesulfonylamino)-ethylcarbamoyl]-methoxy}-2-(pyridin-2-ylaminomethyl)-pyrrolidine-1-carboxylic acid benzyl ester compound 60: 3-{2-[1-(3,3-Dimethyl-butyryl)-5-(pyridin-2-ylaminomethyl)-pyrrolidin-3-yloxy]-acetylamino}-2-(2,4,6-trimethyl-benzoylamino)-propionic acid compound 61: 5-{[4-{[2-Carboxy-2-(2,4,6-trimethyl-benzenesulfonylamino)-ethylcarbamoyl]-methoxy}-2-(pyridin-2-ylaminomethyl)-pyrrolidine-1-carbothioyl]-amino}-2-(6-hydroxy-3-oxo-3H-xanthen-9-yl)-benzoic acid compound 62: 3-{2-[1-(Anthracene-2-sulfonyl)-5-(pyridin-2-ylaminomethyl)-pyrrolidin 3-yloxy]-acetylamino}-2-(2,4,6-trimethyl-benzenesulfonylamino)-propionic acid compound 63: 3-{2-[1-(2,2,3,3,4,4,5,5,6,6,7,7,8,8,8-Pentadecafluoro-octanoyl)-5-(pyridin-2-ylaminomethyl)-pyrrolidin-3-yloxy]-acetylamino}-2-(2,4,6-trimethyl-benzenesulfonylamino)-propionic acid compound 64: 3-{2-[1-(3,5-Bis-trifluoromethyl-benzoyl)-5-(pyridin-2-ylaminomethyl)-pyrrolidin-3-yloxy]-acetylamino}-2-(2,4,6-trimethyl-benzenesulfonylamino)-propionic acid compound 65: 3-{2-[1-(3,3-Dimethyl-butyryl)-5-(pyridin-2-ylaminomethyl)-pyrrolidin-3-yloxy]-acetylamino}-2-[(1-methyl-cyclohexanecarbonyl)-amino]-propionic acid compound 66: 4-{[2-Carboxy-2-(2,4,6-trimethyl-benzoylamino)-ethylcarbamoyl]-methoxy}-2-[(4-methoxy-pyridin-2-ylamino)-methyl]-pyrrolidine-1-carboxylic acid benzyl ester compound 67: 4-{[2-(Butane-1-sulfonylamino)-2-carboxy-ethylcarbamoyl]-methoxy}-2-(pyridin-2-ylaminomethyl)-pyrrolidine-1-carboxylic acid benzyl ester compound 68: 4-[(2-Carboxy-2-phenylmethanesulfonylamino-ethylcarbamoyl)-methoxy]-2-(pyridin-2-ylaminomethyl)-pyrrolidine-1-carboxylic acid benzyl ester compound 69: 4-[(2-Carboxy-2-methanesulfonylamino-ethylcarbamoyl)-methoxy]-2-(pyridin-2-ylaminomethyl)-pyrrolidine-1-carboxylic acid benzyl ester compound 70: 4-[(2-Benzoylamino-2-carboxy-ethylcarbamoyl)-methoxy]-2-(pyridin-2-ylaminomethyl)-pyrrolidine-1-carboxylic acid benzyl ester compound 71: 4-{[2-Carboxy-2-(2,4,6-trimethyl-benzoylamino)-ethylcarbamoyl]-methoxy}-2-(pyridin-2-ylaminomethyl)-pyrrolidine-1-carboxylic acid benzyl ester compound 72: 4-[(2-Carboxy-2-phenylacetylamino-ethylcarbamoyl)-methoxy]-2-(pyridin-2-ylaminomethyl)-pyrrolidine-1-carboxylic acid benzyl ester compound 73: 4-({2-[(Biphenyl-4-carbonyl)-amino]-2-carboxy-ethylcarbamoyl}-methoxy)-2-(pyridin-2-ylaminomethyl)-pyrrolidine-1-carboxylic acid benzyl ester compound 74: 4-{[2-Carboxy-2-(3-phenyl-propionylamino)-ethylcarbamoyl]-methoxy}-2-(pyridin-2-ylaminomethyl)-pyrrolidine-1-carboxylic acid benzyl ester compound 75: 4-{[2-(3-Butyl-ureido)-2-carboxy-ethylcarbamoyl]-methoxy}-2-(pyridin-2-ylaminomethyl)-pyrrolidine-1-carboxylic acid benzyl ester compound 76: 4-{[2-Carboxy-2-(3-phenyl-ureido)-ethylcarbamoyl]-methoxy}-2-(pyridin-2-ylaminomethyl)-pyrrolidine-1-carboxylic acid benzyl ester compound 77: 4-{[2-(3-Benzyl-ureido)-2-carboxy-ethylcarbamoyl]-methoxy}-2-(pyridin-2-ylaminomethyl)-pyrrolidine-1-carboxylic acid benzyl ester compound 78: 4-({2-Carboxy-2-[3-(2,6-dimethyl-phenyl)-ureido]-ethylcarbamoyl}-methoxy)-2-(pyridin-2-ylaminomethyl)-pyrrolidine-1-carboxylic acid benzyl ester compound 79: 4-{[2-Carboxy-2-(3-phenethyl-ureido)-ethylcarbamoyl]-methoxy}-2-(pyridin-2-ylaminomethyl)-pyrrolidine-1-carboxylic acid benzyl ester compound 80: 4-{[2-(3-Biphenyl-4-yl-ureido)-2-carboxy-ethylcarbamoyl]-methoxy}-2-(pyridin-2-ylaminomethyl)-pyrrolidine-1-carboxylic acid benzyl ester compound 81: 4-[(2-Amino-2-carboxy-ethylcarbamoyl)-methoxy]-2-(pyridin-2-ylaminomethyl)-pyrrolidine-1-carboxylic acid benzyl ester compound 82: 4-{[2-Carboxy-2-(2,4,6-trimethyl-benzoylamino)-ethylcarbamoyl]-methoxy}-2-(pyridin-2-ylaminomethyl)-pyrrolidine-1-carboxylic acid benzyl ester compound 83: 4-{[2-Carboxy-2-(2-trifluoromethyl-benzoylamino)-ethylcarbamoyl]-methoxy}-2-(pyridin-2-ylaminomethyl)-pyrrolidine-1-carboxylic acid benzyl ester compound 84: 4-{[2-Carboxy-2-(3-trifluoromethyl-benzoylamino)-ethylcarbamoyl]-methoxy}-2-(pyridin-2-ylaminomethyl)-pyrrolidine-1-carboxylic acid benzyl ester compound 85: 4-{[2-Carboxy-2-(4-trifluoromethyl-benzoylamino)-ethylcarbamoyl]-methoxy}-2-(pyridin-2-ylaminomethyl)-pyrrolidine-1-carboxylic acid benzyl ester compound 86: 4-{[2-(3,5-Bis-trifluoromethyl-benzoylamino)-2-carboxy-ethylcarbamoyl]-methoxy}-2-(pyridin-2-ylaminomethyl)-pyrrolidine-1-carboxylic acid benzyl ester compound 87: 4-{[2-Carboxy-2-(2-methyl-benzoylamino)-ethylcarbamoyl]-methoxy}-2-(pyridin-2-ylaminomethyl)-pyrrolidine-1-carboxylic acid benzyl ester compound 88: 4-{[2-Carboxy-2-(2-methoxy-benzoylamino)-ethylcarbamoyl]-methoxy}-2-(pyridin-2-ylaminomethyl)-pyrrolidine-1-carboxylic acid benzyl ester compound 89: 4-{[2-Carboxy-2-(4-methyl-benzoylamino)-ethylcarbamoyl]-methoxy}-2-(pyridin-2-ylaminomethyl)-pyrrolidine-1-carboxylic acid benzyl ester compound 90: 4-{[2-Carboxy-2-(2,6-dimethoxy-benzoylamino)-ethylcarbamoyl]-methoxy}-2-(pyridin-2-ylaminomethyl)-pyrrolidine-1-carboxylic acid benzyl ester compound 91: 4-{[2-Carboxy-2-(cyclohexanecarbonyl-amino)-ethylcarbamoyl]-methoxy}-2-(pyridin-2-ylaminomethyl)-pyrrolidine-1-carboxylic acid benzyl ester compound 92: 4-{[2-Carboxy-2-(2,6-dimethyl-benzoylamino)-ethylcarbamoyl]-methoxy}-2-(pyridin-2-ylaminomethyl)-pyrrolidine-1-carboxylic acid benzyl ester compound 93: 4-{[2-Carboxy-2-(3,5-dimethyl-benzoylamino)-ethylcarbamoyl]-methoxy}-2-(pyridin-2-ylaminomethyl)-pyrrolidine-1-carboxylic acid benzyl ester compound 94: 4-{[2-Carboxy-2-(3,4,5-trimethoxy-benzoylamino)-ethylcarbamoyl]-methoxy}-2-(pyridin-2-ylaminomethyl)-pyrrolidine-1-carboxylic acid benzyl ester compound 95: 4-{[2-Carboxy-2-(2-fluoro-benzoylamino)-ethylcarbamoyl]-methoxy}-2-(pyridin-2-ylaminomethyl)-pyrrolidine-1-carboxylic acid benzyl ester compound 96: 4-{[2-Carboxy-2-(2-nitro-benzoylamino)-ethylcarbamoyl]-methoxy}-2-(pyridin-2-ylaminomethyl)-pyrrolidine-1-carboxylic acid benzyl ester compound 97: 4-{[2-Carboxy-2-(2-chloro-benzoylamino)-ethylcarbamoyl]-methoxy}-2-(pyridin-2-ylaminomethyl)-pyrrolidine-1-carboxylic acid benzyl ester compound 98: 4-{[2-Carboxy-2-(2,6-dichloro-benzoylamino)-ethylcarbamoyl]-methoxy}-2-(pyridin-2-ylaminomethyl)-pyrrolidine-1-carboxylic acid benzyl ester compound 99: 4-{[2-Carboxy-2-(2,6-difluoro-benzoylamino)-ethylcarbamoyl]-methoxy}-2-(pyridin-2-ylaminomethyl)-pyrrolidine-1-carboxylic acid benzyl ester compound 100: 4-({2-Carboxy-2-[(3-methyl-thiophene-2-carbonyl)-amino]-ethylcarbamoyl}-methoxy)-2-(pyridin-2-ylaminomethyl)-pyrrolidine-1-carboxylic acid benzyl ester compound 101: 4-({2-Carboxy-2-[(1-methyl-cyclohexanecarbonyl)-amino]-ethylcarbamoyl}-methoxy)-2-(pyridin-2-ylaminomethyl)-pyrrolidine-1-carboxylic acid benzyl ester compound 102: 4-{[2-Carboxy-2-(3-methyl-2-phenyl-butyrylamino)-ethylcarbamoyl]-methoxy}-2-(pyridin-2-ylaminomethyl)-pyrrolidine-1-carboxylic acid benzyl ester compound 103: 4-{[2-Carboxy-2-(2-ethyl-benzoylamino)-ethylcarbamoyl]-methoxy}-2-(pyridin-2-ylaminomethyl)-pyrrolidine-1-carboxylic acid benzyl ester compound 104: 4-({2-[(Biphenyl-2-carbonyl)-amino]-2-carboxy-ethylcarbamoyl}-methoxy)-2-(pyridin-2-ylaminomethyl)-pyrrolidine-1-carboxylic acid benzyl ester compound 105: 4-({2-Carboxy-2-[(2-methyl-cyclohexanecarbonyl)-amino]-ethylcarbamoyl}-methoxy)-2-(pyridin-2-ylaminomethyl)-pyrrolidine-1-carboxylic acid benzyl ester compound 106: 4-({2-Carboxy-2-[(1-phenyl-cyclopropanecarbonyl)-amino]-ethylcarbamoyl}-methoxy)-2-(pyridin-2-ylaminomethyl)-pyrrolidine-1-carboxylic acid benzyl ester compound 107: 4-({2-Carboxy-2-[(1-phenyl-cyclopentanecarbonyl)-amino]-ethylcarbamoyl}-methoxy)-2-(pyridin-2-ylaminomethyl)-pyrrolidine-1-carboxylic acid benzyl ester compound 108: 4-{[2-Carboxy-2-(2,2-dicyclohexyl-acetylamino)-ethylcarbamoyl]-methoxy}-2-(pyridin-2-ylaminomethyl)-pyrrolidine-1-carboxylic acid benzyl ester compound 109: 4-{[2-Carboxy-2-(2-dimethylamino-benzoylamino)-ethylcarbamoyl]-methoxy}-2-(pyridin-2-ylaminomethyl)-pyrrolidine-1-carboxylic acid benzyl ester compound 110: 4-{[2-Carboxy-2-(2-difluoromethylsulfanyl-benzoylamino)-ethylcarbamoyl]-methoxy}-2-(pyridin-2-ylaminomethyl)-pyrrolidine-1-carboxylic acid benzyl ester compound 111: 4-{[2-Carboxy-2-(2-methyl-pentanoylamino)-ethylcarbamoyl]-methoxy}-2-(pyridin-2-ylaminomethyl)-pyrrolidine-1-carboxylic acid benzyl ester compound 112: 4-{[2-Carboxy-2-(3-cyclopentyl-propionylamino)-ethylcarbamoyl]-methoxy}-2-(pyridin-2-ylaminomethyl)-pyrrolidine-1-carboxylic acid benzyl ester compound 113: 4-{[2-Carboxy-2-(cyclobutanecarbonylamino)-ethylcarbamoyl]-methoxy}-2-(pyridin-2-ylaminomethyl)-pyrrolidine-1-carboxylic acid benzyl ester compound 114: 4-{[2-Carboxy-2-(3,3-dimethyl-butyrylamino)-ethylcarbamoyl]-methoxy}-2-(pyridin-2-ylaminomethyl)-pyrrolidine-1-carboxylic acid benzyl ester compound 115: 4-{[2-Carboxy-2-(3,5,5-trimethyl-hexanoylamino)-ethylcarbamoyl]-methoxy}-2-(pyridin-2-ylaminomethyl)-pyrrolidine-1-carboxylic acid benzyl ester compound 116: 4-[(2-Carboxy-2-propionylamino-ethylcarbamoyl)-methoxy]-2-(pyridin-2-ylaminomethyl)-pyrrolidine-1-carboxylic acid benzyl ester compound 117: 4-{[2-Carboxy-2-(2,2-dimethyl-propionylamino)-ethylcarbamoyl]-methoxy}-2-(pyridin-2-ylaminomethyl)-pyrrolidine-1-carboxylic acid benzyl ester compound 118: 4-{[2-Carboxy-2-(2,2-dimethyl-butyrylamino)-ethylcarbamoyl]-methoxy}-2-(pyridin-2-ylaminomethyl)-pyrrolidine-1-carboxylic acid benzyl ester compound 119: 4-{[2-Carboxy-2-(cyclopropanecarbonylamino)-ethylcarbamoyl]-methoxy}-2-(pyridin-2-ylaminomethyl)-pyrrolidine-1-carboxylic acid benzyl ester compound 120: 4-{[2-Carboxy-2-(2-cyclopentyl-acetylamino)-ethylcarbamoyl]-methoxy}-2-(pyridin-2-ylaminomethyl)-pyrrolidine-1-carboxylic acid benzyl ester compound 121: 4-[(2-Carboxy-2-isobutyrylamino-ethylcarbamoyl)-methoxy]-2-(pyridin-2-ylaminomethyl)-pyrrolidine-1-carboxylic acid benzyl ester compound 122: 4-{[2-Carboxy-2-(2-cyclohexyl-acetylamino)-ethylcarbamoyl]-methoxy}-2-(pyridin-2-ylaminomethyl)-pyrrolidine-1-carboxylic acid benzyl ester compound 123: 4-{[2-Carboxy-2-(2-propyl-pentanoylamino)-ethylcarbamoyl]-methoxy}-2-(pyridin-2-ylaminomethyl)-pyrrolidine-1-carboxylic acid benzyl ester compound 124: 4-{[2-Carboxy-2-(4-methyl-pentanoylamino)-ethylcarbamoyl]-methoxy}-2-(pyridin-2-ylaminomethyl)-pyrrolidine-1-carboxylic acid benzyl ester compound 125: 4-{[2-Carboxy-2-(2-cycloheptyl-acetylamino)-ethylcarbamoyl]-methoxy}-2-(pyridin-2-ylaminomethyl)-pyrrolidine-1-carboxylic acid benzyl ester compound 126: 4-{[2-Carboxy-2-(2,4,6-triisopropyl-benzoylamino)-ethylcarbamoyl]-methoxy}-2-(pyridin-2-ylaminomethyl)-pyrrolidine-1-carboxylic acid benzyl ester compound 127: 4-{[2-Carboxy-2-(4-phenyl-butyrylamino)-ethylcarbamoyl]-methoxy}-2-(pyridin-2-ylaminomethyl)-pyrrolidine-1-carboxylic acid benzyl ester compound 128: 4-{[2-Carboxy-2-(5-phenyl-pentanoylamino)-ethylcarbamoyl]-methoxy}-2-(pyridin-2-ylaminomethyl)-pyrrolidine-1-carboxylic acid benzyl ester compound 129: 2-[(1H-Benzoimidazol-2-ylamino)-methyl]-4-{[2-carboxy-2-(2,4,6-trimethyl-benzenesulfonylamino)-ethylcarbamoyl]-methoxy}-pyrrolidine-1-carboxylic acid benzyl ester compound 130: 4-{[2-Carboxy-2-(2,4,6-trimethyl-benzenesulfonylamino)-ethylcarbamoyl]-methoxy}-2-(pyrimidin-2-ylaminomethyl)-pyrrolidine-1-carboxylic acid benzyl ester compound 131: 4-{[2-Carboxy-2-(2,4,6-trimethyl-benzenesulfonylamino)-ethylcarbamoyl]-methoxy}-2-[(5-chloropyridin-2-ylamino)-methyl]-pyrrolidine-1-carboxylic acid benzyl ester compound 132: 4-{[2-Carboxy-2-(2,4,6-trimethyl-benzenesulfonylamino)-ethylcarbamoyl]-methoxy}-2-[(2H-imidazol-2-ylamino)-methyl]-pyrrolidine-1-carboxylic acid benzyl ester compound 133: 4-{[2-Carboxy-2-(2,4,6-trimethyl-benzenesulfonylamino)-ethylcarbamoyl]-methoxy}-2-(isoquinolin-3-ylaminomethyl)-pyrrolidine-1-carboxylic acid benzyl ester compound 134: 4-{[2-Carboxy-2-(2,4,6-trimethyl-benzenesulfonylamino)-ethylcarbamoyl]-methoxy}-2-[(5-trifluoromethyl-pyridin-2-ylamino)-methyl]-pyrrolidine-1-carboxylic acid benzyl ester compound 135: 4-{[2-Carboxy-2-(2,4,6-trimethyl-benzenesulfonylamino)-ethylcarbamoyl]-methoxy}-2-[(1H-pyrazol-3-ylamino)-methyl]-pyrrolidine-1-carboxylic acid benzyl ester compound 136: 4-{[2-Carboxy-2-(2,4,6-trimethyl-benzenesulfonylamino)-ethylcarbamoyl]-methoxy}-2-[(5-methyl-pyridin-2-ylamino)-methyl]-pyrrolidine-1-carboxylic acid benzyl ester compound 137: 4-{[2-Carboxy-2-(2,4,6-trimethyl-benzenesulfonylamino)-ethylcarbamoyl]-methoxy}-2-[(6-methyl-pyridin-2-ylamino)-methyl]-pyrrolidine-1-carboxylic acid benzyl ester compound 138: 2-[(6-Amino-pyridin-2-ylamino)-methyl]-4-{[2-carboxy-2-(2,4,6-trimethyl-benzenesulfonylamino)-ethylcarbamoyl]-methoxy}-pyrrolidine-1-carboxylic acid benzyl ester compound 139: 4-{[2-Carboxy-2-(2,4,6-trimethyl-benzenesulfonylamino)-ethylcarbamoyl]-methoxy}-2-[(4,6-dimethyl-pyridin-2-ylamino)-methyl]-pyrrolidine-1-carboxylic acid benzyl ester compound 140: 4-{[2-Carboxy-2-(2,4,6-trimethyl-benzenesulfonylamino)-ethylcarbamoyl]-methoxy}-2-(quinolin-2-ylaminomethyl)-pyrrolidine-1-carboxylic acid benzyl ester compound 141: 4-{[2-Carboxy-2-(2,4,6-trimethyl-benzenesulfonylamino)-ethylcarbamoyl]-methoxy}-2-[(5-phenyl-pyridin-2-ylamino)-methyl]-pyrrolidine-1-carboxylic acid benzyl ester compound 142: 4-{[2-Carboxy-2-(2,4,6-trimethyl-benzenesulfonylamino)-ethylcarbamoyl]-methoxy}-2-[(4-methyl-pyridin-2-ylamino)-methyl]-pyrrolidine-1-carboxylic acid benzyl ester compound 143: 4-{[2-Carboxy-2-(2,4,6-trimethyl-benzenesulfonylamino)-ethylcarbamoyl]-methoxy}-2-[(4-methoxy-pyridin-2-ylamino)-methyl]-pyrrolidine-1-carboxylic acid benzyl ester compound 144: 4-{[2-Carboxy-2-(2,4,6-trimethyl-benzenesulfonylamino)-ethylcarbamoyl]-methoxy}-2-[(4-chloro-pyridin-2-ylamino)-methyl]-pyrrolidine-1-carboxylic acid benzyl ester compound 145: 3-(2-{1-(3,3-Dimethyl-butyryl)-5-[(4-methoxy-pyridin-2-ylamino)-methyl]-pyrrolidin-3-yloxy}-acetylamino)-2-(2,4,6-trimethyl-benzenesulfonylamino)-propionic acid compound 146: 3-(2-{1-(3,3-Dimethyl-butyryl)-5-[(4-methoxy-pyridin-2-ylamino)-methyl]-pyrrolidin-3-yloxy}-acetylamino)-2-(2,4,6-trimethyl-benzoylamino)-propionic acid compound 147: 4-({2-Carboxy-2-[(1-methyl-cyclohexanecarbonyl)-amino]-ethylcarbamoyl}-methoxy)-2-[(4-methoxy-pyridin-2-ylamino)-methyl]-pyrrolidine-1-carboxylic acid benzyl ester compound 148: 3-(2-{1-(3,3-Dimethyl-butyryl)-5-[(4-methoxy-pyridin-2-ylamino)-methyl]-pyrrolidin-3-yloxy}-acetylamino)-2-[(1-methyl-cyclohexanecarbonyl)-amino]-propionic acid compound 149: 4-[(1-Carboxymethyl-2-methyl-propylcarbamoyl)-methoxy]-2-(pyridin-2-ylaminomethyl)-pyrrolidine-1-carboxylic acid benzyl ester compound 150: 4-[(1-Carboxymethyl-2-phenyl-ethylcarbamoyl)-methoxy]-2-(pyridin-2-ylaminomethyl)-pyrrolidine-1-carboxylic acid benzyl ester compound 151: 4-[(2-Carboxy-1-phenyl-ethylcarbamoyl)-methoxy]-2-(pyridin-2-ylaminomethyl)-pyrrolidine-1-carboxylic acid benzyl ester compound 152: 4-[(1-Carboxymethyl-2-p-tolyl-ethylcarbamoyl)-methoxy]-2-(pyridin-2-ylaminomethyl)-pyrrolidine-1-carboxylic acid benzyl ester compound 153: 4-[(2-Carboxy-1-phenyl-ethylcarbamoyl)-methoxy]-2-(pyridin-2-ylaminomethyl)-pyrrolidine-1-carboxylic acid benzyl ester compound 154: 4-{[3-Carboxy-3-(2,4,6-trimethyl-benzenesulfonylamino)-propylcarbamoyl]-methoxy}-2-(pyridin-2-ylaminomethyl)-pyrrolidine-1-carboxylic acid benzyl ester compound 155: 4-({[2-Carboxy-2-(2,4,6-trimethyl-benzenesulfonylamino)-ethyl]-methyl-carbamoyl}-methoxy)-2-(pyridin-2-ylaminomethyl)-pyrrolidine-1-carboxylic acid benzyl ester compound 156: 4-[(2-Carboxy-2-phenyl-ethylcarbamoyl)-methoxy]-2-(pyridin-2-ylaminomethyl)-pyrrolidine-1-carboxylic acid benzyl ester compound 157: 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid benzyl ester or any salt, solvate, and prodrug thereof, whereby it is to be acknowledged that this third aspect can also be regarded as an embodiment of the first and second aspect of the present invention.

In a fourth aspect the problem underlying the present invention is solved by the use of a compound according to the first, and third second aspect of the present invention as an inhibitor.

In an embodiment of the fourth aspect the compound is an inhibitor to an integrin.

In an embodiment of the fourth aspect the integrin is alpha5beta1 integrin.

In a fifth aspect the problem underlying the present invention is solved by the use of a compound according to the first, second and third aspect of the present invention for the manufacture of a medicament, preferably a medicament for the treatment and/or prevention of a disease.

In an embodiment of the fifth aspect the medicament is for a disease mediated by or involving alpha5beta1 integrin.

In an embodiment of the fifth aspect the disease is selected from the group comprising diseases based on pathological angiogenesis and/or diseases based on interaction of an integrin with a ligand, whereby preferably the ligand is present on the extracellular matrix and/or on any cell surface.

In an embodiment of the fifth aspect the disease is related to an ocular tissue, the skin, joint, neoplasm, synovial tissue, intestinal tissue and/or the bone tissue.

In an embodiment of the fifth aspect the disease is a disease of an ocular tissue, preferably diabetic retinopathy, retinopathy of prematurity or macular degeneration, more preferably age related macular degeneration by neovascularization.

In an embodiment of the fifth aspect the disease is a disease of the skin, more preferably hemangioma or psoriasis.

In an embodiment of the fifth aspect the disease is a disease of or affecting the joints, more preferably rheumatoid arthritis and/or osteoarthritis.

In an embodiment of the fifth aspect the disease is a neoplasm, more preferably a malignant neoplasm.

In a preferred embodiment of the fifth aspect the malignant neoplasm is a carcinoma, more preferably the carcinoma is selected from the group comprising breast carcinoma, ovarian carcinoma, colon carcinoma, pancreatic carcinoma, bladder carcinoma, sarcoma, mesothelioma, teratocarcinoma, astrocytoma, melanoma, angioma and glioblastoma.

In an embodiment of the fifth aspect the disease is based on an interaction of an integrin with a ligand in the extracellular matrix or on the cell surface. In a preferred embodiment the disease is an inflammatory disease. In an alternative embodiment the disease is an infectious disease.

In an embodiment of the fifth aspect the inflammatory disease is a disease preferably selected from the group comprising gingivitis, inflammatory bowel disease, ulcerative colitis, Crohn's disease and coronary thrombosis.

In an embodiment of the fifth aspect the disease is an infectious disease, more preferably the disease is an infection caused by or involving fungi, bacteria and/or viruses.

In a further embodiment of the fifth aspect the disease is a non-neoplastic cell proliferative disorder, preferably the non-neoplastic cell proliferative disorder is selected from the group comprising fibrotic disorders, and more preferably the fibrotic disorder is fibrosis.

In an embodiment of the fifth aspect the medicament is for the treatment of macular degeneration, and wherein A is selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl, substituted alkylthio-cycloalkyl, benzyl, substituted benzyl, phenyl, substituted phenyl, heterocyclyl, substituted heterocyclyl, aryl, substituted aryl, heterocyclyl, substituted heterocyclyl, arylalkyl, substituted arylalkyl, heteroarylalkyl, substituted heteroarylalkyl, cycloalkylalkyl, substituted cycloalkylalkyl, heterocyclylalkyl substituted heterocyclylalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, arylthio-alkyl, substituted arylthio-alkyl, arylthio-cycloalkyl and substituted arylthio-cycloalkyl.

In an embodiment of the fifth aspect wherein $R_2$ is selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl and substituted alkylthio-cycloalkyl.

In an embodiment of the fifth aspect Q of B is C=O or SO$_2$.

In an embodiment of the fifth aspect the medicament is for the treatment of neoplasms, and wherein A is selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl and substituted alkylthio-cycloalkyl, benzyl, substituted benzyl, phenyl, substituted phenyl, heterocyclyl, substituted heterocyclyl, aryl, substituted aryl, heterocyclyl, substituted heterocyclyl, arylalkyl substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, arylthio-alkyl, substituted arylthio-alkyl, arylthio-cycloalkyl and substituted arylthio-cycloalkyl.

In an embodiment of the fifth aspect R$_2$ is selected from the group comprising benzyl, substituted benzyl, phenyl, substituted phenyl, heterocyclyl, substituted heterocyclyl, aryl, substituted aryl, heterocyclyl, substituted heterocyclyl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy-heterocyclyl, substituted alkyloxy-heterocyclyl, alkyloxy-aryl, substituted alkyloxy-aryl, alkyloxy-heteroaryl, substituted alkyloxy-heteroaryl, arylthio-alkyl, substituted arylthio-alkyl, arylthio-cycloalkyl and substituted arylthio-cycloalkyl.

In an embodiment of the fifth aspect, preferably an embodiment of the two previously described embodiments Q of B is SO$_2$ or C=O.

In an embodiment of the fifth aspect the compounds are the compounds according to the second aspect and the use is for the manufacture of a medicament for the treatment of macular degeneration and/or neoplasms.

In a sixth aspect the problem underlying the present invention is solved by the use of a compound according to the first, second or third aspect as a diagnostic tool or for the manufacture of a diagnostic tool, whereby preferably such diagnostic tool is useful for in vivo and/or for ex vivo application.

In an embodiment of the fourth, fifth and sixth aspect the compound comprises a further moiety, preferably a moiety which is selected from the group comprising a targeted moiety, a delivery moiety, and a detection moiety.

In an embodiment of fourth, fifth and sixth aspect the further moiety is attached, preferably conjugated to the compound according to the first, second or third aspect.

In an embodiment of the fourth, fifth and sixth aspect the detection moiety is a label, whereby preferably the label is selected from the group comprising radionuclide labels, paramagnetic material, X-ray attenuating material, immune labels, colored labels, chemiluminescent labels, luminescent labels, fluorescent labels, enzyme substrates, enzymes, and labels complexing detectable ions.

In an embodiment of the fourth, fifth and sixth aspect the diagnostic tool is used in an in vivo imaging method and/or an ex vivo imaging method, more particularly radionuclide imaging, positron emission tomography, computerized axial tomography, magnetic resonance imaging, luminescence, fluorescence, and chemiluminescence.

In an embodiment of the fourth, fifth and sixth aspect the moiety is a targeted moiety, whereby targeted moiety is preferably a pharmaceutically active moiety, whereby the pharmaceutically active moiety is selected from the group comprising cytotoxins, chemotherapeutics, antibodies, radionuclides and cytotoxic proteins.

In an embodiment of the fourth, fifth and sixth aspect the targeted moiety is selected from the group comprising antibodies, linker molecules and liposomes.

In a seventh aspect the problem underlying the present invention is solved by a pharmaceutical composition comprising a compound according to the first, second or third aspect and a pharmaceutically acceptable carrier, diluent or excipient.

In an embodiment of the seventh aspect the pharmaceutical composition comprises another pharmaceutically active compound.

In an embodiment of the seventh aspect the compound is present as a pharmaceutically acceptable salt or a pharmaceutically active solvate.

In an embodiment of the seventh aspect the compound is either alone or in combination with any of the ingredients of the composition present in a multitude of individualised dosages and/or administration forms.

In an embodiment of the seventh aspect the pharmaceutical composition is for the treatment of a disease, whereby the disease is selected from diseases mediated by or involving alpha5beta1 integrin.

In an embodiment of the seventh aspect the pharmaceutical composition is for the treatment of a disease, whereby the disease is any of the diseases defined in any of the preceding embodiments.

In an embodiment of the seventh aspect the pharmaceutical composition is for use together with a method of treatment for a disease, preferably a disease defined in any of the preceding embodiments.

In a preferred embodiment of the seventh aspect the method of treatment is selected from the group comprising chemotherapy, anti-hormone therapy, radiation therapy, photodynamic therapy, surgery, and anti-angiogenic therapy.

In an eighth aspect the problem underlying the present invention is solved by a method for treating an integrin associated state in a subject comprising administering to said subject an effective amount of a compound according to the first and second aspect such that said integrin associated state is treated.

In an embodiment of the eighth aspect the integrin is alpha5beta1 integrin.

In an ninth aspect the problem underlying the present invention is solved by a method for treating a disease in a subject comprising administering to said subject an effective amount of a compound according to the first, second or third aspect such that the disease is treated.

In an embodiment the disease is any of the diseases defined in any of the embodiments according to the fifth aspect.

Some of the more preferred compounds according to the present invention are summarised in the following table 1 and include any pharmaceutically acceptable salt, solvate or prodrug thereof.

TABLE 1

| No. | Structure | Name | Formula | Mol-Weight | Example | LCMS |
|---|---|---|---|---|---|---|
| 13 | 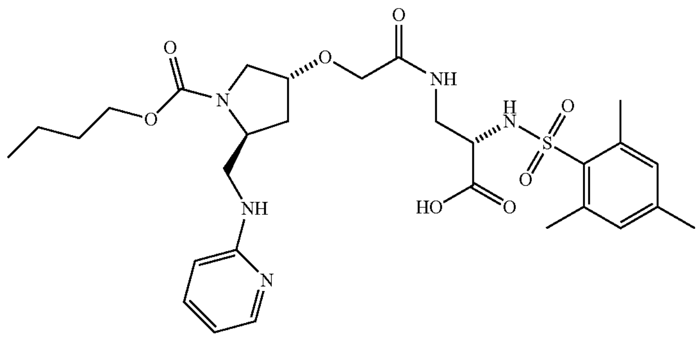 [SMILES: CCCCOC(=O)N1C[C@H](OCC(=O)NC[C@H](NS(=O)(=O)c2c(C)cc(C)cc2C)C(=O)O)C[C@H]1CNc1ccccn1] | 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid butyl ester | C29H41N5O8S | 619.73 | Exp. 6A | 620.5 |
| 14 | 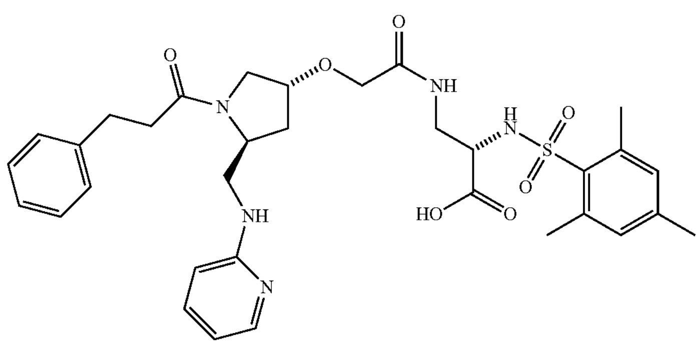 [SMILES: Cc1cc(C)c(S(=O)(=O)N[C@@H](CNC(=O)CO[C@@H]2C[C@@H](CNc3ccccn3)N(C(=O)CCc3ccccc3)C2)C(=O)O)c(C)c1] | 3-{2-[1-(3-Phenyl-propionyl)-5-(pyridin-2-ylaminomethyl)-pyrrolidin-3-yloxy]-acetylamino}-2-(2,4,6-trimethyl-benzenesulfonylamino)-propionic acid | C33H41N5O7S | 651.77 | Exp. A | 652.5 |

TABLE 1-continued

| No. | Name | Structure | Formula | Mol-Weight | Example | LCMS |
|---|---|---|---|---|---|---|
| 15 | 3-{2-[1-Phenylmethanesulfonyl-5-(pyridin-2-ylaminomethyl)-pyrrolidin-3-yloxy]-acetylamino}-2-(2,4,6-trimethyl-benzenesulfonylamino)-propionic aci | 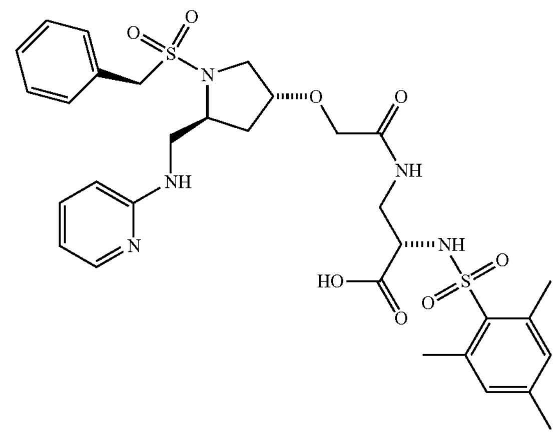 | C31H39N5O8S2 | 673.79 | Exp. 6A | 674.5 |
| 16 | 3-{2-[1-(Butane-1-sulfonyl)-5-(pyridin-2-ylaminomethyl)-pyrrolidin-3-yloxy]-acetylamino)-2-(2,4,6-trimethyl-benzenesulfonylamino)-propionic acid | 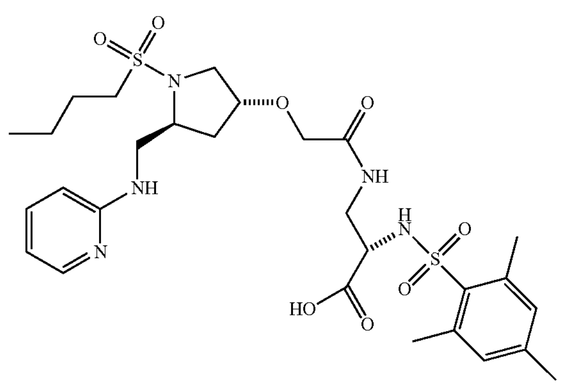 [SMILES: CCCCS(=O)(=O)N1C[C@H](OCC(=O)NC[C@H](NS(=O)(=O)c2c(C)cc(C)cc2C)C(=O)O)C[C@H]1CNc1ccccn1] | C28H41N5O8S2 | 639.78 | Exp. 6A | 640.6 |

TABLE 1-continued

| No. | Structure | Name | Formula | Mol-Weight | Example | LCMS |
|---|---|---|---|---|---|---|
| 17 | 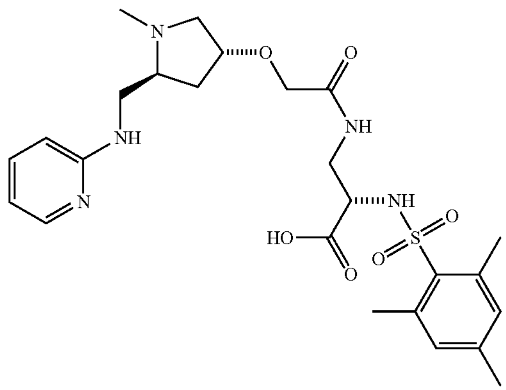 [SMILES: Cc1cc(C)c(S(=O)(=O)N[C@@H](CNC(=O)CO[C@@H]2C[C@@H](CNc3ccccn3)N(C)C2)C(=O)O)c(C)c1] | 3-{2-[1-Methyl-5-(pyridin-2-ylaminomethyl)-pyrrolidin-3-yloxy]-acetylamino}-2-(2,4,6-trimethyl-benzenesulfonylamino)-propionic acid | C25H35N5O6S | 533.64 | Exp. 6C | 534.5 |
| 18 | 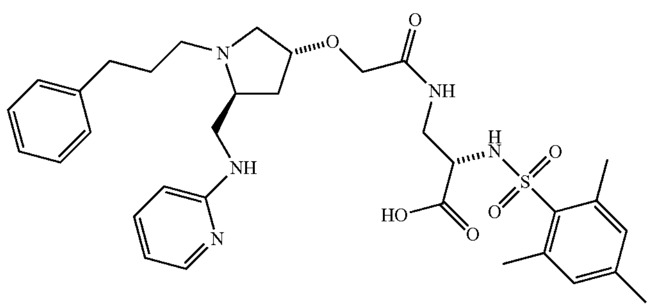 [SMILES: Cc1cc(C)c(S(=O)(=O)N[C@@H](CNC(=O)CO[C@@H]2C[C@@H](CNc3ccccn3)N(CCCc3ccccc3)C2)C(=O)O)c(C)c1] | 3-{2-[1-(3-Phenyl-propyl)-5-(pyridin-2-ylaminomethyl)-pyrrolidin-3-yloxy]-acetylamino}-2-(2,4,6-trimethyl-benzenesulfonylamino)-propionic acid | C33H43N5O6S | 637.79 | Exp. 6C | 638.5 |

TABLE 1-continued

| No. | Structure | Name | Formula | Mol-Weight | Example | LCMS |
|---|---|---|---|---|---|---|
| 19 | 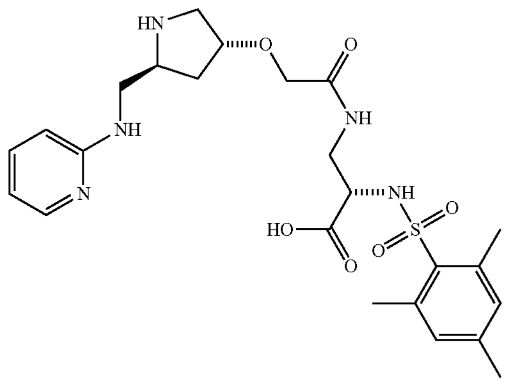 [SMILES: Cc1cc(C)c(S(=O)(=O)N[C@@H](CNC(=O)CO[C@H]2CN[C@H](CNc3ccccn3)C2)C(=O)O)c(C)c1] | 3-{2-[5-(Pyridin-2-ylaminomethyl)-pyrrolidin-3-yloxy]-acetylamino}-2-(2,4,6-trimethyl-benzenesulfonylamino)-propionic acid | C24H33N5O6S | 519.61 | Exp. 6 TFA | 520.5 |
| 20 | 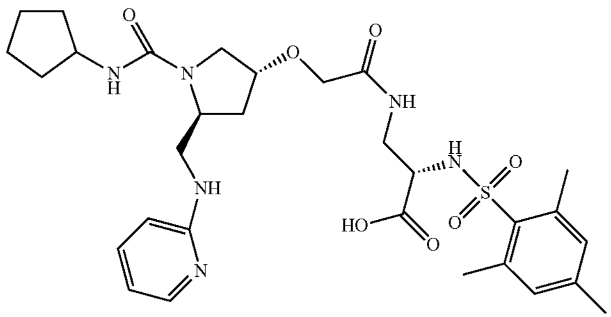 [SMILES: Cc1cc(C)c(S(=O)(=O)N[C@@H](CNC(=O)CO[C@@H]2C[C@@H](CNc3ccccn3)N(C(=O)NC3CCCC3)C2)C(=O)O)c(C)c1] | 3-{2-[1-Cyclopentylcarbamoyl-5-(pyridin-2-ylaminomethyl)-pyrrolidin-3-yloxy]-acetylamino}-2-(2,4,6-trimethyl-benzenesulfonylamino)-propionic acid | C30H42N6O7S | 630.76 | Exp. 6B | 631.5 |
| 21 | 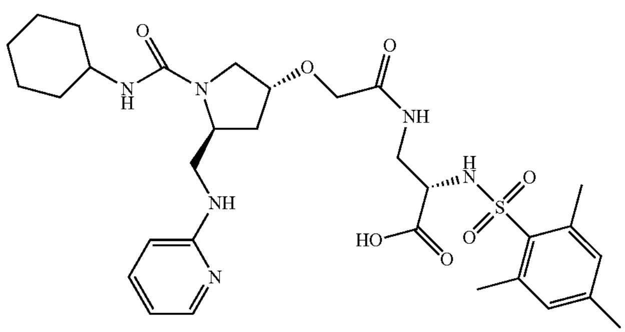 [SMILES: Cc1cc(C)c(S(=O)(=O)N[C@@H](CNC(=O)CO[C@@H]2C[C@@H](CNc3ccccn3)N(C(=O)NC3CCCCC3)C2)C(=O)O)c(C)c1] | 3-{2-[1-Cyclohexylcarbamoyl-5-(pyridin-2-ylaminomethyl)-pyrrolidin-3-yloxy]-acetylamino}-2-(2,4,6-trimethyl-benzenesulfonylamino)-propionic acid | C31H44N6O7S | 644.79 | Exp. 6B | 645.5 |

TABLE 1-continued

| No. | Structure | Name | Formula | Mol-Weight | Example | LCMS |
|---|---|---|---|---|---|---|
| 22 | 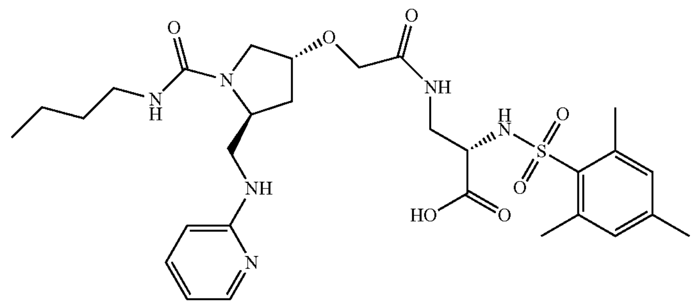 [SMILES: CCCCNC(=O)N1C[C@H](OCC(=O)NC[C@H](NS(=O)(=O)c2c(C)cc(C)cc2C)C(=O)O)C[C@H]1CNc1ccccn1] | 3-(2-[1-Butylcarbamoyl-5-(pyridin-2-ylaminomethyl)-pyrrolidin-3-yloxy]-acetylamino)-2-(2,4,6-trimethyl-benzenesulfonylamino)-propionic acid | C29H42N6O7S | 618.74 | Exp. 6B | 619.4 |
| 23 | 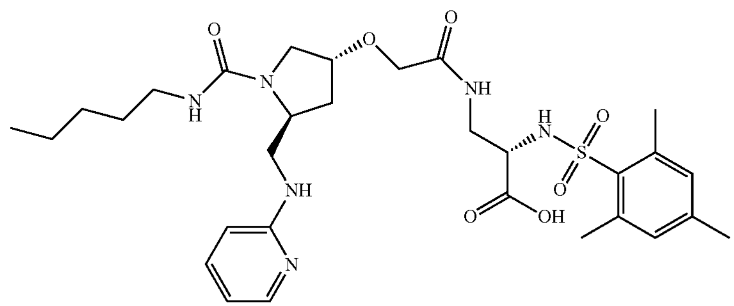 [SMILES: CCCCCNC(=O)N1C[C@H](OCC(=O)NC[C@H](NS(=O)(=O)c2c(C)cc(C)cc2C)C(=O)O)C[C@H]1CNc1ccccn1] | 3-{2-[1-Pentylcarbamoyl-5-(pyridin-2-ylaminomethyl)-pyrrolidin-3-yloxy]-acetylamino}-2-(2,4,6-trimethyl-benzenesulfonylamino)-propionic acid | C30H44N6O7S | 632.77 | Exp. 6B | 633.5 |
| 24 | 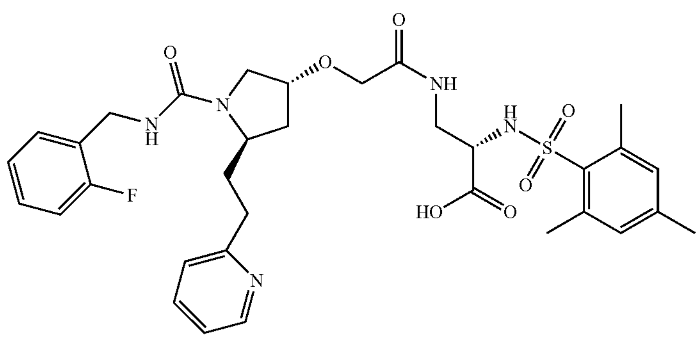 [SMILES: Cc1cc(C)c(S(=O)(=O)N[C@@H](CNC(=O)CO[C@@H]2C[C@@H](CCc3ccccn3)N(C(=O)NCc3ccccc3F)C2)C(=O)O)c(C)c1] | 3-{2-[1-(2-Fluoro-benzylcarbamoyl)-5-(pyridin-2-ylaminomethyl)-pyrrolidin-3-yloxyl-acetylamino}-2-(2,4,6-trimethyl-benzenesulfonylamino)-propionic acid | C32H39FN6O7S | 670.76 | Exp. 6B | 671.5 |

TABLE 1-continued

| No. | Structure | Name | Formula | Mol-Weight | Example | LCMS |
|---|---|---|---|---|---|---|
| 25 | 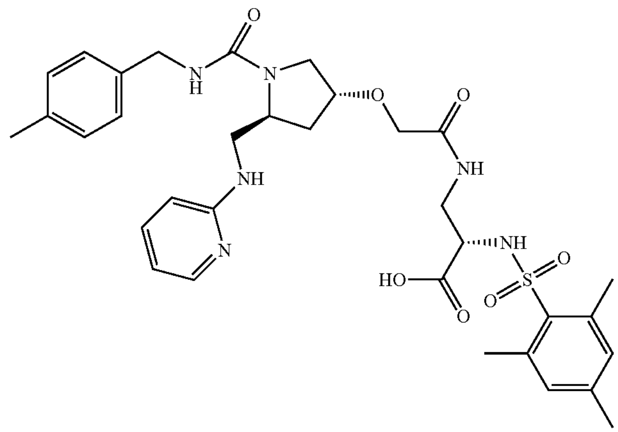 | 3-(2-[1-(4-Methyl-benzylcarbamoyl)-5-(pyridin-2-ylaminomethyl)-pyrrolidin-3-yloxy]-acetylamino)-2-(2,4,6-trimethyl-benzenesulfonylamino)-propionic acid | C33H42N6O7S | 666.80 | Exp. 6B | 667.5 |
| 26 | 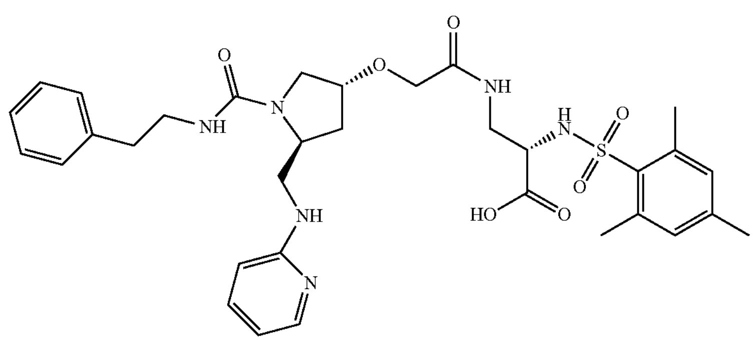 [SMILES: Cc1cc(C)c(S(=O)(=O)N[C@@H](CNC(=O)CO[C@@H]2C[C@@H](CNc3ccccn3)N(C(=O)NCCc3ccccc3)C2)C(=O)O)c(C)c1] | 3-(2-[1-Phenethylcarbamoyl-5-(pyridin-2-ylaminomethyl)-pyrrolidin-3-yloxy]-acetylamino)-2-(2,4,6-trimethyl-benzenesulfonylamino)-propionic acid | C33H42N6O7S | 666.80 | Exp. 6B | 667.5 |

TABLE 1-continued

| No. | Name | Structure | Formula | Mol-Weight | Example | LCMS |
|---|---|---|---|---|---|---|
| 27 | 3-{2-[1-(3-Methyl-benzylcarbamoyl)-5-(pyridin-2-ylaminomethyl)-pyrrolidin-3-yloxy]-acetylamino}-2-(2,4,6-trimethyl-benzenesulfonylamino)-propionic acid | 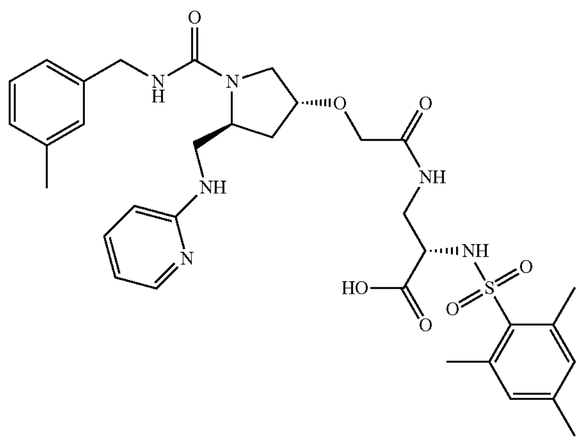 [SMILES: Cc1cccc(CNC(=O)N2C[C@H](OCC(=O)NC[C@H](NS(=O)(=O)c3c(C)cc(C)cc3C)C(=O)O)C[C@H]2CNc2ccccn2)c1] | C33H42N6O7S | 666.80 | Exp. 6B | 667.3 |
| 28 | 3-{2-[1-Phenylcarbamoyl-5-(pyridin-2-ylaminomethyl)-pyrrolidin-3-yloxy]-acetylamino}-2-(2,4,6-trimethyl-benzenesulfonylamino)-propionic acid | 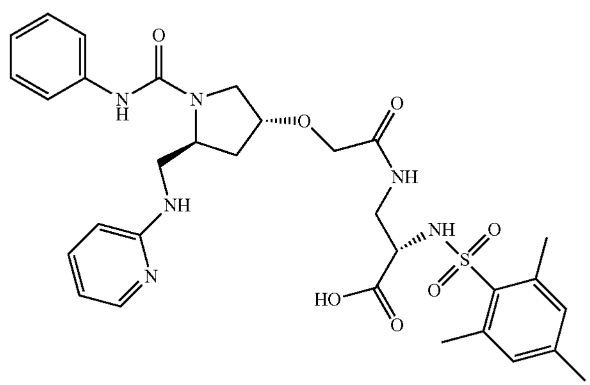 [SMILES: Cc1cc(C)c(S(=O)(=O)N[C@@H](CNC(=O)CO[C@@H]2C[C@@H](CNc3ccccn3)N(C(=O)Nc3ccccc3)C2)C(=O)O)c(C)c1] | C31H38N6O7S | 638.74 | Exp. 6B | 639.4 |

TABLE 1-continued

| No. | Structure | Name | Formula | Mol-Weight | Example | LCMS |
|---|---|---|---|---|---|---|
| 29 | 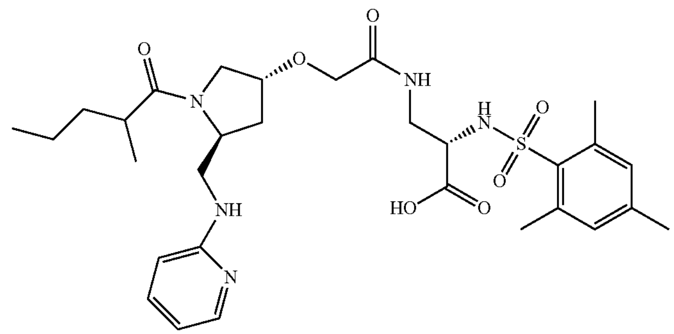 [SMILES: CCCC(C)C(=O)N1C[C@H](OCC(=O)NC[C@H](NS(=O)(=O)c2c(C)cc(C)cc2C)C(=O)O)C[C@H]1CNc1ccccn1] | 3-{2-[1-(2-Methyl-pentanoyl)-5-(pyridin-2-ylaminomethyl)-pyrrolidin-3-yloxy]-acetylamino}-2-(2,4,6-trimethyl-benzenesulfonylamino)-propionic acid | C30H43N5O7 | 617.76 | Exp. 6B | 618.5 |
| 30 | 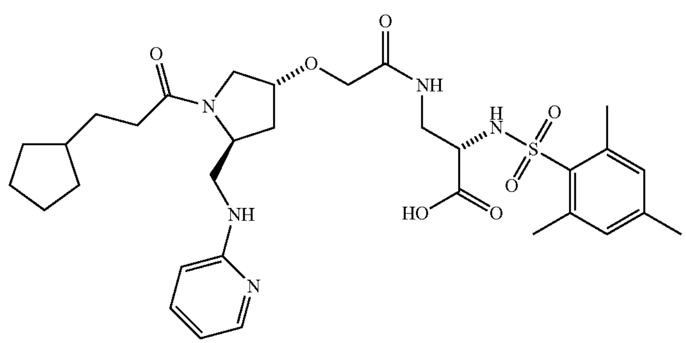 [SMILES: Cc1cc(C)c(S(=O)(=O)N[C@@H](CNC(=O)CO[C@@H]2C[C@@H](CNc3ccccn3)N(C(=O)CCC3CCCC3)C2)C(=O)O)c(C)c1] | 3-{2-[1-(3-Cyclopentyl-propionyl)-5-(pyridin-2-ylaminomethyl)-pyrrolidin-3-yloxyl-acetylamino]-2-(2,4,6-trimethyl-benzenesulfonylamino)-propionic acid | C32H45N5O7S | 643.79 | Exp. 6A | 644.6 |

TABLE 1-continued

| No. | Structure | Name | Formula | Mol-Weight | Example | LCMS |
|---|---|---|---|---|---|---|
| 31 | 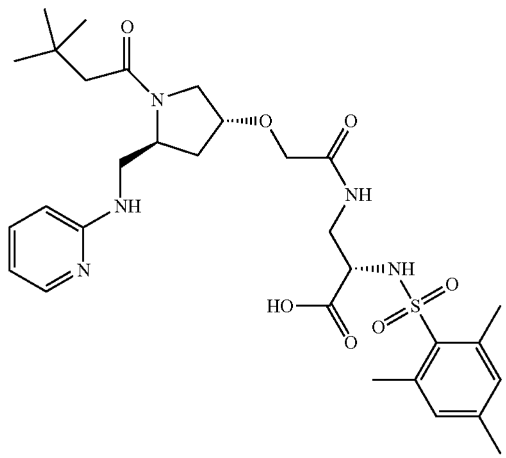 [SMILES: Cc1cc(C)c(S(=O)(=O)N[C@@H](CNC(=O)CO[C@@H]2C[C@@H](CNc3ccccn3)N(C(=O)CC(C)(C)C)C2)C(=O)O)c(C)c1] | 3-(2-[1-(3,3-Dimethyl-butyryl)-5-(pyridin-2-ylaminomethyl)-pyrrolidin-3-yloxy]-acetylamino)-2-(2,4,6-trimethyl-benzenesulfonylamino)-propionic acid | C30H43N5O7S | 617.76 | Exp. 6A | 618.6 |
| 32 | 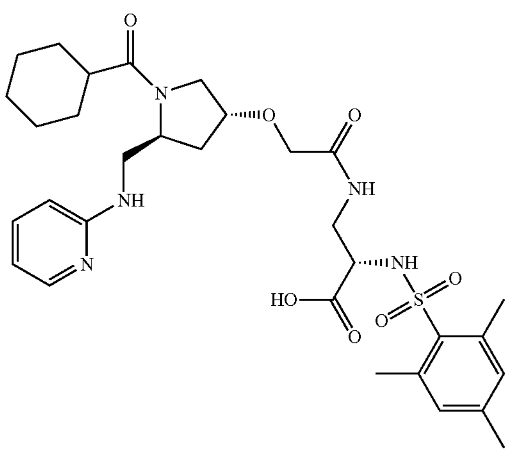 [SMILES: Cc1cc(C)c(S(=O)(=O)N[C@@H](CNC(=O)CO[C@@H]2C[C@@H](CNc3ccccn3)N(C(=O)C3CCCCC3)C2)C(=O)O)c(C)c1] | 3-(2-[1-Cyclohexanecarbonyl-5-(pyridin-2-ylaminomethyl)-pyrrolidin-3-yloxy]-acetylamino)-2-(2,4,6-trimethyl-benzenesulfonylamino)-propionic acid | C31H43N5O7S | 629.77 | Exp. 6A | 630.6 |

TABLE 1-continued
| No. | Structure | Name | Formula | Mol-Weight | Example | LCMS |
|---|---|---|---|---|---|---|
| 33 | 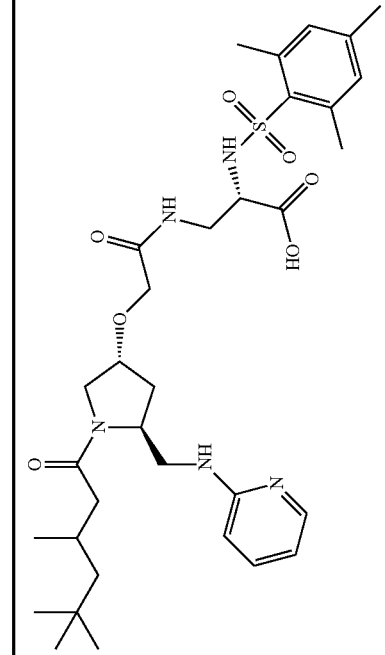 | 3-{2-[5-(Pyridin-2-ylaminomethyl)-1-(3,5,5-trimethyl-hexanoyl)-pyrrolidin-3-yloxy]-acetylamino}-2-(2,4,6-trimethyl-benzenesulfonylamino)-propionic acid | C33H49N5O7S | 659.84 | Exp. 6A | 650.7 |
| 34 | 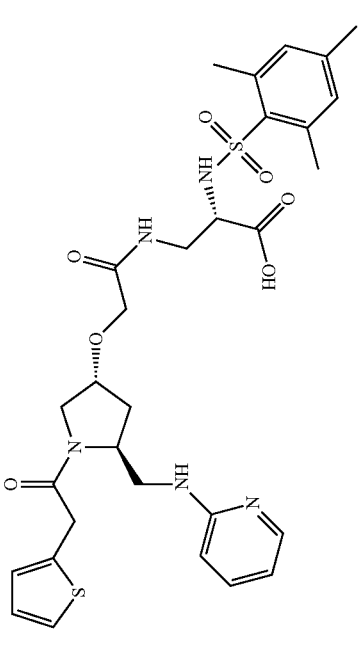 | 3-{2-[5-(Pyridin-2-ylaminomethyl)-1-(2-thiaphen-2-yl-acetyl)-pyrrolidin-3-yloxy]-acetylamino}-2-(2,4,6-trimethyl-propionic acid | C30H37N5O7S2 | 643.77 | Exp. 6A | 644.5 |

TABLE 1-continued
| No. | Structure | Name | Formula | Mol-Weight | Example | LCMS |
|---|---|---|---|---|---|---|
| 35 | 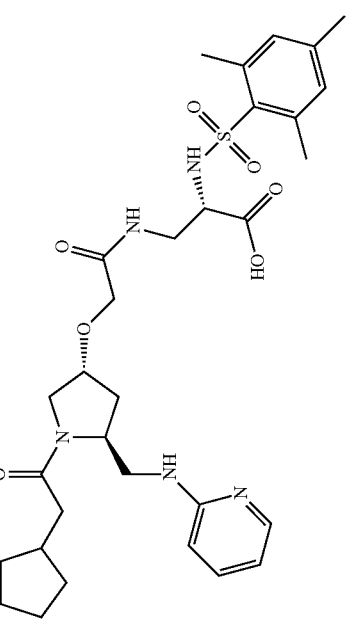 | 3-{2-[1-(2-Cyclopentyl-acetyl)-5-(pyridin-2-ylaminomethyl)-pyrrolidin-3-yloxy]-acetylamino}-2-(2,4,6-trimethyl-benzenesulfonylamino)-propionic acid | C31H43N5O7S | 629.77 | Exp. 6A | 630.6 |
| 36 | 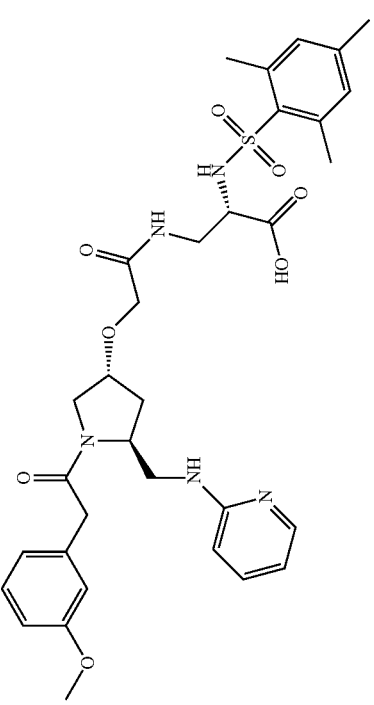 | 3-{2-[1-[2-(3-Methoxy-phenyl)-acetyl]-5-(pyridin-2-ylaminomethyl)-pyrrolidin-3-yloxy]-acetylaminol-2-(2,4,6-trimethyl-benzenesulfonylamino)-propionic acid | C33H41N5O8S | 667.77 | Exp. 6A | 668.6 |

TABLE 1-continued

| No. | Structure | Name | Formula | Mol-Weight | Example | LCMS |
|---|---|---|---|---|---|---|
| 37 | 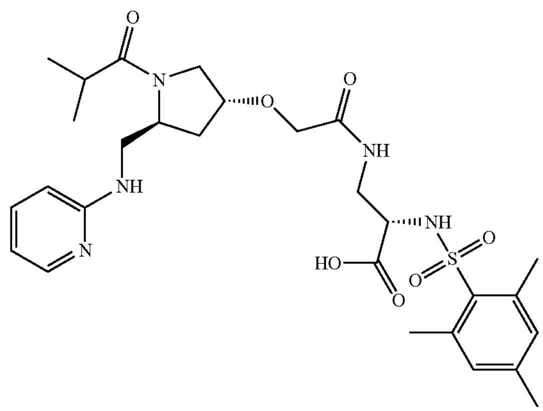 [SMILES: Cc1cc(C)c(S(=O)(=O)N[C@@H](CNC(=O)CO[C@@H]2C[C@@H](CNc3ccccn3)N(C(=O)C(C)C)C2)C(=O)O)c(C)c1] | 3-{2-[1-Isobutyryl-5-(pyridin-2-ylaminomethyl)-pyrrolidin-3-yloxy]-acetylamino}-2-(2,4,6-trimethyl-benzenesulfonylamino)-propionic acid | C28H39N5O7S | 589.70 | Exp. 6A | 590.5 |
| 38 | 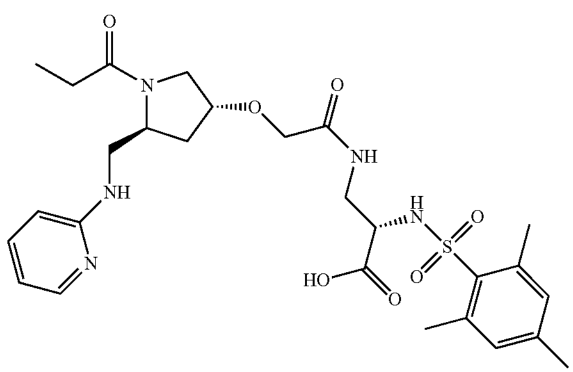 [SMILES: CCC(=O)N1C[C@H](OCC(=O)NC[C@H](NS(=O)(=O)c2c(C)cc(C)cc2C)C(=O)O)C[C@H]1CNc1ccccn1] | 3-{2-[1-Propionyl-5-(pyridin-2-ylaminomethyl)-pyrrolidin-3-yloxy]-acetylamino}-2-(2,4,6-trimethyl-benzenesulfonylamino)-propionic acid | C27H37N5O7S | 575.67 | Exp. 6A | 576.5 |

TABLE 1-continued

| No. | Structure | Name | Formula | Mol-Weight | Example | LCMS |
|---|---|---|---|---|---|---|
| 39 | 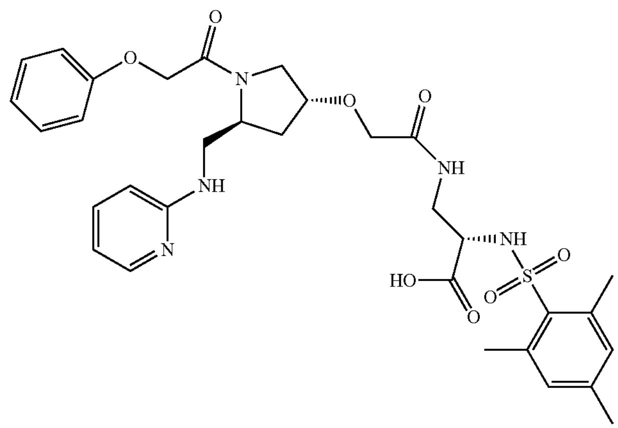 [SMILES: Cc1cc(C)c(S(=O)(=O)N[C@@H](CNC(=O)CO[C@@H]2C[C@@H](CNc3ccccn3)N(C(=O)COc3ccccc3)C2)C(=O)O)c(C)c1] | 3-{2-[1-(2-Phenoxy-acetyl)-5-(pyridin-2-ylaminomethyl)-pyrrolidin-3-yloxy]-acetylamino}-2-(2,4,6-trimethyl-benzenesulfonylamino)-propionic acid | C32H39N5O8S | 667.77 | Exp. 6A | 668.6 |
| 40 | 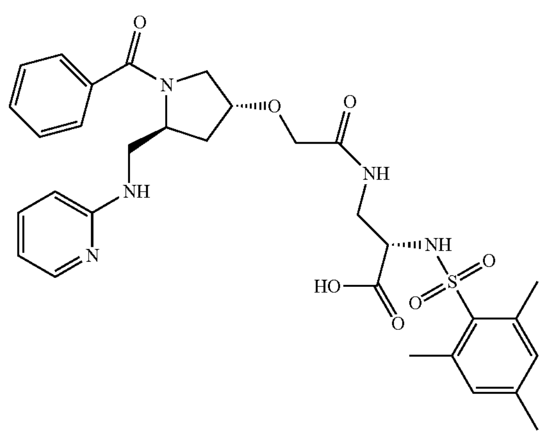 [SMILES: Cc1cc(C)c(S(=O)(=O)N[C@@H](CNC(=O)CO[C@@H]2C[C@@H](CNc3ccccn3)N(C(=O)c3ccccc3)C2)C(=O)O)c(C)c1] | 3-{2-[1-Benzoyl-5-(pyridin-2-ylaminomethyl)-pyrrolidin-3-yloxy]-acetylamino}-2-(2,4,6-trimethyl-benzenesulfonylamino)-propionic acid | C31H37N5O7S | 623.72 | Exp. 6A | 624.5 |

TABLE 1-continued

| No. | Structure | Name | Formula | Mol-Weight | Example | LCMS |
|---|---|---|---|---|---|---|
| 41 | 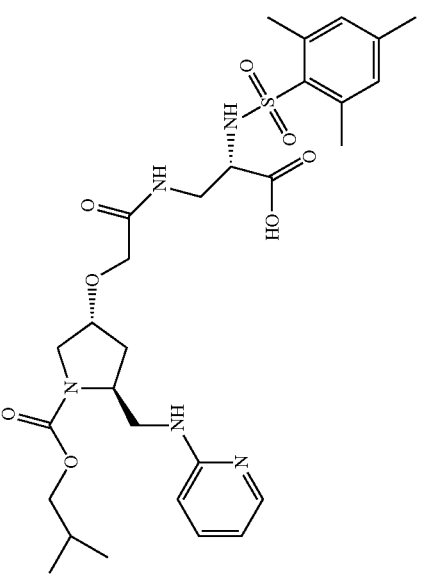 | 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid isobutyl ester | C29H41N5O8S | 619.73 | Exp. 6A | 620 |
| 42 | 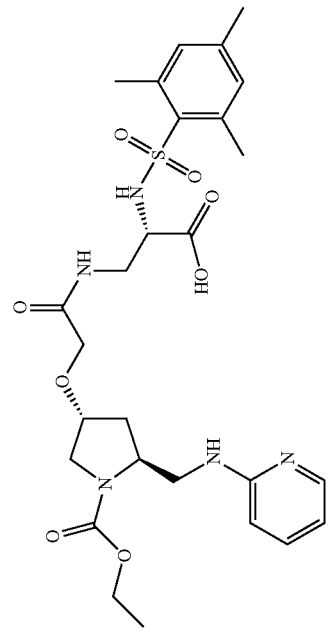 | 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid ethyl ester | C27H37N5O8S | 591.67 | Exp. 6A | 592.5 |

TABLE 1-continued

| No. | Name | Structure | Formula | Mol-Weight | Example | LCMS |
|---|---|---|---|---|---|---|
| 43 | 4-{[2-Carboxy-2-(2,4,6-trimethyl-benzenesulfonylamino)-ethyl]carbamoyl]-methoxy}-2-(pyridin-2-ylaminomethyl)-pyrrolidine-1-carboxylic acid hexyl ester | 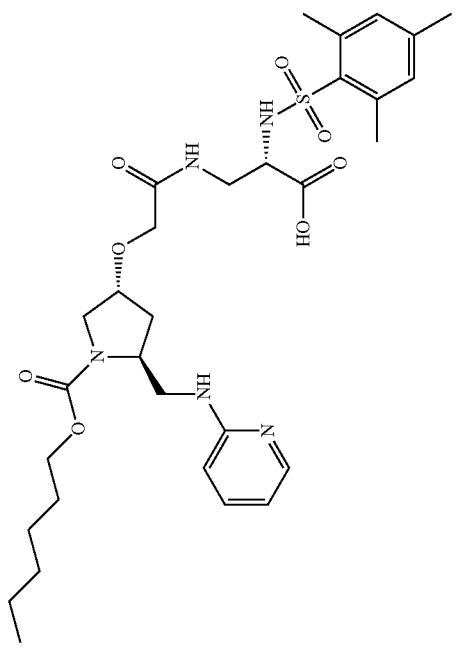 | C31H45N5O8S | 647.78 | Exp. 6A | 648.6 |
| 44 | 4-{[2-Carboxy-2-(2,4,6-trimethyl-benzenesulfonylamino)-ethyl]carbamoyl]-methoxy}-2-(pyridin-2-ylaminomethyl)-pyrrolidine-1-carboxylic acid prop-2-ynyl ester | 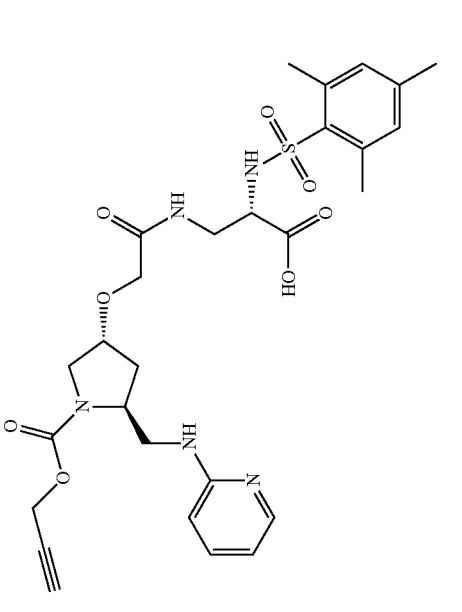 | C28H35N5O8S | 601.67 | Exp. 6A | 602.5 |

TABLE 1-continued

| No. | Structure | Name | Formula | Mol-Weight | Example | LCMS |
|---|---|---|---|---|---|---|
| 45 | 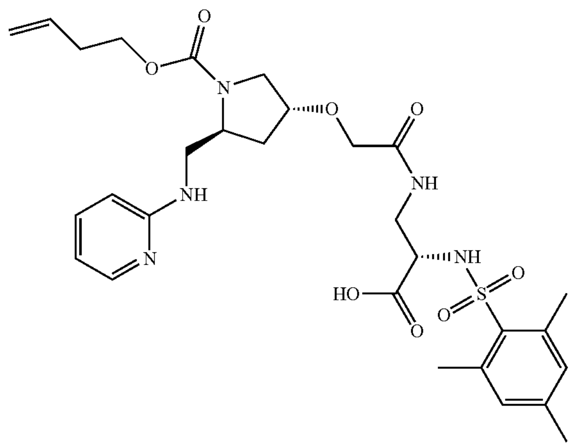 [SMILES: C=CCCOC(=O)N1C[C@H](OCC(=O)NC[C@H](NS(=O)(=O)c2c(C)cc(C)cc2C)C(=O)O)C[C@H]1CNc1ccccn1] | 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid but-3-enyl ester | C29H39N5O8S | 617.71 | Exp. 6A | 618.5 |
| 46 | 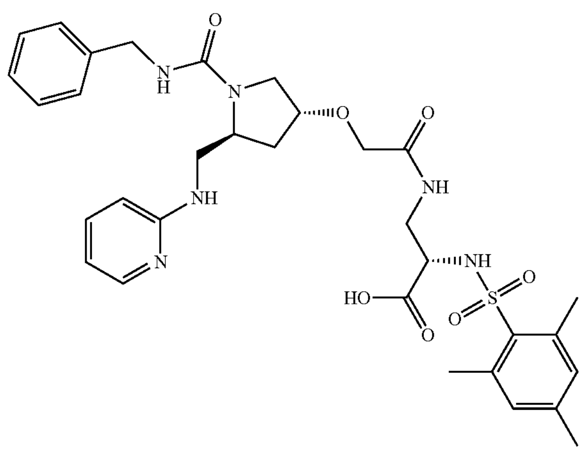 [SMILES: Cc1cc(C)c(S(=O)(=O)N[C@@H](CNC(=O)CO[C@@H]2C[C@@H](CNc3ccccn3)N(C(=O)NCc3ccccc3)C2)C(=O)O)c(C)c1] | 3-{2-[1-Benzylcarbamoyl-5-(pyridin-2-ylaminomethyl)-pyrrolidin-3-yloxy]-acetylamino}-2-(2,4,6-trimethyl-benzenesulfonylamino)-propionic acid | C32H40N6O7S | 652.76 | Exp. 6B | 653.3 |

TABLE 1-continued

| No. | Structure | Name | Formula | Mol-Weight | Example | LCMS |
|---|---|---|---|---|---|---|
| 47 | 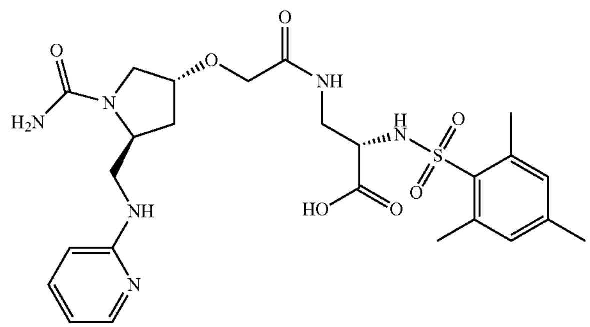 [SMILES: Cc1cc(C)c(S(=O)(=O)N[C@@H](CNC(=O)CO[C@@H]2C[C@@H](CNc3ccccn3)N(C(N)=O)C2)C(=O)O)c(C)c1] | 3-{2-[1-Carbamoyl-5-(pyridin-2-ylaminomethyl)-pyrrolidin-3-yloxy]-acetylamino}-2-(2,4,6-trimethyl-benzenesulfonylamino)-propionic acid | C25H34N6O7S | 562.64 | Exp. 6B | 563.5 |
| 48 | 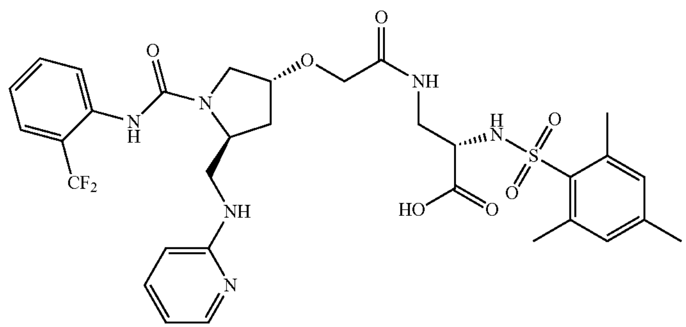 | 3-(2-[5-(Pyridin-2-ylaminomethyl)-1-(2-trifluoromethyl-phenylcarbamoyl)-pyrrolidin-3-yloxy]-acetylamino}-2-(2,4,6-trimethyl-benzeneoulfonylamino)-propionic acid | C32H37F3N6O7S | 706.73 | Exp. 6B | 707.4 |
| 49 | 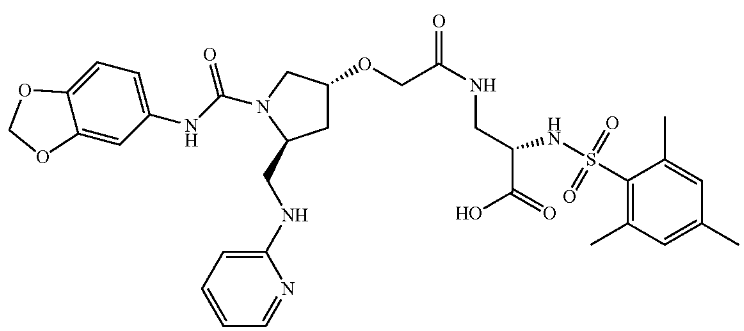 [SMILES: Cc1cc(C)c(S(=O)(=O)N[C@@H](CNC(=O)CO[C@@H]2C[C@@H](CNc3ccccn3)N(C(=O)Nc3ccc4c(c3)OCO4)C2)C(=O)O)c(C)c1] | 3-{2-[1-(Benzo[1,3]dioxol-5-ylcarbamoyl)-5-(pyridin-2-ylaminomethyl)-pyrrolidin-3-yloxy]-acetylamino}-2-(2,4,6-trimethyl-benzenesulfonylamino)-propionic acid | C32H38N6O9S | 682.74 | Exp. 6B | 682.4 |

TABLE 1-continued

| No. | Name | Structure | Formula | Mol-Weight | Example | LCMS |
|---|---|---|---|---|---|---|
| 50 | 3-{2-[1-(Biphenyl-4-ylcarbamoyl)-5-(pyridin-2-ylaminomethyl)-pyrrolidin-3-yloxy]-acetylamino}-2-(2,4,6-trimethyl-benzenesulfonylamino)-propionic acid | 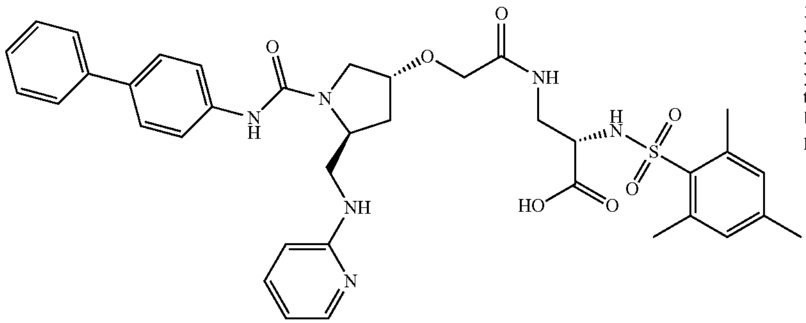 [SMILES: Cc1cc(C)c(S(=O)(=O)N[C@@H](CNC(=O)CO[C@@H]2C[C@@H](CNc3ccccn3)N(C(=O)Nc3ccc(-c4ccccc4)cc3)C2)C(=O)O)c(C)c1] | C37H42N6O7S | 714.83 | Exp. 6B | 715.5 |
| 51 | 3-{2-[1-Benzylthiocarbamoyl-5-(pyridin-2-ylaminomethyl)-pyrrolidin-3-yloxy]-acetylamino}-2-(2,4,6-trimethyl-benzenesulfonylamino)-propionic acid | 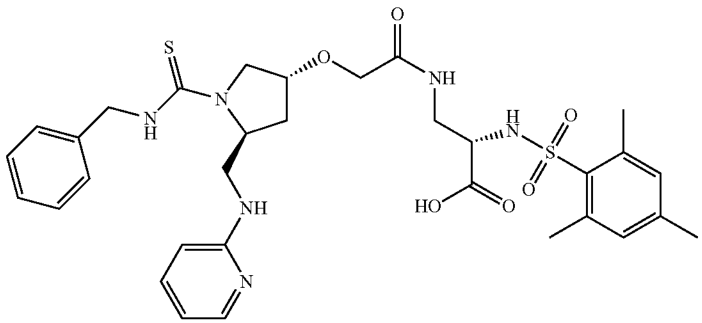 [SMILES: Cc1cc(C)c(S(=O)(=O)N[C@@H](CNC(=O)CO[C@@H]2C[C@@H](CNc3ccccn3)N(C(=S)NCc3ccccc3)C2)C(=O)O)c(C)c1] | C32H40N6O6S2 | 682.85 | Exp. 6P | 683.5 |
| 52 | 3-{2-[1-Acetyl-5-(pyridin-2-ylaminomethyl)-pyrrolidin-3-yloxy]-acetylamino}-2-(2,4,6-trimethyl-benzenesulfonylamino)-propionic acid | 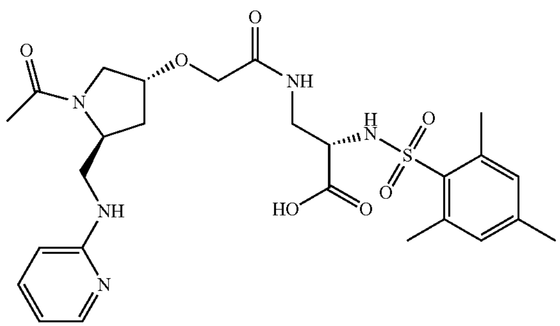 [SMILES: CC(=O)N1C[C@H](OCC(=O)NC[C@H](NS(=O)(=O)c2c(C)cc(C)cc2C)C(=O)O)C[C@H]1CNc1ccccn1] | C26H35N5O7S | 561.65 | Exp. 6A | 562.5 |

TABLE 1-continued

| No. | Structure | Name | Formula | Mol-Weight | Example | LCMS |
|---|---|---|---|---|---|---|
| 53 | 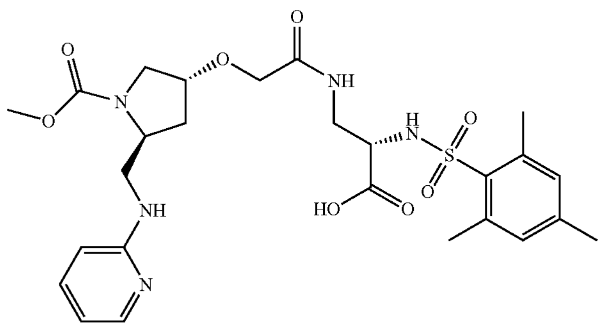 | 4-{[2-carboxy-2-(2,4,6-trimethyl-benzenesulfonylamino)-ethyl]carbamoyl]-methoxy}-2-(pyridin-2-ylaminomethyl)-pyrrolidine-1-carboxylic acid methyl ester | C26H35N5O8S | 577.65 | Exp. 6A | 578.5 |
| 54 | 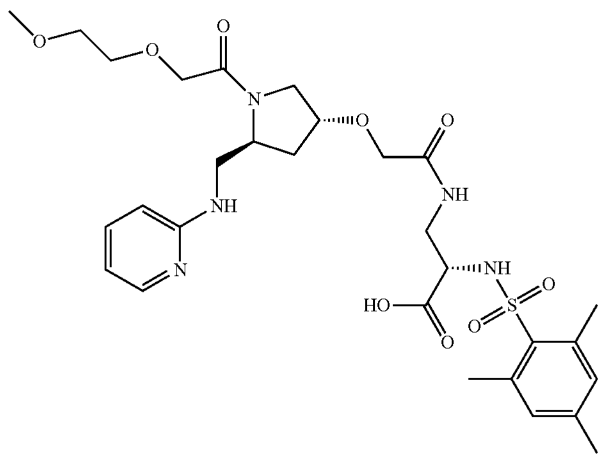 | 3-{2-[1-[2-(2-Methoxy-ethoxy)-acetyl]-5-(pyridin-2-ylaminomethyl)-pyrrolidin-3-yloxy]-acetylamino}-2-(2,4,6-trimethyl-benzenesulfonylamino)-propionic acid | C29H41N5O9S | 635.73 | Exp. 6A | 636.5 |

TABLE 1-continued

| No. | Structure | Name | Formula | Mol-Weight | Example | LCMS |
|---|---|---|---|---|---|---|
| 55 | 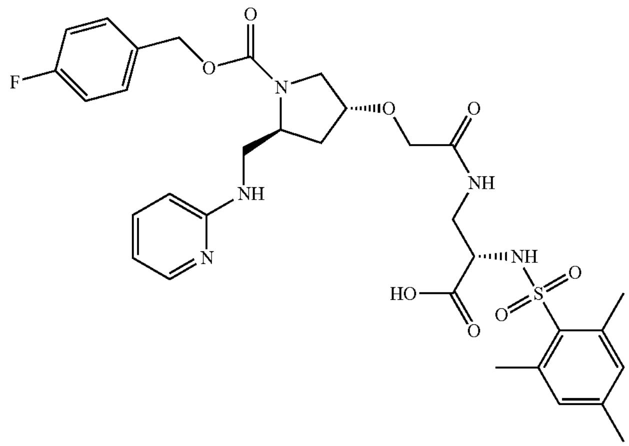 [SMILES: Cc1cc(C)c(S(=O)(=O)N[C@@H](CNC(=O)CO[C@@H]2C[C@@H](CNc3ccccn3)N(C(=O)OCc3ccc(F)cc3)C2)C(=O)O)c(C)c1] | 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid 4-fluoro-benzyl ester | C32H38FN5O8S | 671.74 | Exp. 6A | 672.6 |
| 56 | 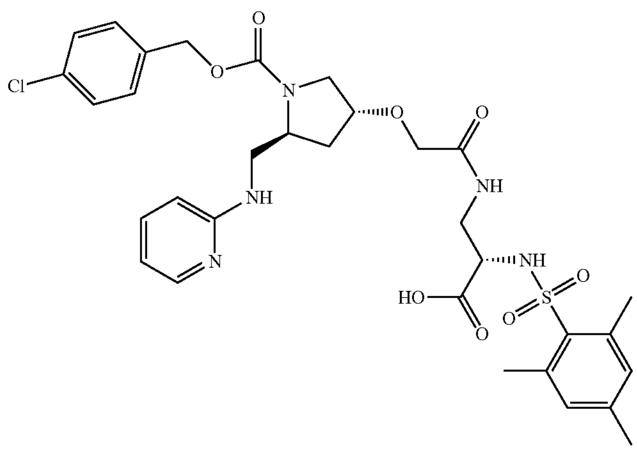 [SMILES: Cc1cc(C)c(S(=O)(=O)N[C@@H](CNC(=O)CO[C@@H]2C[C@@H](CNc3ccccn3)N(C(=O)CCc3ccc(Cl)cc3)C2)C(=O)O)c(C)c1] | 4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acidpbk 4-chloro-benzyl ester | C32H38ClN5O8S | 688.19 | Exp. 6A | 688.7 |

TABLE 1-continued

| No. | Structure | Name | Formula | Mol-Weight | Example | LCMS |
|---|---|---|---|---|---|---|
| 57 | 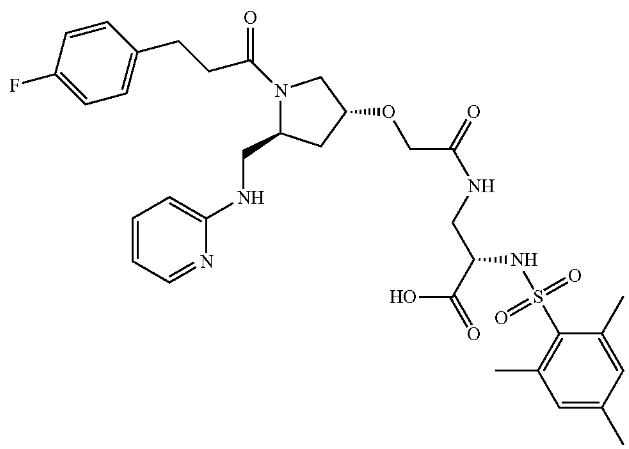 | 3-{2-[1-[3-(4-Fluoro-phenyl)-propionyl]-5-(pyridin-2-ylaminomethyl)-pyrrolidin-3-yloxy]-acetylamino}-2-(2,4,6-trimethyl-benzenesulfonylamino)-propionic acid | C33H40FN5O7S | 669.76 | Exp. 6A | 670.6 |
| 58 | 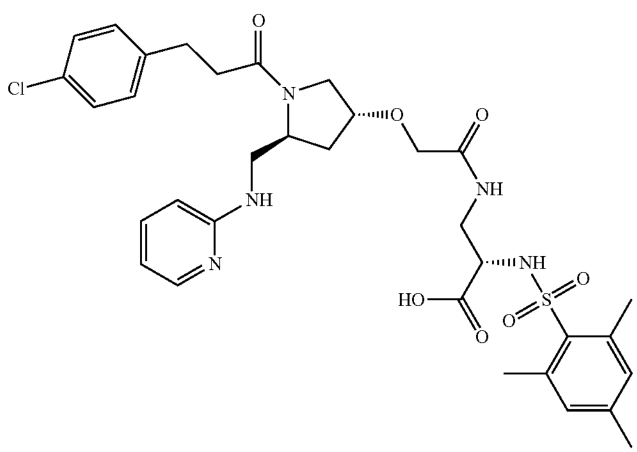 | 3-{2-[1-[3-(4-Chloro-phenyl)-propionyl]-5-(pyridin-2-ylaminomethyl)-pyrrolidin-3-yloxy]-acetylamino}-2-(2,4,6-trimethyl-benzenesulfonylamino)-propionic acid | C33H40ClN5O7S | 686.22 | Exp. 6A | 687.7 |

TABLE 1-continued
| No. | Name | Structure | Formula | Mol-Weight | Example | LCMS |
|---|---|---|---|---|---|---|
| 59 | 4-{[2-Ethoxycarbonyl-2-(2,4,5-trimethyl-benzenesulfonylamino)-ethylcarbamoyl]-methoxy}-2-(pyridin-2-ylaminomethyl)-pyrrolidine-1-carboxylic acid benzyl ester | 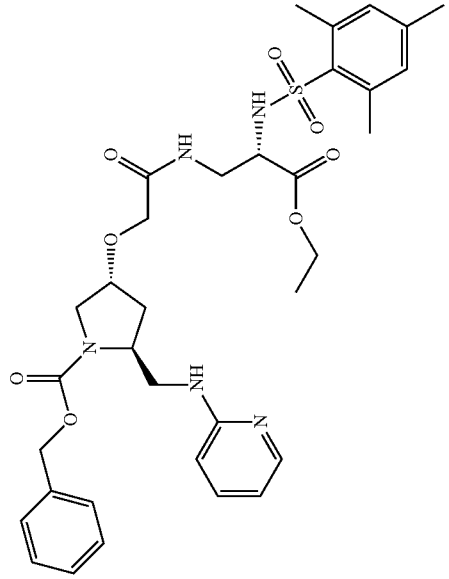 | C34H43N5O8S | 681.80 | Exp. 6A | 682.6 |
| 60 | 3-{2-[1-(3,3-Dimethyl-butyryl)-5-(pyridin-2-ylaminomethyl)-pyrrolidin-3-yloxy]-acetylamino}-2-(2,4,6-trimethyl-benzoylamino)-propionic acid | 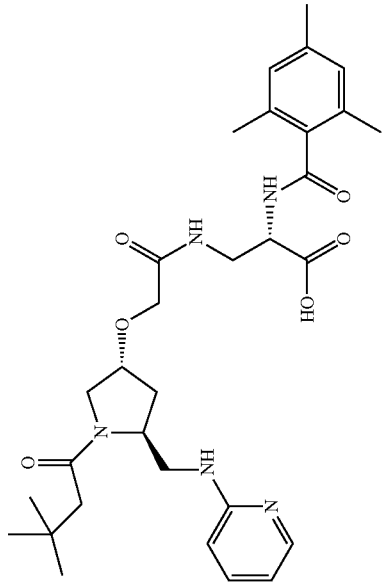 | C31H43N5O6 | 581.70 | Exp. 6A | 582.6 |

TABLE 1-continued

| No. | Structure | Name | Formula | Mol-Weight | Example | LCMS |
|---|---|---|---|---|---|---|
| 61 | 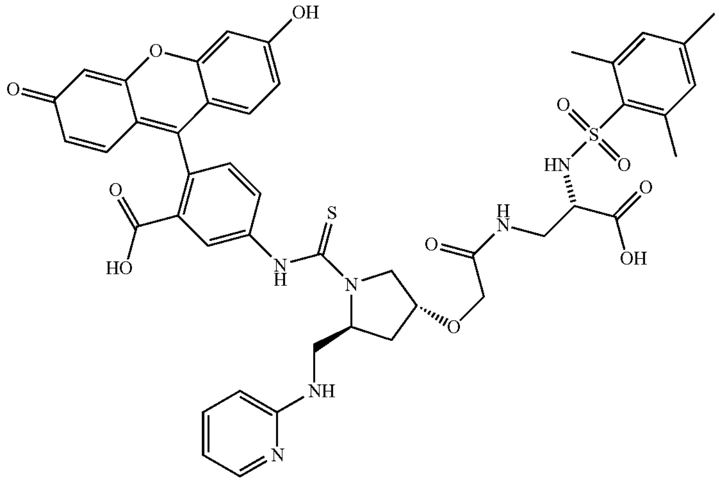 [SMILES: Cc1cc(C)c(S(=O)(=O)N[C@@H](CNC(=O)CO[C@@H]2C[C@@H](CNc3ccccn3)N(C(=S)Nc3ccc(-c4c5ccc(=O)cc-5oc5cc(O)ccc45)c(C(=O)O)c3)C2)C(=O)O)c(C)c1] | 5-[[4-[[2-Carboxy-2-(2,4,6-trimethyl-benzenesulfonyl]amino)-ethyl]carbamoyl]-methoxy}-2-(pyridin-2-ylaminomethyl)-pyrrolidine-1-carbothioyl]-amino}-2-(6-hydroxy-3-oxo-3H-xanthen-9-yl)-benzoic acid | C45H44N6O11S2 | 909.67 | Exp. 8B | 909.4 |
| 62 | 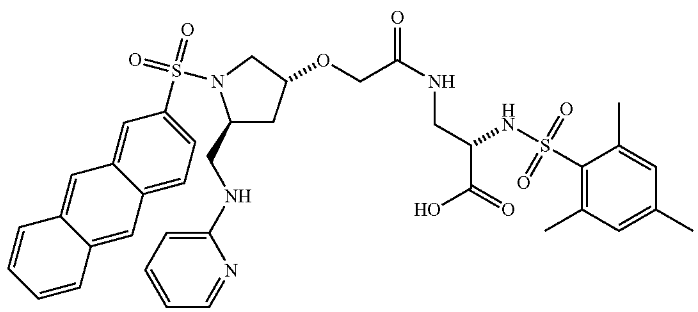 [SMILES: Cc1cc(C)c(S(=O)(=O)N[C@@H](CNC(=O)CO[C@@H]2C[C@@H](CNc3ccccn3)N(S(=O)(=O)c3ccc4cc5ccccc5cc4c3)C2)C(=O)O)c(C)c1] | 3-{2-[1-(Anthracene-2-sulfonyl)-5-(pyridin-2-ylaminomethyl)-pyrrolidin-3-yloxy]-acetylamino}-2-(2,4,6-trimethyl-benzenesulfonyl)amino)-propionic acid | C38H41N5O8S2 | 759.90 | Exp. 8A | 760.8 |

TABLE 1-continued

| No. | Structure | Name | Formula | Mol-Weight | Example | LCMS |
|---|---|---|---|---|---|---|
| 63 | 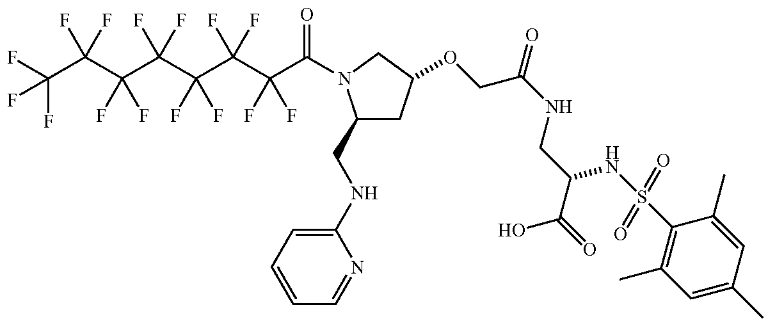 [SMILES: Cc1cc(C)c(S(=O)(=O)N[C@@H](CNC(=O)CO[C@@H]2C[C@@H](CNc3ccccn3)N(C(=O)C(F)(F)C(F)(F)C(F)(F)C(F)(F)C(F)(F)C(F)(F)C(F)(F)F)C2)C(=O)O)c(C)c1] | 3-{2-[1-(2,2,3,3,4,4,5,5,6,6,7,7,8,8,8-Pentadecafluoro-octanoyl)-5-(pyridin-2-ylaminomethyl)-pyrrolidin-3-yloxy]-acetylamino}-2-(2,4,6-trimethyl-benzenesulfonylamino)-propionic acid | C32H32F15N5O7S | 915.68 | Exp. 8A | 916.6 |
| 64 | 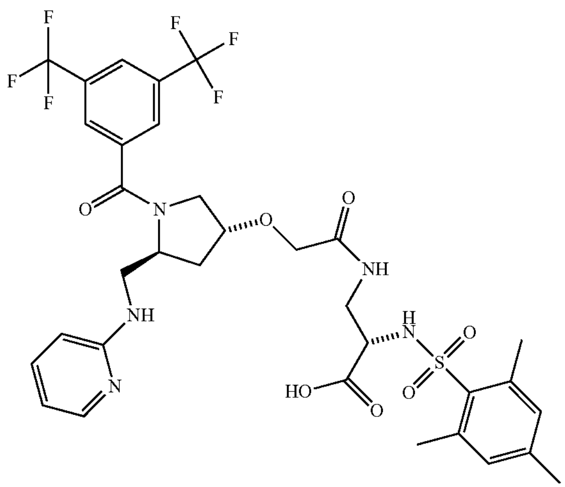 [SMILES: Cc1cc(C)c(S(=O)(=O)N[C@@H](CNC(=O)CO[C@@H]2C[C@@H](CNc3ccccn3)N(C(=O)c3cc(C(F)(F)F)cc(C(F)(F)F)c3)C2)C(=O)O)c(C)c1] | 3-{2-[1-(3,5-Bis-trifluoromethyl-benzoyl)-5-(pyridin-2-ylaminomethyl)-pyrrolidin-3-yloxy]-acetylamino}-2-(2,4,6-trimethyl-benzenesulfonylamino)-propionic acid | C33H35F6N5O7S | 759.73 | Exp. 8A | 760.6 |

TABLE 1-continued

| No. | Structure | Name | Formula | Mol-Weight | Example | LCMS |
|---|---|---|---|---|---|---|
| 65 | 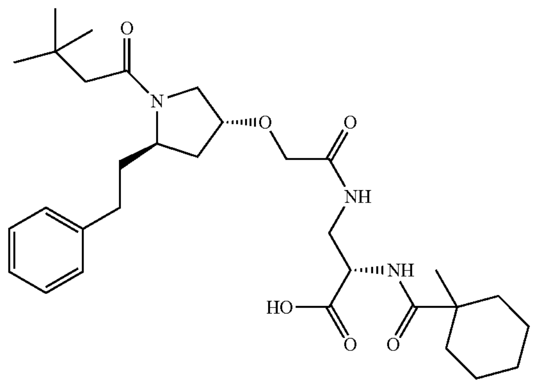 [SMILES: CC(C)(C)CC(=O)N1C[C@H](OCC(=O)NC[C@H](NC(=O)C2(C)CCCCC2)C(=O)O)C[C@H]1CCc1ccccc1] | 3-{2-[1-(3,3-Dimethyl-butyryl)-5-(pyridin-2-ylaminomethyl)-pyrrolidin-3-yloxy]-acetylamino}-2-[(1-methyl-cyclohexanecarbonyl)-amino]-propionic acid | C29H45N5O6 | 559.70 | Exp. 6A | 560 |
| 66 | 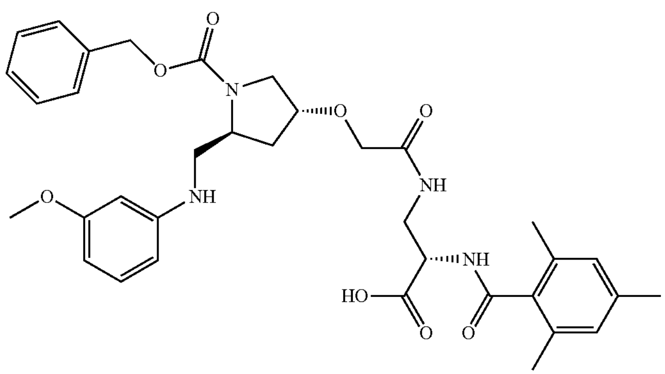 [SMILES: COc1cccc(NC[C@@H]2C[C@@H](OCC(=O)NC[C@H](NC(=O)c3c(C)cc(C)cc3C)C(=O)O)CN2C(=O)OCc2ccccc2)c1] | 4-{[2-Carboxy-2-(2,4,6-trimethyl-benzoylamino)-ethylcarbamoyl]-methoxy}-2-[(4-methoxy-pyridin-2-ylamino)-methyl]-pyrrolidine-1-carboxylic acid benzyl ester | C34H41N5O8 | 647.72 | Exp. 6A | 648.7 |

TABLE 1-continued

| No. | Name | Structure | Formula | Mol-Weight | Example | LCMS |
|---|---|---|---|---|---|---|
| 67 | 4-{[2-(Butane-1-sulfonylamino)-2-carboxy-ethyl]carbamoyl]-methoxy}-2-(pyridin-2-ylaminomethyl)-pyrrolidine-1-carboxylic acid benzyl ester | 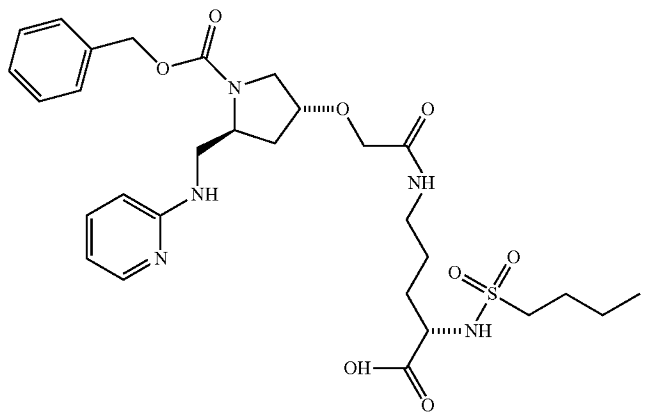 [SMILES: CCCCS(=O)(=O)N[C@@H](CCCNC(=O)CO[C@@H]1C[C@@H](CNc2ccccn2)N(C(=O)OCc2ccccc2)C1)C(=O)O] | C27H37N5O8S | 591.68 | Exp. 8A | 592.3 |
| 68 | 4-[(2-Carboxy-2-phenylmethanesulfonylamino-ethyl)carbamoyl]-methoxy}-2-(pyridin-2-ylaminomethyl)-pyrrolidine-1-carboxylic acid benzyl ester | 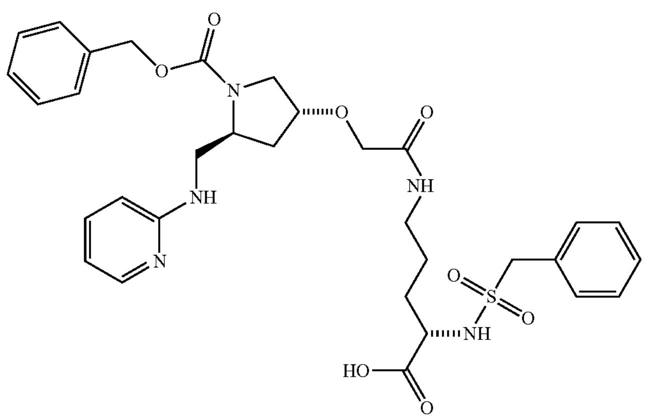 [SMILES: O=C(CO[C@@H]1C[C@@H](CNc2ccccn2)N(C(=O)OCc2ccccc2)C1)NCCC[C@H](NS(=O)(=O)Cc1ccccc1)C(=O)O] | C30H35N5O8S | 625.69 | Exp. 8A | 625.5 |

TABLE 1-continued

| No. | Structure | Name | Formula | Mol-Weight | Example | LCMS |
|---|---|---|---|---|---|---|
| 69 | 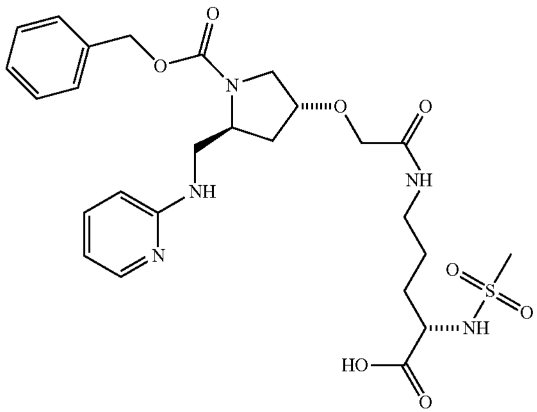 [SMILES: CS(=O)(=O)N[C@@H](CCCNC(=O)CO[C@@H]1C[C@@H](CNc2ccccn2)N(C(=O)OCc2ccccc2)C1)C(=O)O] | 4-[(2-Carboxy-2-methanesulfonylamino-ethylcarbamoyl)-methoxy]-2-(pyridin-2-ylaminomethyl)-pyrrolidine-1-carboxylic acid benzyl ester | C24H31N5O8S | 549.60 | Exp. 8A | 550.4 |
| 70 | 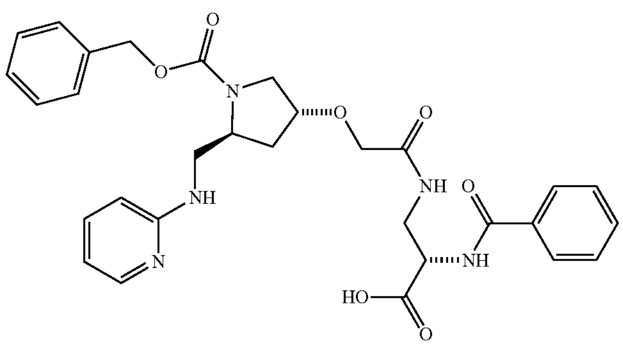 [SMILES: O=C(CO[C@@H]1C[C@@H](CNc2ccccn2)N(C(=O)OCc2ccccc2)C1)NC[C@H](NC(=O)c1ccccc1)C(=O)O] | 4-[(2-Benzoylamino-2-carboxy-ethylcarbamoyl)-methoxy]-2-(pyridin-2-ylaminomethyl)-pyrrolidine-1-carboxylic acid benzyl ester | C30H33N5O7 | 575.62 | Exp. 8A | 576.4 |

TABLE 1-continued

| No. | Structure | Name | Formula | Mol-Weight | Example | LCMS |
|---|---|---|---|---|---|---|
| 71 | 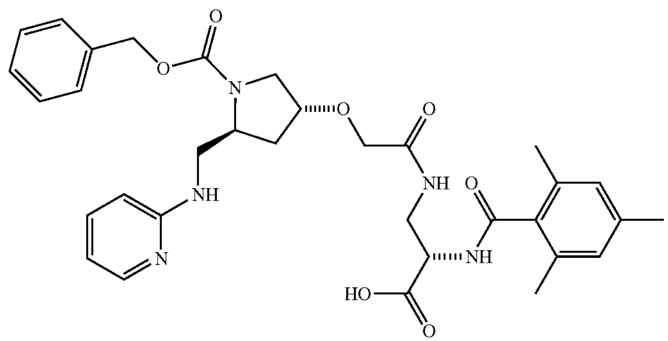 [SMILES: Cc1cc(C)c(C(=O)N[C@@H](CNC(=O)CO[C@@H]2C[C@@H](CNc3ccccn3)N(C(=O)OCc3ccccc3)C2)C(=O)O)c(C)c1] | 4-{[2-Carboxy-2-(2,4,6-trimethyl-benzoylamino)-ethylcarbamoyl]-methoxy}-2-(pyridin-2-ylaminomethyl)-pyrrolidine-1-carboxylic acid benzyl ester | C33H39N5O7 | 617.70 | Exp. 8A | 618.4 |
| 72 | 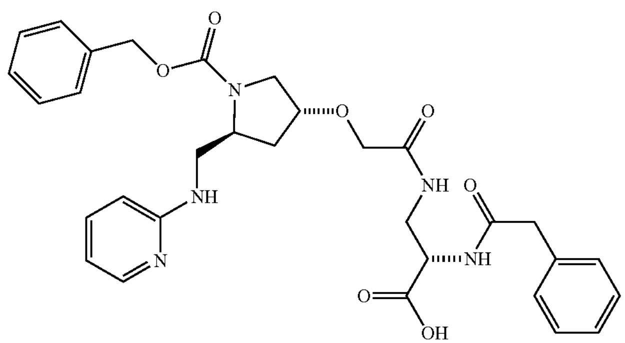 [SMILES: O=C(CO[C@@H]1C[C@@H](CNc2ccccn2)N(C(=O)OCc2ccccc2)C1)NC[C@H](NC(=O)Cc1ccccc1)C(=O)O] | 4-{[2-Carboxy-2-phenylacetylamino-ethylcarbamoyl]-methoxy}-2-(pyridin-2-ylaminomethyl)-pyrrolidine-1-carboxylic acid benzyl ester | C31H35N5O7 | 589.65 | Exp. 8A | 590.5 |
| 73 | 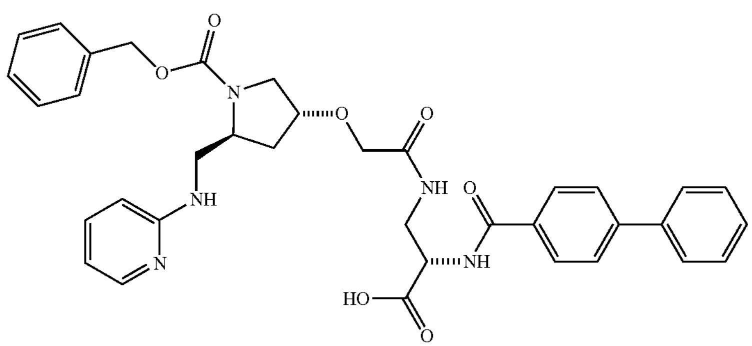 [SMILES: O=C(CO[C@@H]1C[C@@H](CNc2ccccn2)N(C(=O)OCc2ccccc2)C1)NC[C@H](NC(=O)c1ccc(-c2ccccc2)cc1)C(=O)O] | 4-({2-[(Biphenyl-4-carbonyl)-amino]-2-carboxy-ethylcarbamoyl}-methoxy)-2-(pyridin-2-ylaminomethyl)-pyrrolidine-1-carboxylic acid benzyl ester | C36H37N5O7 | 651.72 | Exp. 8A | 652.5 |

TABLE 1-continued

| No. | Structure | Name | Formula | Mol-Weight | Example | LCMS |
|---|---|---|---|---|---|---|
| 74 | 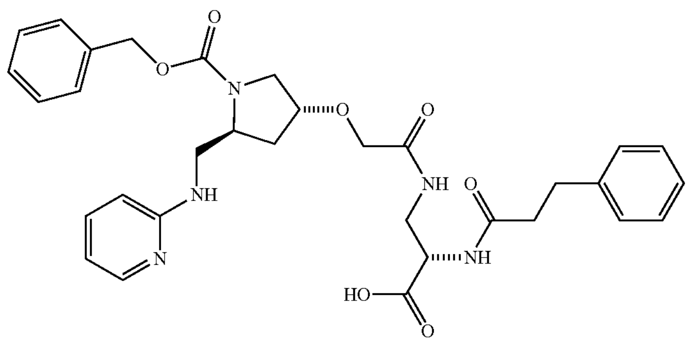 [SMILES: O=C(CO[C@@H]1C[C@@H](CNc2ccccn2)N(C(=O)OCc2ccccc2)C1)NC[C@H](NC(=O)CCc1ccccc1)C(=O)O] | 4-{[2-Carboxy-2-(3-phenyl-propionylamino)-ethylcarbamoyl]-methoxy}-2-(pyridin-2-ylaminomethyl)-pyrrolidine-1-carboxylic acid benzyl ester | C32H37N5O7 | 603.67 | Exp. 8A | 604.5 |
| 75 | 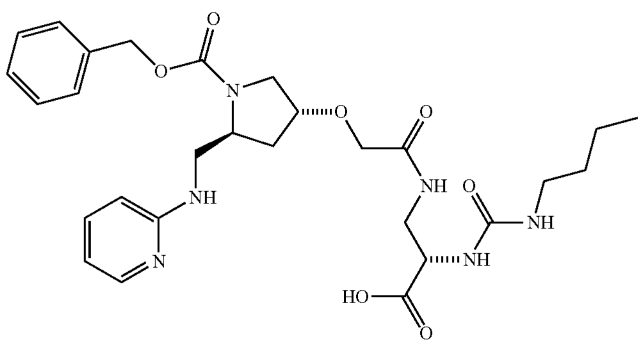 [SMILES: CCCCNC(=O)N[C@@H](CNC(=O)CO[C@@H]1C[C@@H](CNc2ccccn2)N(C(=O)OCc2ccccc2)C1)C(=O)O] | 4-{[2-(3-Butyl-ureido)-2-carboxy-ethylcarbamoyl]-methoxy}-2-(pyridin-2-ylaminomethyl)-pyrrolidine-1-carboxylic acid benzyl ester | C28H38N6O7 | 570.64 | Exp. 8A | 571.4 |
| 76 | 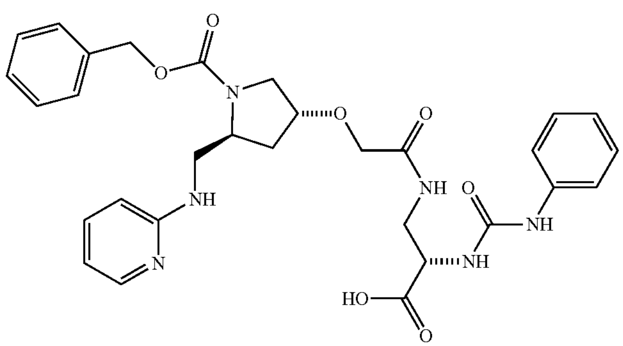 [SMILES: O=C(CO[C@@H]1C[C@@H](CNc2ccccn2)N(C(=O)OCc2ccccc2)C1)NC[C@H](NC(=O)Nc1ccccc1)C(=O)O] | 4-{[2-Carboxy-2-(3-phenyl-ureido)-ethylcarbamoyl]-methoxy}-2-(pyridin-2-ylaminomethyl)-pyrrolidine-1-carboxylic acid benzyl ester | C30H34N6O7 | 590.63 | Exp. 8B | 591.4 |

TABLE 1-continued

| No. | Structure | Name | Formula | Mol-Weight | Example | LCMS |
|---|---|---|---|---|---|---|
| 77 | 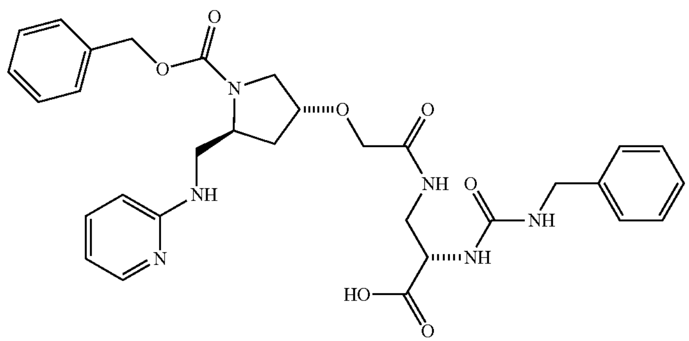 [SMILES: O=C(CO[C@@H]1C[C@@H](CNc2ccccn2)N(C(=O)OCc2ccccc2)C1)NC[C@H](NC(=O)NCc1ccccc1)C(=O)O] | 4-[[2-(3-Benzyl-ureido)-2-carboxy-ethylcarbamoyl]-methoxy]-2-(pyridin-2-ylaminomethyl)-pyrrolidine-1-carboxylic acid benzyl ester | C31H36N6O7 | 604.65 | Exp. 8B | 605.5 |
| 78 | 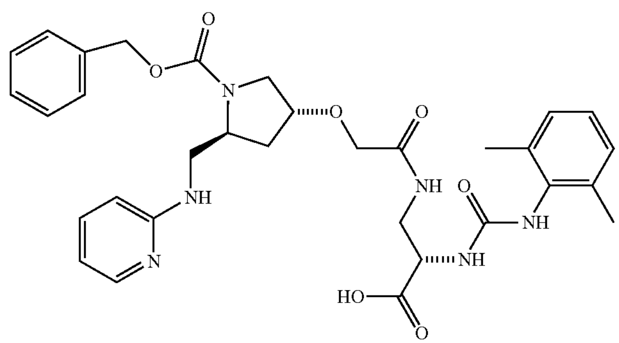 [SMILES: Cc1cccc(C)c1NC(=O)N[C@@H](CNC(=O)CO[C@@H]1C[C@@H](CNc2ccccn2)N(C(=O)OCc2ccccc2)C1)C(=O)O] | 4-({2-Carboxy-2-[3-(2,6-dimethyl-phenyl)-ureido]-ethylcarbamoyl}-methoxy)-2-(pyridin-2-ylaminomethyl)-pyrrolidine-1-carboxylic acid benzyl ester | C32H38N6O7 | 618.69 | Exp. 8B | 619.5 |
| 79 | 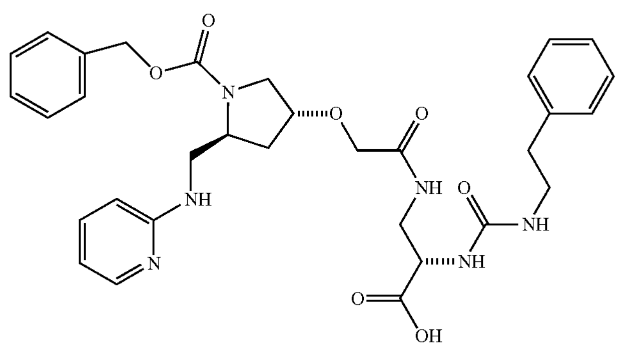 [SMILES: O=C(CO[C@@H]1C[C@@H](CNc2ccccn2)N(C(=O)OCc2ccccc2)C1)NC[C@H](NC(=O)NCCc1ccccc1)C(=O)O] | 4-[[2-Carboxy-2-(3-phenethyl-ureido)-ethylcarbamoyl]-methoxy]-2-(pyridin-2-ylaminomethyl)-pyrrolidine-1-carboxylic acid benzyl ester | C32H38N6O7 | 618.69 | Exp. 8B | 619.5 |

TABLE 1-continued

| No. | Structure | Name | Formula | Mol-Weight | Example | LCMS |
|---|---|---|---|---|---|---|
| 80 | 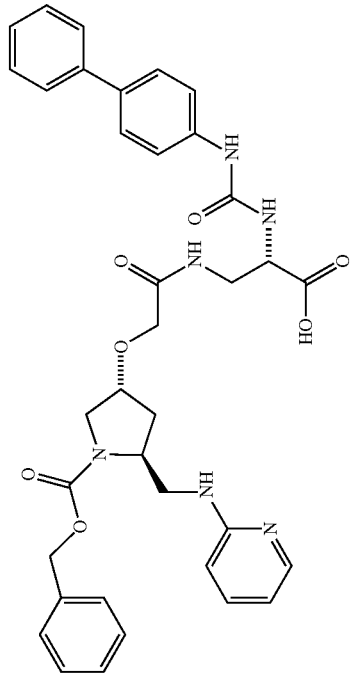 | 4-{[2-(3-Biphenyl-4-yl-ureido)-2-carboxy-ethylcarbamoyl]-methoxy}-2-(pyridin-2-ylaminomethyl)-pyrrolidine-1-carboxylic acid benzyl ester | C36H38N6O7 | 666.72 | Exp. 8B | 667.5 |
| 81 | 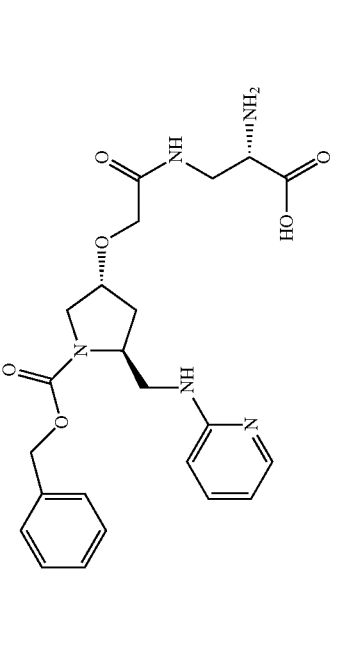 | 4-[(2-Amino-2-carboxy-ethylcarbamoyl)-methoxy]-2-(pyridin-2-ylaminomethyl)-pyrrolidine-1-carboxylic acid benzyl ester | C23H29N5O6 | 471.51 TF | Exp. 8A | 472.3 |
| 82 | 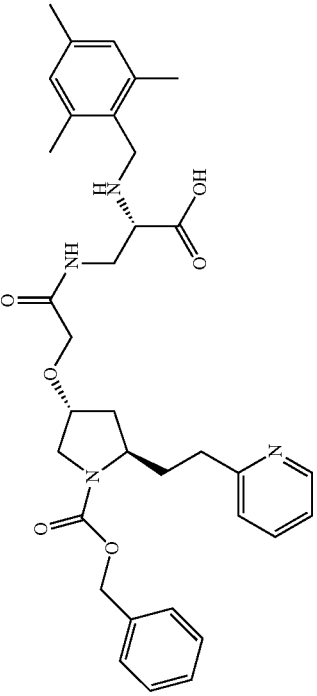 | 4-{[2-Carboxy-2-(2,4,6-trimethyl-benzylamino)-ethylcarbamoyl]-methoxy}-2-(pyridin-2-ylaminomethyl)-pyrrolidine-1-carboxylic acid benzyl ester | C35H42F3N5O8 | 603.71 | Exp. 8C | 604.5 |

TABLE 1-continued

| No. | Structure | Name | Formula | Mol-Weight | Example | LCMS |
|---|---|---|---|---|---|---|
| 83 | 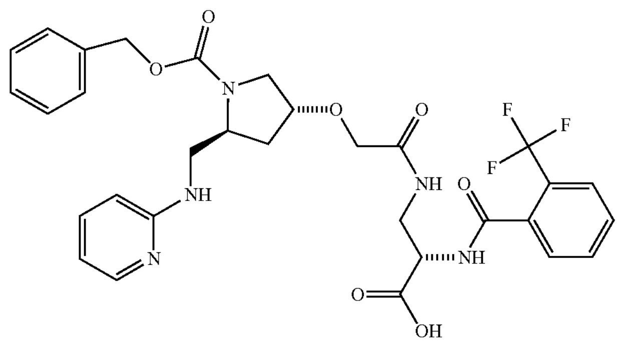 [SMILES: O=C(CO[C@@H]1C[C@@H](CNc2ccccn2)N(C(=O)OCc2ccccc2)C1)NC[C@H](NC(=O)c1ccccc1C(F)(F)F)C(=O)O] | 4-[[2-Carboxy-2-(2-trifluoromethyl-benzoylamino)-ethyl]carbamoyl]-methoxy}-2-(pyridin-2-ylaminomethyl)-pyrrolidine-1-carboxylic acid benzyl ester | C31H32F3N5O7 | 643.62 | Exp. 8A | 644.5 |
| 84 | 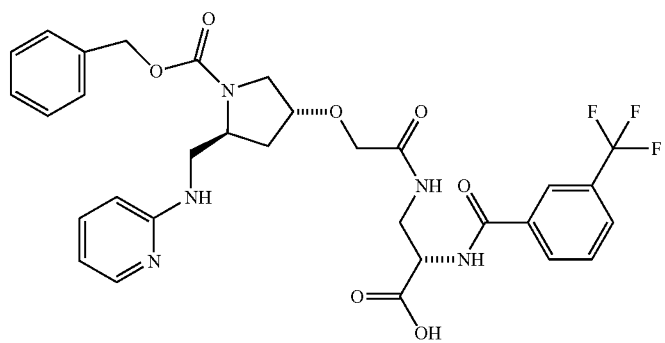 [SMILES: O=C(CO[C@@H]1C[C@@H](CNc2ccccn2)N(C(=O)OCc2ccccc2)C1)NC[C@H](NC(=O)c1cccc(C(F)(F)F)c1)C(=O)O] | 4-[[2-Carboxy-2-(3-trifluoromethyl-benzoylamino)-ethyl]carbamoyl]-methoxy}-2-(pyridin-2-ylaminomethyl)-pyrrolidine-1-carboxylic acid benzyl ester | C31H32F3N5O7 | 643.62 | Exp. 8A | 644.5 |
| 85 | 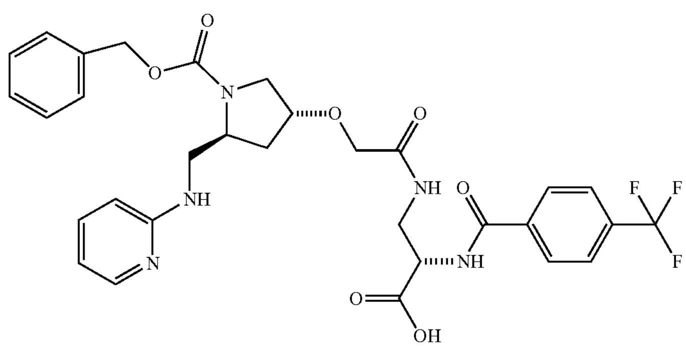 [SMILES: O=C(CO[C@@H]1C[C@@H](CNc2ccccn2)N(C(=O)OCc2ccccc2)C1)NC[C@H](NC(=O)c1ccc(C(F)(F)F)cc1)C(=O)O] | 4-[[2-Carboxy-2-(4-trifluoromethyl-benzoylamino)-ethyl]carbamoyl]-methoxy}-2-(pyridin-2-ylaminomethyl)-pyrrolidine-1-carboxylic acid benzyl ester | C31H32F3N5O7 | 643.62 | Exp. 8A | 644 |

TABLE 1-continued

| No. | Structure | Name | Formula | Mol-Weight | Example | LCMS |
|---|---|---|---|---|---|---|
| 86 | 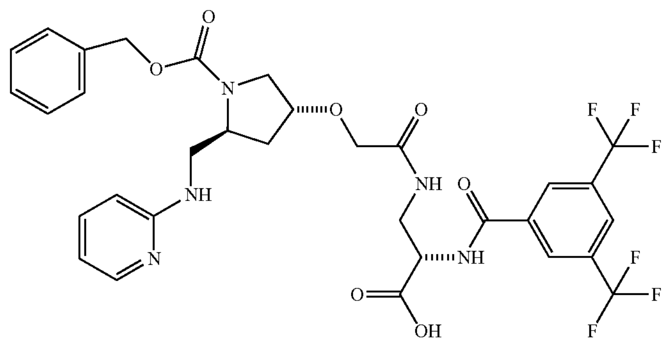 [SMILES: O=C(CO[C@@H]1C[C@@H](CNc2ccccn2)N(C(=O)OCc2ccccc2)C1)NC[C@H](NC(=O)c1cc(C(F)(F)F)cc(C(F)(F)F)c1)C(=O)O] | 4-{[2-(3,5-Bis-trifluoromethyl-benzoylamino)-2-carboxy-ethylcarbamoyl]-methoxy}-2-(pyridin-2-ylaminomethyl)-pyrrolidine-1-carboxylic acid benzyl ester | C32H31F6N5O7 | 711.62 | Exp. 8A | 712.5 |
| 87 | 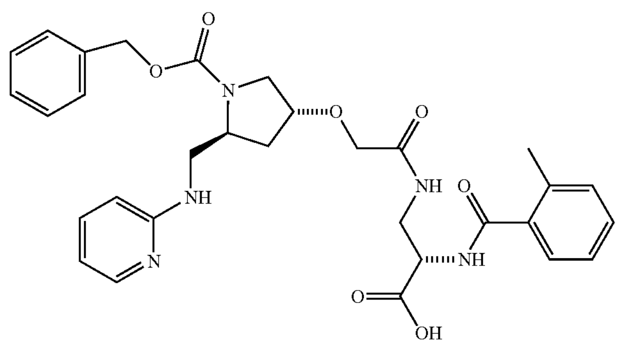 [SMILES: Cc1ccccc1C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2-methyl-benzoylamino)-ethylcarbamoyl]-methoxy}-2-(pyridin-2-ylaminomethyl)-pyrrolidine-1-carboxylic acid benzyl ester | C31H35N5O7 | 589.65 | Exp. 8A | 590.5 |
| 88 | 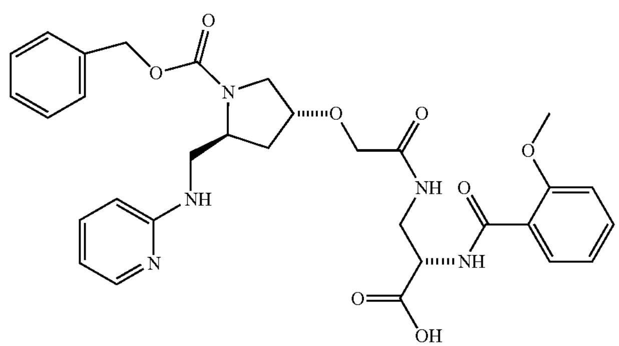 [SMILES: COc1ccccc1C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2-methoxy-benzoylamino)-ethylcarbamoyl]-methoxy}-2-(pyridin-2-ylaminomethyl)-pyrrolidine-1-carboxylic acid benzyl ester | C31H35N5O8 | 605.65 | Exp. 8A | 606.5 |

TABLE 1-continued

| No. | Structure | Name | Formula | Mol-Weight | Example | LCMS |
|---|---|---|---|---|---|---|
| 89 | 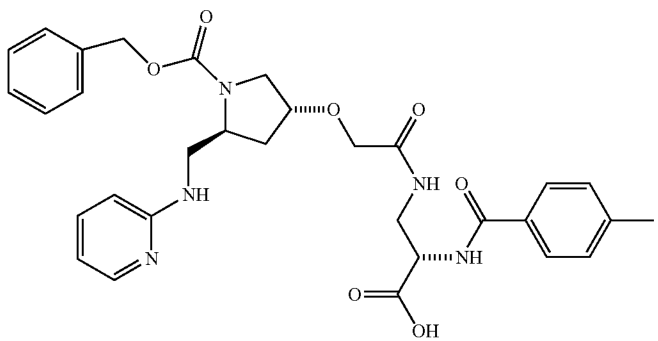 [SMILES: Cc1ccc(C(=O)N[C@@H](CNC(=O)CO[C@@H]2C[C@@H](CNc3ccccn3)N(C(=O)OCc3ccccc3)C2)C(=O)O)cc1] | 4-{[2-Carboxy-2-(4-methyl-benzoylamino)-ethylcarbamoyl]-methoxy}-2-(pyridin-2-ylaminomethyl)-pyrrolidine-1-carboxylic acid benzyl ester | C31H35N5O7 | 589.65 | Exp. 8A | 590 |
| 90 | 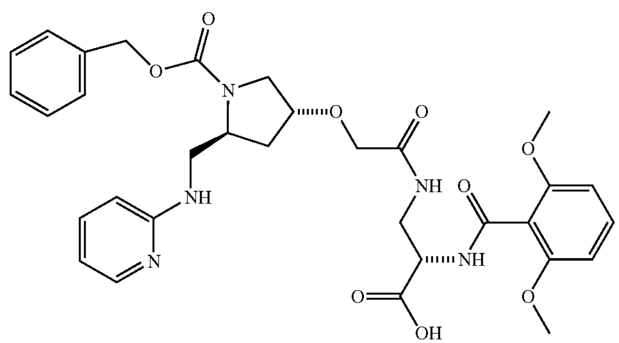 [SMILES: COc1cccc(OC)c1C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2,6-dimethoxy-benzoylamino)-ethylcarbamoyl]-methoxy}-2-(pyridin-2-ylaminomethyl)-pyrrolidine-1-carboxylic acid benzyl ester | C32H37N5O9 | 635.67 | Exp. 8A | 636.5 |
| 91 | 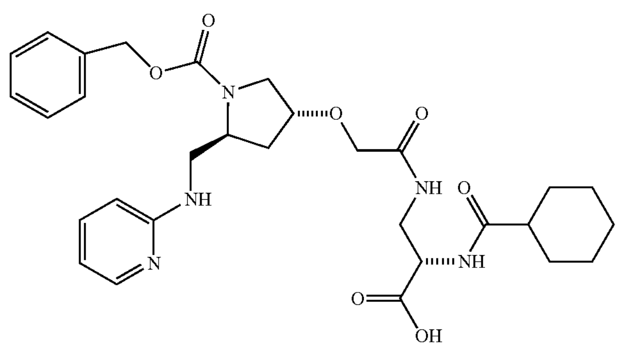 [SMILES: O=C(CO[C@@H]1C[C@@H](CNc2ccccn2)N(C(=O)OCc2ccccc2)C1)NC[C@H](NC(=O)C1CCCCC1)C(=O)O] | 4-{[2-Carboxy-2-(cyclohexanecarbonyl-amino)-ethylcarbamoyl]-methoxy}-2-(pyridin-2-ylaminomethyl)-pyrrolidine-1-carboxylic acid benzyl ester | C30H39N5O7 | 581.67 | Exp. 8A | 582.5 |

TABLE 1-continued

| No. | Structure | Name | Formula | Mol-Weight | Example | LCMS |
|---|---|---|---|---|---|---|
| 92 | 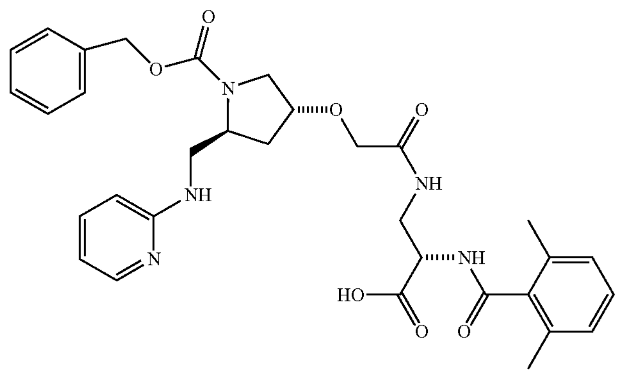 [SMILES: Cc1cccc(C)c1C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2,6-dimethyl-benzoylamino)-ethylcarbamoyl]-methoxy}-2-(pyridin-2-ylaminomethyl)-pyrrolidine-1-carboxylic acid benzyl ester | C32H37N5O7 | 603.67 | Exp. 8A | 504.5 |
| 93 | 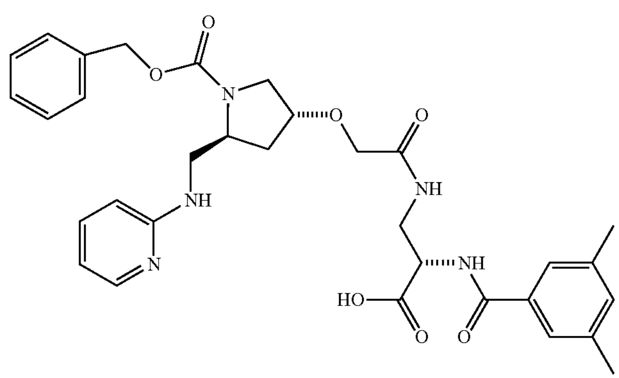 [SMILES: Cc1cc(C)cc(C(=O)N[C@@H](CNC(=O)CO[C@@H]2C[C@@H](CNc3ccccn3)N(C(=O)OCc3ccccc3)C2)C(=O)O)c1] | 4-{[2-Carboxy-2-(3,5-dimethyl-benzoylamino)-ethylcarbamoyl]-methoxy}-2-(pyridin-2-ylaminomethyl)-pyrrolidine-1-carboxylic acid benzyl ester | C32H37N5O7 | 603.67 | Exp. 8A | 604.5 |

TABLE 1-continued

| No. | Name | Structure | Formula | Mol-Weight | Example | LCMS |
|---|---|---|---|---|---|---|
| 94 | 4-{[2-Carboxy-2-(3,4,5-trimethoxy-benzoylamino)-ethylcarbamoyl]-methoxy}-2-(pyridin-2-ylaminomethyl)-pyrrolidine-1-carboxylic acid benzyl ester | 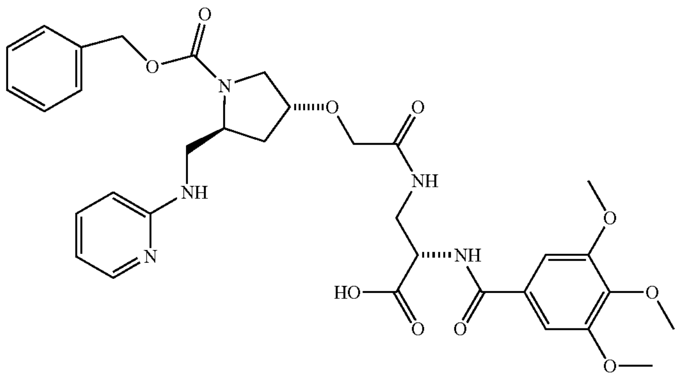 [SMILES: COc1cc(C(=O)N[C@@H](CNC(=O)CO[C@@H]2C[C@@H](CNc3ccccn3)N(C(=O)OCc3ccccc3)C2)C(=O)O)cc(OC)c1OC] | C33H39N5O10 | 665.69 | Exp. 8A | 666.5 |
| 95 | 4-{[2-Carboxy-2-(2-fluoro-benzoylamino)-ethylcarbamoyl]-methoxy}-2-(pyridin-2-ylaminomethyl)-pyrrolidine-1-carboxylic acid benzyl ester | 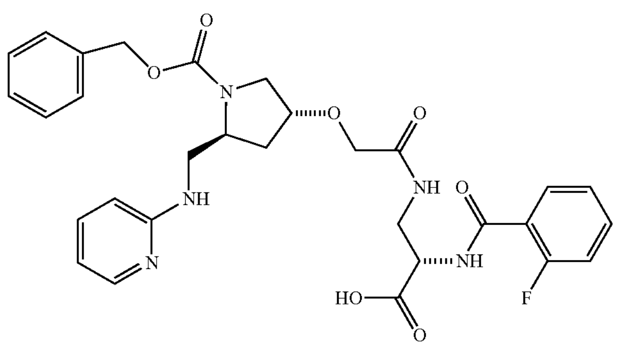 [SMILES: O=C(CO[C@@H]1C[C@@H](CNc2ccccn2)N(C(=O)OCc2ccccc2)C1)NC[C@H](NC(=O)c1ccccc1F)C(=O)O] | C30H32FN5O7 | 593.61 | Exp. 8A | 594.5 |

TABLE 1-continued

| No. | Structure | Name | Formula | Mol-Weight | Example | LCMS |
|---|---|---|---|---|---|---|
| 96 | 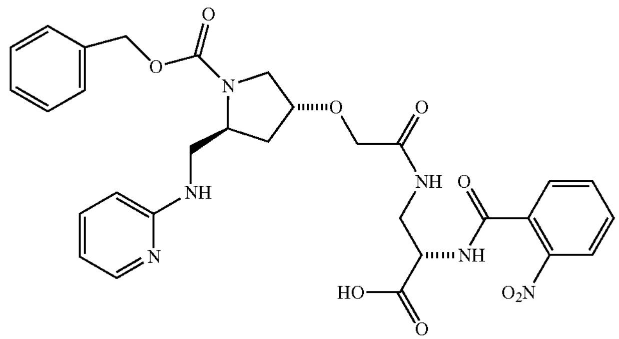 [SMILES: O=C(CO[C@@H]1C[C@@H](CNc2ccccn2)N(C(=O)OCc2ccccc2)C1)NC[C@H](NC(=O)c1ccccc1[N+](=O)[O-])C(=O)O] | 4-{[2-Carboxy-2-(2-nitro-benzoylamino)-ethylcarbamoyl]-methoxy}-2-(pyridin-2-ylaminomethyl)-pyrrolidine-1-carboxylic acid benzyl ester | C30H32N6O9 | 620.62 | Exp. 8A | 621.4 |
| 97 | 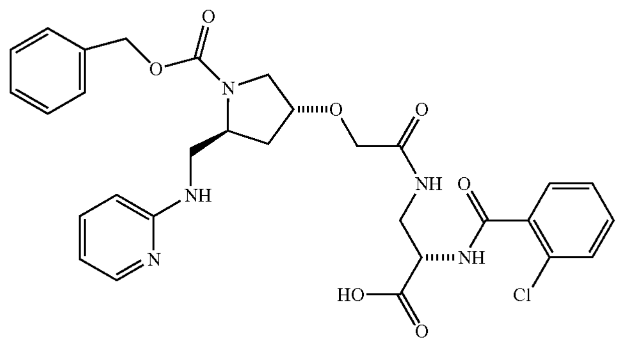 [SMILES: O=C(CO[C@@H]1C[C@@H](CNc2ccccn2)N(C(=O)OCc2ccccc2)C1)NC[C@H](NC(=O)c1ccccc1Cl)C(=O)O] | 4-{[2-Carboxy-2-(2-chloro-benzoylamino)-ethylcarbamoyl]-methoxyl-2-(pyridin-2-ylaminomethyl)-pyrrolidine-1-carboxylic acid benzyl ester | C30H32ClN5O7 | 610.06 | Exp. 8A | 610 |
| 98 | 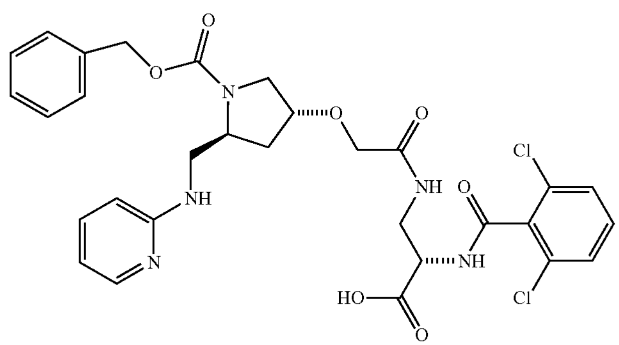 [SMILES: O=C(CO[C@@H]1C[C@@H](CNc2ccccn2)N(C(=O)OCc2ccccc2)C1)NC[C@H](NC(=O)c1c(Cl)cccc1Cl)C(=O)O] | 4-{[2-Carboxy-2-(2,6-dichloro-benzoylamino)-ethylcarbamoyl]-methoxy}-2-(pyridin-2-ylaminomethyl)-pyrrolidine-1-carboxylic acid benzyl ester | C30H31Cl2N5O7 | 644.51 | Exp. 8A | 644.2 |

TABLE 1-continued

| No. | Structure | Name | Formula | Mol-Weight | Example | LCMS |
|---|---|---|---|---|---|---|
| 99 | 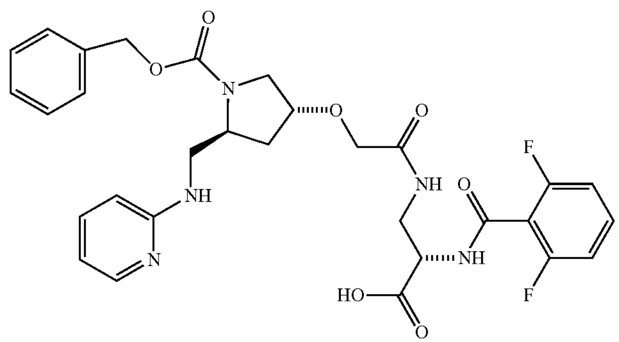 [SMILES: O=C(CO[C@@H]1C[C@@H](CNc2ccccn2)N(C(=O)OCc2ccccc2)C1)NC[C@H](NC(=O)c1c(F)cccc1F)C(=O)O] | 4-{[2-Carboxy-2-(2,6-difluoro-benzoylamino)-ethylcarbamoyl]-methoxy}-2-(pyridin-2-ylaminomethyl)-pyrrolidine-1-carboxylic acid benzyl ester | C30H31F2N5O7 | 611.60 | Exp. 8A | 612.3 |
| 100 | 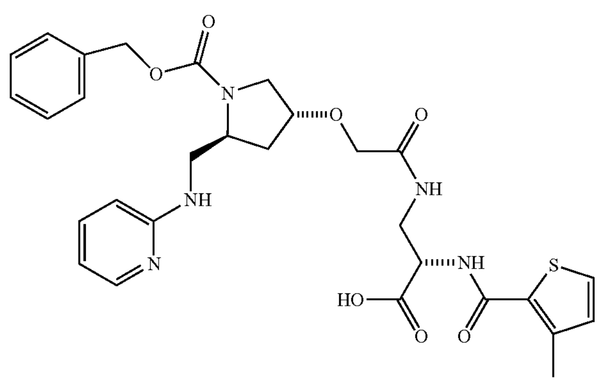 [SMILES: Cc1ccsc1C(=O)N[C@@H](CNC(=O)CO[C@@H]1C[C@@H](CNc2ccccn2)N(C(=O)OCc2ccccc2)C1)C(=O)O] | 4-({2-Carboxy-2-[(3-methyl-thiophene-2-carbonyl)-amino]-ethylcarbamoyl}-methoxy)-2-(pyridin-2-ylaminomethyl)-pyrrolidine-1-carboxylic acid benzyl ester | C29H33N5O7S | 595.66 | Exp. 8A | 596.4 |

TABLE 1-continued

| No. | Name | Structure | Formula | Mol-Weight | Example | LCMS |
|---|---|---|---|---|---|---|
| 101 | 4-({2-Carboxy-2-[(1-methyl-cyclohexanecarbonyl)-amino]-ethylcarbamoyl}-methoxy)-2-(pyridin-2-ylaminomethyl)-pyrrolidine-1-carboxylic acid benzyl ester | 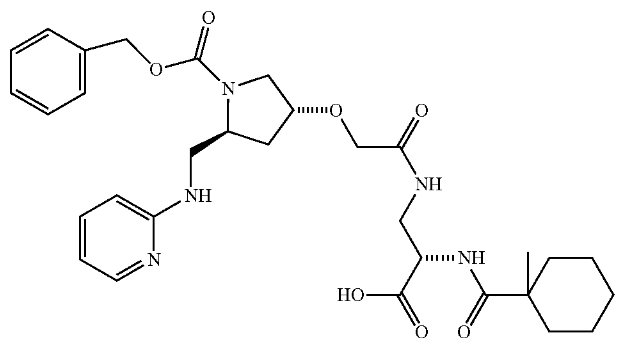 [SMILES: CC1(C(=O)N[C@@H](CNC(=O)CO[C@@H]2C[C@@H](CNc3ccccn3)N(C(=O)OCc3ccccc3)C2)C(=O)O)CCCCC1] | C31H41N5O7 | 595.69 | Exp. 8A | 596 |
| 102 | 4-{[2-Carboxy-2-(3-methyl-2-phenyl-butyrylamino)-ethylcarbamoyl]-methoxy}-2-(pyridin-2-ylaminomethyl)-pyrrolidine-1-carboxylic acid benzyl ester | 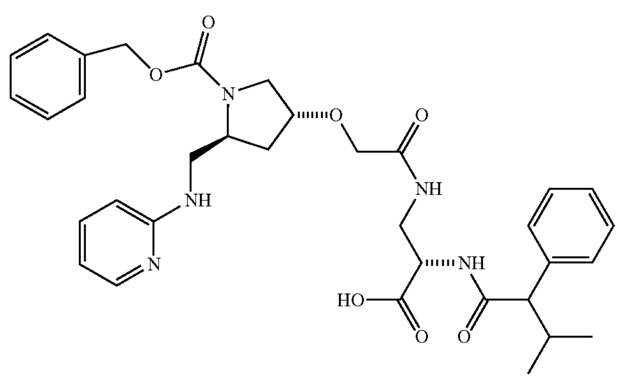 [SMILES: CC(C)C(C(=O)N[C@@H](CNC(=O)CO[C@@H]1C[C@@H](CNc2ccccn2)N(C(=O)OCc2ccccc2)C1)C(=O)O)c1ccccc1] | C34H41N5O7 | 631.72 | Exp. 8A | 622.7 |

TABLE 1-continued

| No. | Structure | Name | Formula | Mol-Weight | Example | LCMS |
|---|---|---|---|---|---|---|
| 103 | 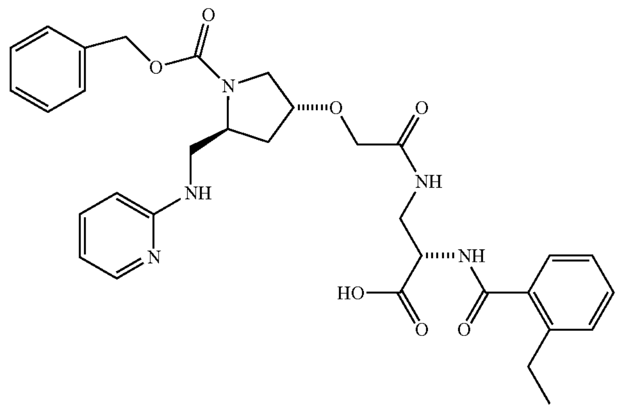 | 4-{[2-Carboxy-2-(2-ethyl-benzoylamino)-ethylcarbamoyl]-methoxy}-2-(pyridin-2-ylaminomethyl)-pyrrolidine-1-carboxylic acid benzyl ester | C32H37N5O7 | 603.67 | Exp. 8A | 604.5 |
| 104 | 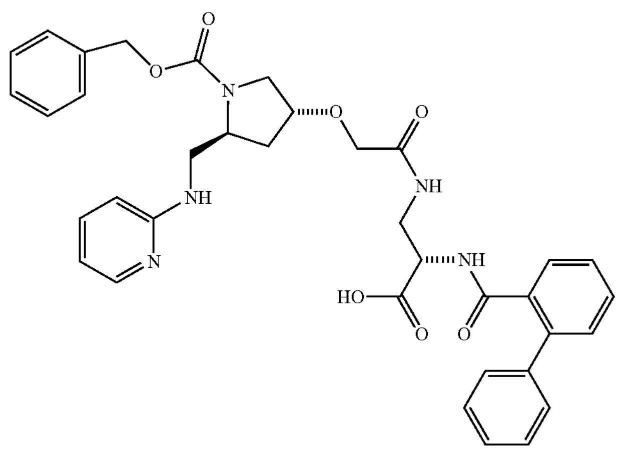 [SMILES: O=C(CO[C@@H]1C[C@@H](CNc2ccccn2)N(C(=O)OCc2ccccc2)C1)NC[C@H](NC(=O)c1ccccc1-c1ccccc1)C(=O)O] | 4-({2-[(Biphenyl-2-carbonyl)-amino]-2-carboxy-ethylcarbamoyl}-methoxy)-2-(pyridin-2-ylaminomethyl)-pyrrolidine-1-carboxylic acid benzyl ester | C36H37N5O7 | 651.71 | Exp. 8A | 652.6 |

TABLE 1-continued

| No. | Name | Structure | Formula | Mol-Weight | Example | LCMS |
|---|---|---|---|---|---|---|
| 105 | 4-({2-Carboxy-2-[(2-methyl-cyclohexanecarbonyl)-amino]-ethylcarbamoyl}-methoxy)-2-(pyridin-2-ylaminomethyl)-pyrrolidine-1-carboxylic acid benzyl ester | 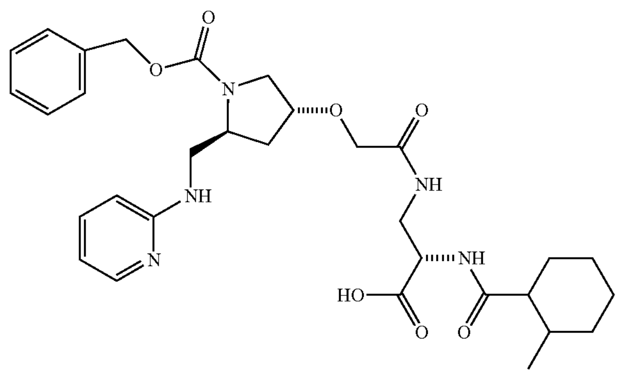 [SMILES: CC1CCCCC1C(=O)N[C@@H](CNC(=O)CO[C@@H]1C[C@@H](CNc2ccccn2)N(C(=O)OCc2ccccc2)C1)C(=O)O] | C31H41N5O7 | 595.69 | Exp. 8A | 596.6 |
| 106 | 4-({2-Carboxy-2-[(1-phenyl-cyclopropanecarbonyl)-amino]-ethylcarbamoyl}-methoxy)-2-(pyridin-2-ylaminomethyl)-pyrrolidine-1-carboxylic acid benzyl ester | 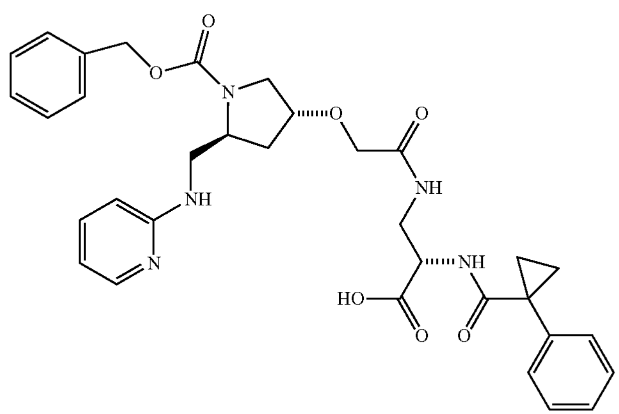 [SMILES: O=C(CO[C@@H]1C[C@@H](CNc2ccccn2)N(C(=O)OCc2ccccc2)C1)NC[C@H](NC(=O)C1(c2ccccc2)CC1)C(=O)O] | C33H37N5O7 | 615.68 | Exp. 8A | 616.6 |

TABLE 1-continued

| No. | Name | Structure | Formula | Mol-Weight | Example | LCMS |
|---|---|---|---|---|---|---|
| 107 | 4-({2-Carboxy-2-[(1-phenyl-cyclopentanecarbonyl)-amino]-ethylcarbamoyl}-methoxy)-2-(pyridin-2-ylaminomethyl)-pyrrolidine-1-carboxylic acid benzyl ester | 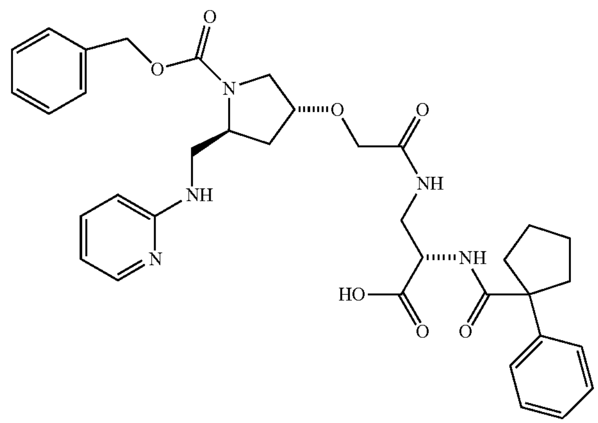 [SMILES: O=C(CO[C@@H]1C[C@@H](CNc2ccccn2)N(C(=O)OCc2ccccc2)C1)NC[C@H](NC(=O)C1(c2ccccc2)CCCC1)C(=O)O] | C35H41N5O7 | 643.73 | Exp. 8A | 644.6 |
| 108 | 4-{[2-Carboxy-2-(2,2-dicyclohexyl-acetylamino)-ethylcarbamoyl]-methoxy}-2-(pyridin-2-ylaminomethyl)-pyrrolidine-1-carboxylic acid benzyl ester | 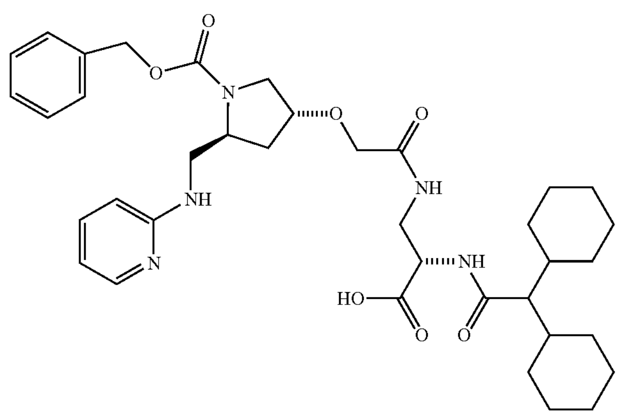 [SMILES: O=C(CO[C@@H]1C[C@@H](CNc2ccccn2)N(C(=O)OCc2ccccc2)C1)NC[C@H](NC(=O)C(C1CCCCC1)C1CCCCC1)C(=O)O] | C37H51N5O7 | 677.83 | Exp. 8A | 678.3 |

TABLE 1-continued

| No. | Structure | Name | Formula | Mol-Weight | Example | LCMS |
|---|---|---|---|---|---|---|
| 109 | 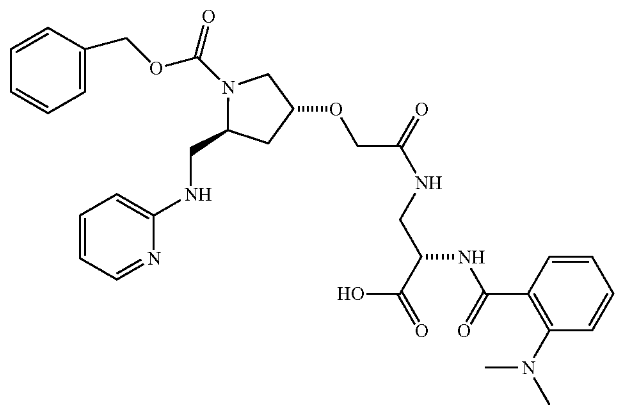 [SMILES: CN(C)c1ccccc1C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2-dimethylamino-benzoylamino)-ethylcarbamoyl]-methoxy}-2-(pyridin-2-ylaminomethyl)-pyrrolidine-1-carboxylic acid benzyl ester | C32H38N6O7 | 518.68 | Exp. 8A | 619.4 |
| 110 | 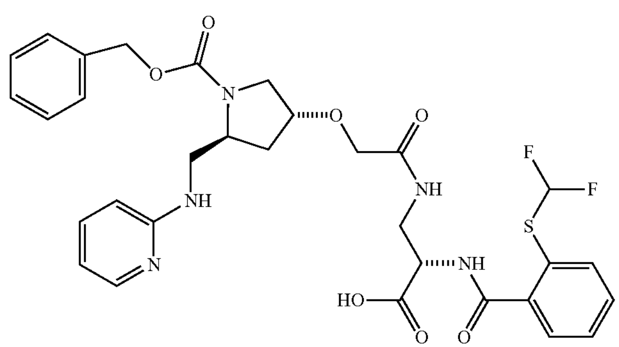 [SMILES: O=C(CO[C@@H]1C[C@@H](CNc2ccccn2)N(C(=O)OCc2ccccc2)C1)NC[C@H](NC(=O)c1ccccc1SC(F)F)C(=O)O] | 4-{[2-Carboxy-2-(2-difluoromethylsulfanyl-benzoylamino)-ethylcarbamoyl]-methoxy}-2-(pyridin-2-ylaminomethyl)-pyrrolidine-1-carboxylic acid benzyl ester | C31H33F2N5O7S | 657.69 | Exp. 8A | 658.5 |

TABLE 1-continued

| No. | Structure | Name | Formula | Mol-Weight | Example | LCMS |
|---|---|---|---|---|---|---|
| 111 | 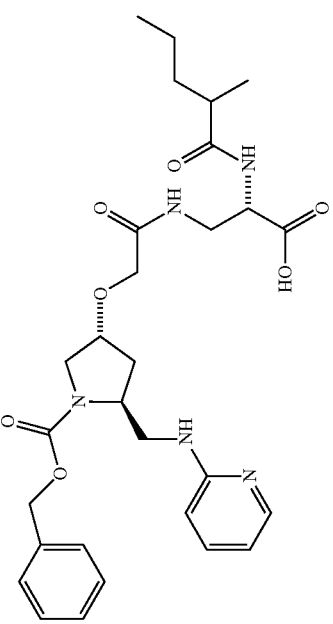 | 4-{[2-Carboxy-2-(2-methyl-pentanoylamino)-ethyl]carbamoyl]-methoxy}-2-(pyridin-2-ylaminomethyl)-pyrrolidine-1-carboxylic acid benzyl ester | C29H39N5O7 | 569.58 | Exp. 8A | 570.5 |
| 112 | 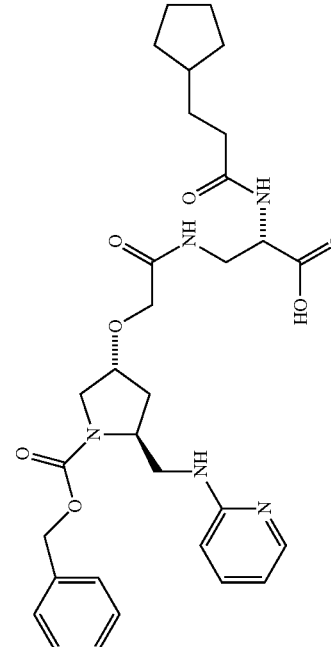 | 4-{[2-Carboxy-2-(3-cyclopentyl-propionylamino)-ethyl]carbamoyl]-methoxy}-2-(pyridin-2-ylaminomethyl)-pyrrolidine-1-carboxylic acid benzyl ester | C31H41N5O7 | 595.69 | Exp. 8A | 595.6 |
| 113 | 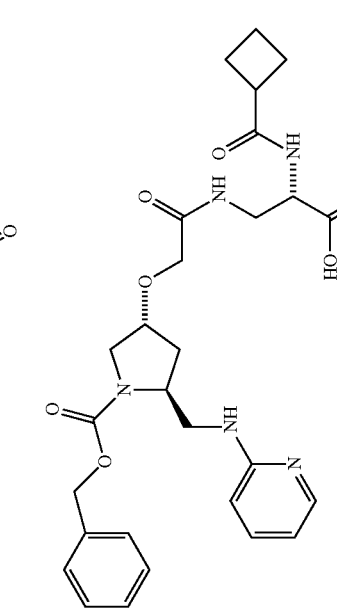 | 4-{[2-Carboxy-2-(cyclobutanecarbonyl-amino)-ethyl]carbamoyl]-methoxy}-2-(pyridin-2-ylaminomethyl)-pyrrolidine-1-carboxylic acid benzyl ester | C28H35N5O7 | 553.61 | Exp. 8A | 554.5 |

TABLE 1-continued

| No. | Structure | Name | Formula | Mol-Weight | Example | LCMS |
|---|---|---|---|---|---|---|
| 114 | 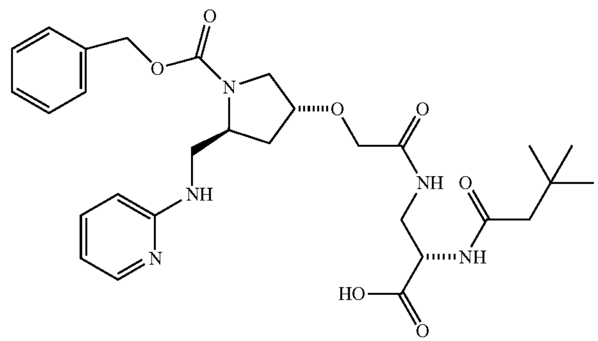 [SMILES: CC(C)(C)CC(=O)N[C@@H](CNC(=O)CO[C@@H]1C[C@@H](CNc2ccccn2)N(C(=O)OCc2ccccc2)C1)C(=O)O] | 4-{[2-Carboxy-2-(3,3-dimethyl-butyrylamino)-ethylcarbamoyl]-methoxy}-2-(pyridin-2-ylaminomethyl)-pyrrolidine-1-carboxylic acid benzyl ester | EW-3-079-5 | 569.66 | Exp. 8A | 570.5 |
| 115 | 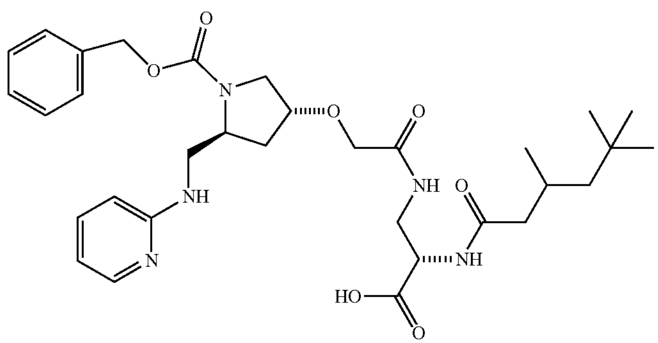 [SMILES: CC(CC(=O)N[C@@H](CNC(=O)CO[C@@H]1C[C@@H](CNc2ccccn2)N(C(=O)OCc2ccccc2)C1)C(=O)O)CC(C)(C)C] | 4-{[2-Carboxy-2-(3,5,5-trimethyl-hexanoylamino)-ethylcarbamoyl]-methoxy}-2-(pyridin-2-ylaminomethyl)-pyrrolidine-1-carboxylic acid benzyl ester | C32H45N5O7 | 611.74 | Exp. 8A | 612.6 |
| 116 | 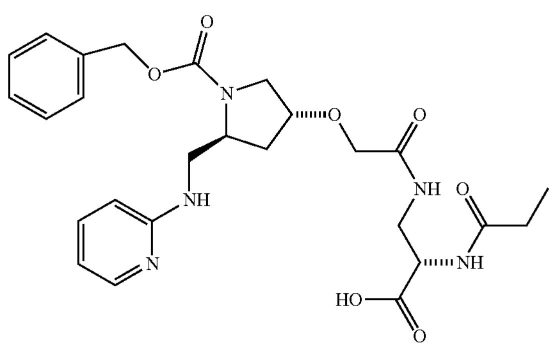 [SMILES: CCC(=O)N[C@@H](CNC(=O)CO[C@@H]1C[C@@H](CNc2ccccn2)N(C(=O)OCc2ccccc2)C1)C(=O)O] | 4-{[2-Carboxy-2-propionylamino-ethylcarbamoyl]-methoxy}-2-(pyridin-2-ylaminomethyl)-pyrrolidine-1-carboxylic acid benzyl ester | C26H33N5O7 | 527.57 | Exp. 8A | 528.4 |

TABLE 1-continued

| No. | Structure | Name | Formula | Mol-Weight | Example | LCMS |
|---|---|---|---|---|---|---|
| 117 | 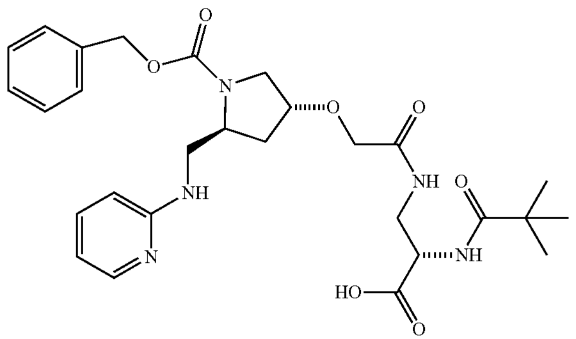 [SMILES: CC(C)(C)C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2,2-dimethyl-propionylamino)-ethylcarbamoyl]-methoxy}-2-(pyridin-2-ylaminomethyl)-pyrrolidine-1-carboxylic acid benzyl ester | C28H37N5O7 | 555.63 | Exp. 8A | 556.4 |
| 118 | 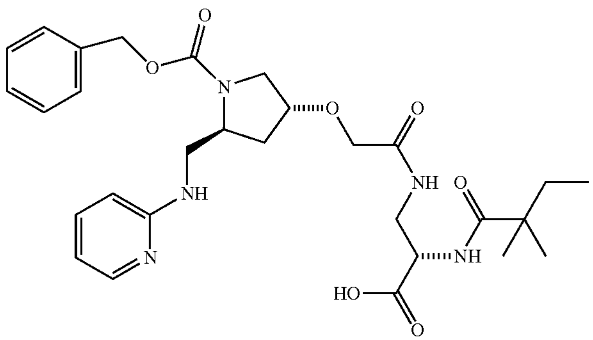 [SMILES: CCC(C)(C)C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2,2-dimethyl-butyrylamino)-ethylcarbamoyl]-methoxy}-2-(pyridin-2-ylaminomethyl)-pyrrolidine-1-carboxylic acid benzyl ester | C29H39N5O7 | 569.66 | Exp. 8A | 570.5 |
| 119 | 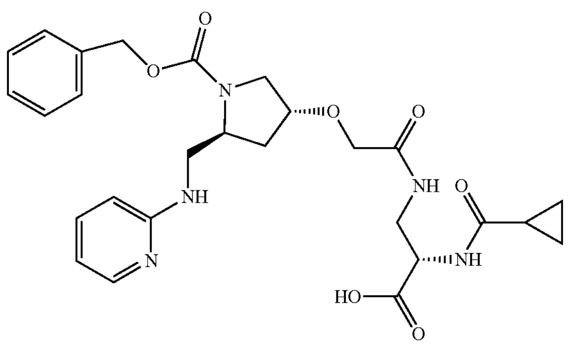 [SMILES: O=C(CO[C@@H]1C[C@@H](CNc2ccccn2)N(C(=O)OCc2ccccc2)C1)NC[C@H](NC(=O)C1CC1)C(=O)O] | 4-{[2-Carboxy-2-(cyclopropanecarbonyl-amino)-ethylcarbamoyl]-methoxy}-2-(pyridin-2-ylaminomethyl)-pyrrolidine-1-carboxylic acid benzyl ester | C27H33N5O7 | 539.59 | Exp. 8A | 540.4 |

TABLE 1-continued
| No. | Structure | Name | Formula | Mol-Weight | Example | LCMS |
|---|---|---|---|---|---|---|
| 120 | 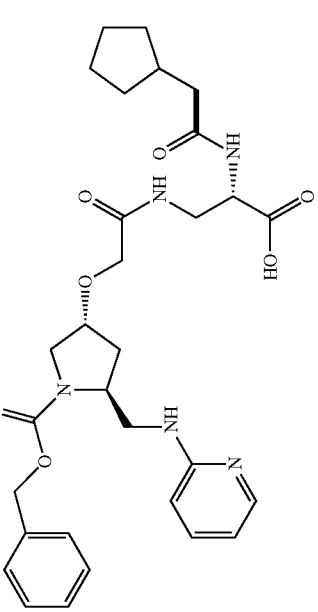 | 4-{[2-Carboxy-2-(2-cyclopentyl-acetylamino)-ethyl]carbamoyl]-methoxy}-2-(pyridin-2-ylaminomethyl)-pyrrolidine-1-carboxylic acid benzyl ester | C30H39N5O7 | 581.67 | Exp. 8A | 582.5 |
| 121 | 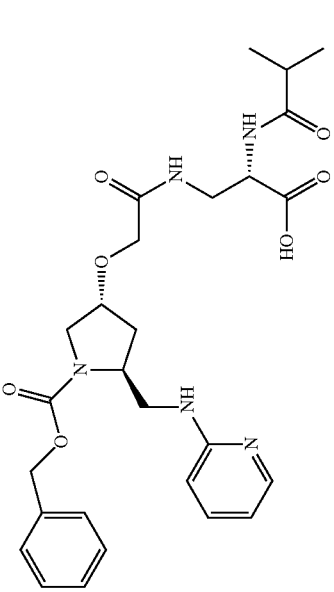 | 4-{[2-Carboxy-2-isobutyrylamino-ethyl]carbamoyl]-methoxy}-2-(pyridin-2-ylaminomethyl)-pyrrolidine-1-carboxylic acid benzyl ester | C27H35N5O7 | 541.60 | Exp. 8A | 542.4 |

TABLE 1-continued

| No. | Structure | Name | Formula | Mol-Weight | Example | LCMS |
|---|---|---|---|---|---|---|
| 122 | 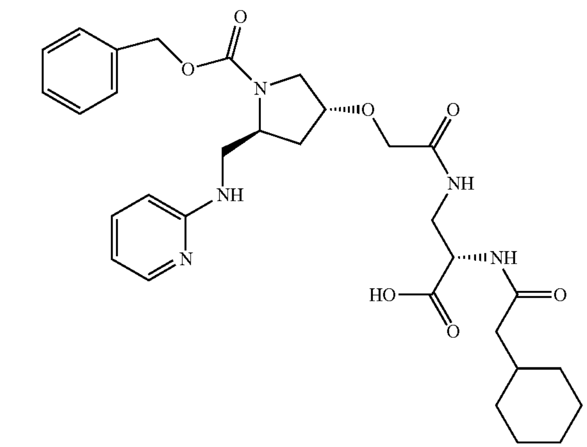 [SMILES: O=C(CO[C@@H]1C[C@@H](CNc2ccccn2)N(C(=O)OCc2ccccc2)C1)NC[C@H](NC(=O)CC1CCCCC1)C(=O)O] | 4-{[2-Carboxy-2-(2-cyclohexyl-acetylamino)-ethylcarbamoyl]-methoxy}-2-(pyridin-2-ylaminomethyl)-pyrrolidine-1-carboxylic acid benzyl ester | C31H41N5O7 | 595.69 | Exp. 8A | 596.6 |
| 123 | 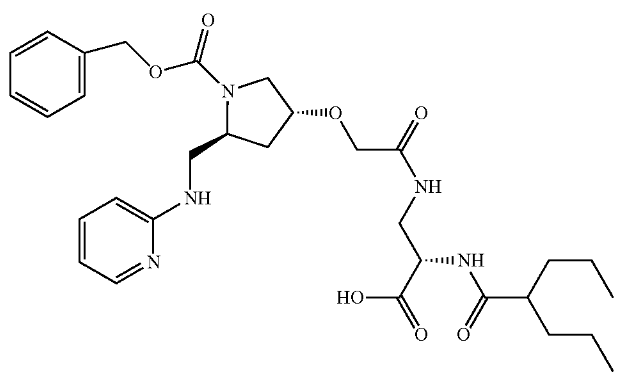 [SMILES: CCCC(CCC)C(=O)N[C@@H](CNC(=O)CO[C@@H]1C[C@@H](CNc2ccccn2)N(C(=O)OCc2ccccc2)C1)C(=O)O] | 4-{[2-Carboxy-2-(2-propyl-pentanoylamino)-ethylcarbamoyl]-methoxy}-2-(pyridin-2-ylaminomethyl)-pyrrolidine-1-carboxylic acid benzyl ester | C31H43N5O7 | 597.70 | Exp. 8A | 598.6 |

TABLE 1-continued

| No. | Structure | Name | Formula | Mol-Weight | Example | LCMS |
|---|---|---|---|---|---|---|
| 124 | 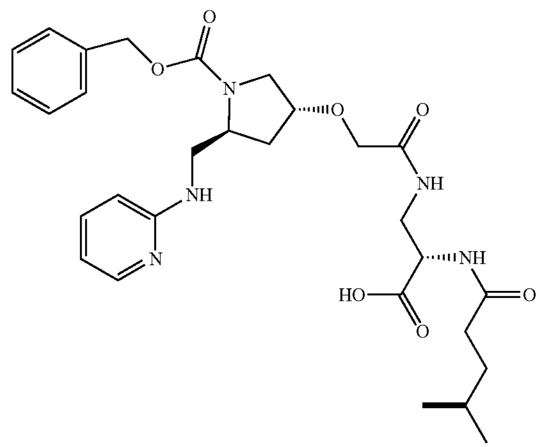 | 4-{[2-Carboxy-2-(4-methyl-pentanoylamino)-ethylcarbamoyl]-methoxy}-2-(pyridin-2-ylaminomethyl)-pyrrolidine-1-carboxylic acid benzyl ester | C29H39N5O7 | 569.65 | Exp. 8A | 570.5 |
| 125 | 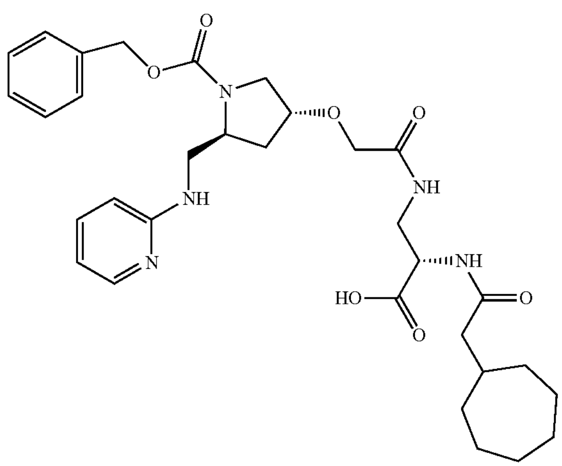 [SMILES: O=C(CO[C@@H]1C[C@@H](CNc2ccccn2)N(C(=O)OCc2ccccc2)C1)NC[C@H](NC(=O)CC1CCCCCC1)C(=O)O] | 4-{[2-Carboxy-2-(2-cycloheptyl-acetylamino)-ethylcarbamoyl]-methoxy}-2-(pyridin-2-ylaminomethyl)-pyrrolidine-1-carboxylic acid benzyl ester | C32H43N5O7 | 609.71 | Exp. 8A | 610.6 |

TABLE 1-continued

| No. | Name | Structure | Formula | Mol-Weight | Example | LCMS |
|---|---|---|---|---|---|---|
| 126 | 4-{[2-Carboxy-2-(2,4,6-triisopropyl-benzoylamino)-ethylcarbamoyl]-methoxy}-2-(pyridin-2-ylaminomethyl)-pyrrolidine-1-carboxylic acid benzyl ester | 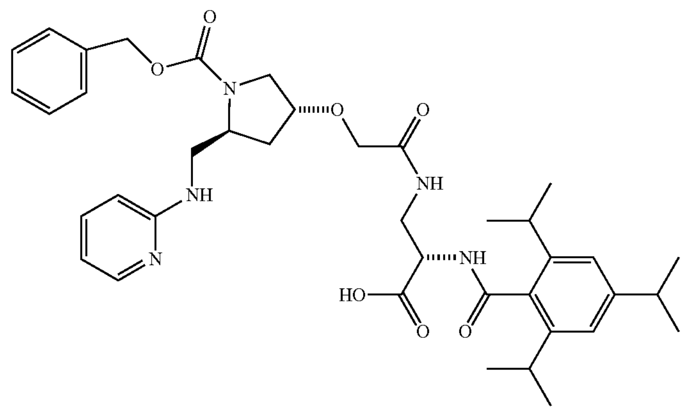 [SMILES: CC(C)c1cc(C(C)C)c(C(=O)N[C@@H](CNC(=O)CO[C@@H]2C[C@@H](CNc3ccccn3)N(C(=O)OCc3ccccc3)C2)C(=O)O)c(C(C)C)c1] | C39H51N5O7 | 701.86 | Exp. 8A | 702.6 |
| 127 | 4-{[2-Carboxy-2-(4-phenyl-butyrylamino)-ethylcarbamoyl]-methoxy}-2-(pyridin-2-ylaminomethyl)-pyrrolidine-1-carboxylic acid benzyl ester | 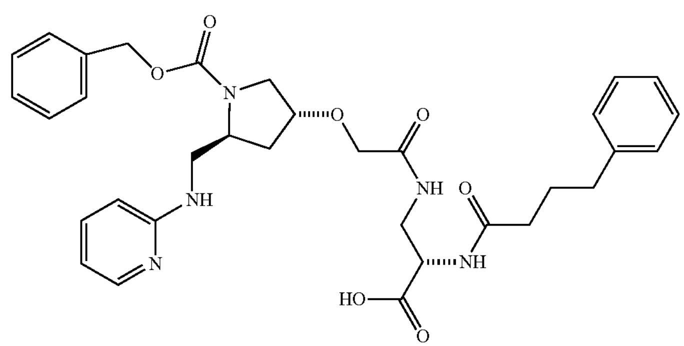 [SMILES: O=C(CO[C@@H]1C[C@@H](CNc2ccccn2)N(C(=O)OCc2ccccc2)C1)NC[C@H](NC(=O)CCCc1ccccc1)C(=O)O] | C33H39N5O7 | 617.69 | Exp. 8A | 618.6 |

TABLE 1-continued
| No. | Structure | Name | Formula | Mol-Weight | Example | LCMS |
|---|---|---|---|---|---|---|
| 128 | 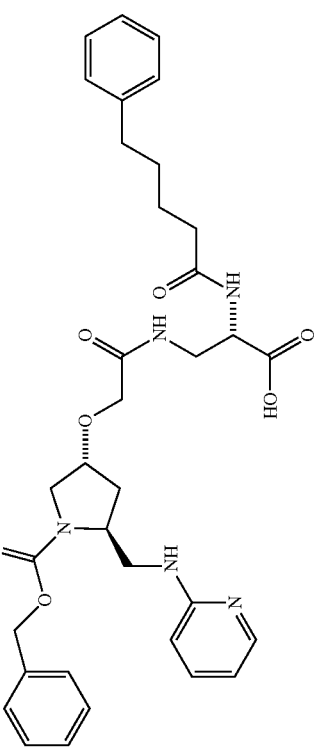 | 4-[[2-Carboxy-2-(5-phenyl-ethylcarbamoyl]-methoxy}-2-(pyridin-2-ylaminomethyl)-pyrrolidine-1-carboxylic acid benzyl ester | C34H41N5O7 | 631.72 | Exp. 8A | 632.6 |
| 129 | 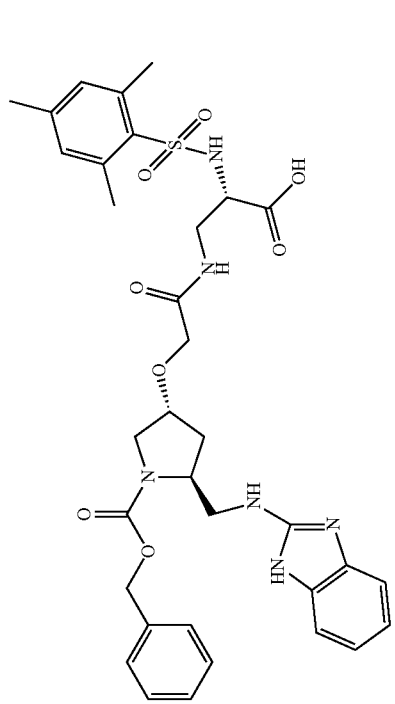 | 2-[(1H-Benzoimidazol-2-ylamino)-methyl]-4-{[2-benzenesulfonylamino)-ethylcarbamoyl]-methoxy}-pyrrolidine-1-carboxylic acid benzyl ester | C34H40N6O8S | 692.78 | Exp. 10 | 693.6 |

TABLE 1-continued

| No. | Structure | Name | Formula | Mol-Weight | Example | LCMS |
|---|---|---|---|---|---|---|
| 130 | 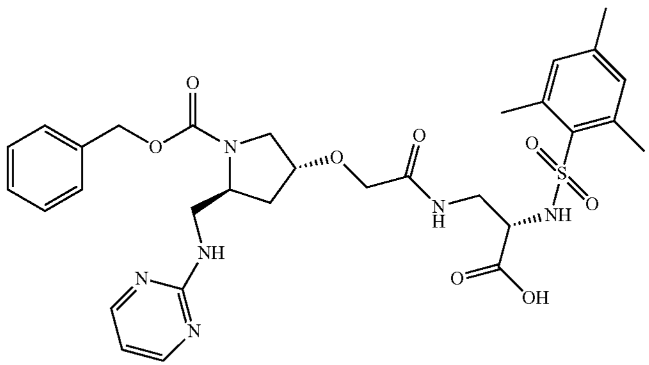 [SMILES: Cc1cc(C)c(S(=O)(=O)N[C@@H](CNC(=O)CO[C@@H]2C[C@@H](CNc3ncccn3)N(C(=O)OCc3ccccc3)C2)C(=O)O)c(C)c1] | 4-{[2-Carboxy-2-(2,4,6-trimethyl-benzenesulfonylamino)-ethyl]carbamoyl]-methoxy}-2-(pyrimidin-2-ylaminomethyl)-pyrrolidine-1-carboxylic acid benzyl ester | C31H38N6O8S | 654.73 | Exp. 10 | 655.5 |
| 131 | 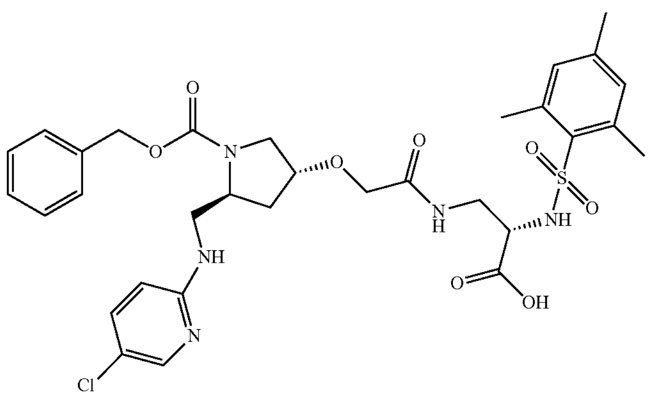 [SMILES: Cc1cc(C)c(S(=O)(=O)N[C@@H](CNC(=O)CO[C@@H]2C[C@@H](CNc3ccc(Cl)cn3)N(C(=O)OCc3ccccc3)C2)C(=O)O)c(C)c1] | 4-{[2-Carboxy-2-(2,4,6-trimethyl-benzenesulfonylamino)-ethyl]carbamoyl]-methoxy}-2-[(5-chloro-pyridin-2-ylamino)-methyl]-pyrrolidine-1-carboxylic acid benzyl ester | C32H38ClN5O8S | 688.19 | Exp. 10 | 683.6 |

TABLE 1-continued

| No. | Name | Structure | Formula | Mol-Weight | Example | LCMS |
|---|---|---|---|---|---|---|
| 132 | 4-{[2-Carboxy-2-(2,4,6-benzenesulfonylamino)-ethyl]carbamoyl]-methoxy}-2-[(2H-imidazol-2-ylamino)-methyl]-pyrrolidine-1-carboxylic acid benzyl ester | 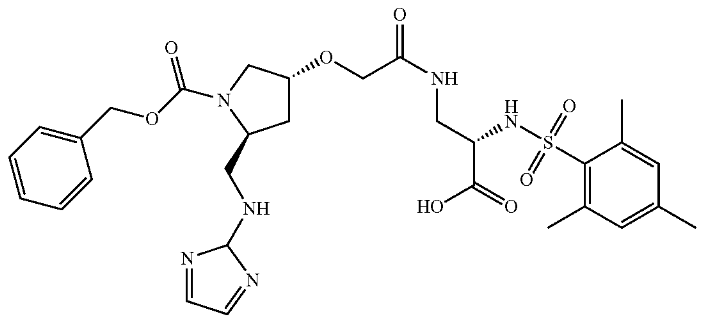 [SMILES: Cc1cc(C)c(S(=O)(=O)N[C@@H](CNC(=O)CO[C@@H]2C[C@@H](CNC3N=CC=N3)N(C(=O)OCc3ccccc3)C2)C(=O)O)c(C)c1] | C30H38N6O8S | 642.72 | Exp. 10 | 643.4 |
| 133 | 4-{[2-Carboxy-2-(2,4,6-trimethyl-benzenesulfonylamino)-ethyl]carbamoyl]-methoxy}-2-(isoquinolin-3-ylaminomethyl)-pyrrolidine-1-carboxylic acid benzyl ester | 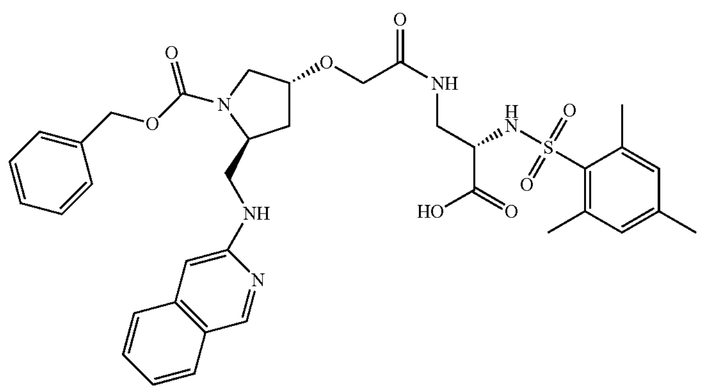 [SMILES: Cc1cc(C)c(S(=O)(=O)N[C@@H](CNC(=O)CO[C@@H]2C[C@@H](CNc3cc4ccccc4cn3)N(C(=O)OCc3ccccc3)C2)C(=O)O)c(C)c1] | C36H41N5O8S | 703.80 | Exp. 10 | 704.6 |

TABLE 1-continued

| No. | Structure | Name | Formula | Mol-Weight | Example | LCMS |
|---|---|---|---|---|---|---|
| 134 | 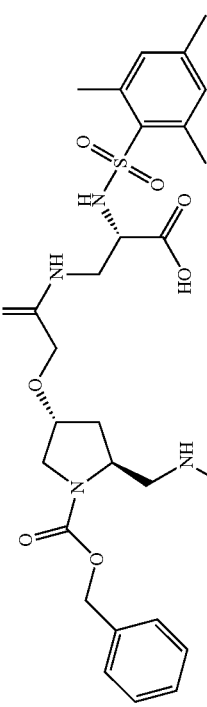 | 4-{[2-Carboxy-2-(2,4,6-trimethyl-benzenesulfonylamino)-ethyl]carbamoyl]-methoxy}-2-[(5-trifluoromethyl-pyridin-2-yl)amino)-methyl]-pyrrolidine-1-carboxylic acid benzyl ester | C33H38F3N5O8S | 721.74 | Exp. 10 | 722.4 |
| 135 | 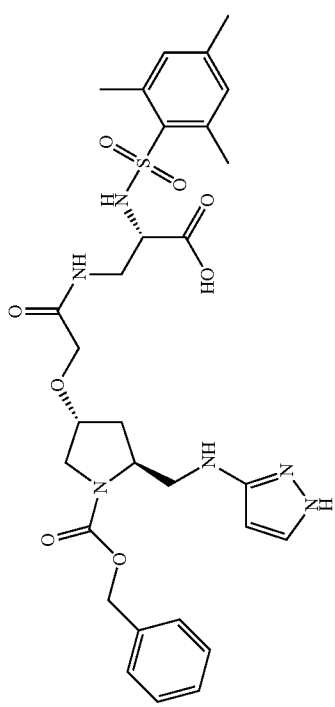 | 4-{[2-Carboxy-2-(2,4,6-trimethyl-benzenesulfonylamino)-ethyl]carbamoyl]-methoxy}-2-[(1H-pyrazol-3-ylamino)-methyl]-pyrrolidine-1-carboxylic acid benzyl ester | C30H38N6O8S | 642.72 | Exp. 10 | 643.3 |

TABLE 1-continued

| No. | Name | Structure | Formula | Mol-Weight | Example | LCMS |
|---|---|---|---|---|---|---|
| 136 | 4-{[2-Carboxy-2-(2,4,6-trimethyl-benzenesulfonylamino)-ethylcarbamoyl]-methoxy}-2-{[(5-methyl-pyridin-2-yl)amino]-methyl}-pyrrolidine-1-carboxylic acid benzyl ester | 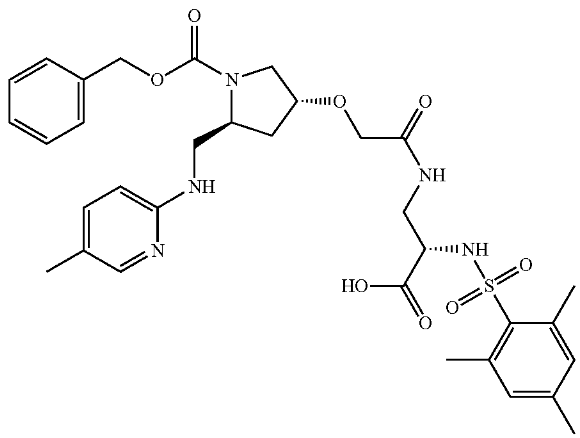 [SMILES: Cc1ccc(NC[C@@H]2C[C@@H](OCC(=O)NC[C@H](NS(=O)(=O)c3c(C)cc(C)cc3C)C(=O)O)CN2C(=O)OCc2ccccc2)nc1] | C33H41N5O8S | 667.77 | Exp. 10 | 668.6 |
| 137 | 4-{[2-Carboxy-2-(2,4,6-trimethyl-benzenesulfonylamino)-ethylcarbamoyl]-methoxy}-2-{[(6-methyl-pyridin-2-yl)amino]-methyl}-pyrrolidine-1-carboxylic acid benzyl ester | 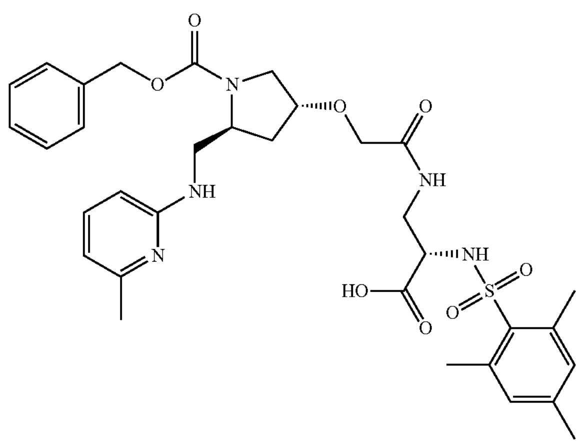 [SMILES: Cc1cc(C)c(S(=O)(=O)N[C@@H](CNC(=O)CO[C@@H]2C[C@@H](CNc3cccc(C)n3)N(C(=O)OCc3ccccc3)C2)C(=O)O)c(C)c1] | C33H41N5O8S | 667.77 | Exp. 10 | 668.4 |

TABLE 1-continued

| No. | Structure | Name | Formula | Mol-Weight | Example | LCMS |
|---|---|---|---|---|---|---|
| 138 | 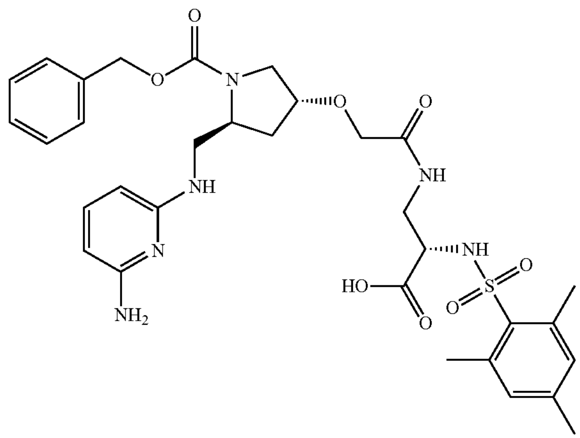 [SMILES: Cc1cc(C)c(S(=O)(=O)N[C@@H](CNC(=O)CO[C@@H]2C[C@@H](CNc3cccc(N)n3)N(C(=O)OCc3ccccc3)C2)C(=O)O)c(C)c1] | 2-[(6-Amino-pyridin-2-ylamino)-methyl]-4-{[2-carboxy-2-(2,4,6-trimethyl-benzenesulfonylamino)-ethylcarbamoyl]-methoxy}-pyrrolidine-1-carboxylic acid benzyl ester | C32H40N6O8S | 668.76 | Exp. 10 | 669.6 |
| 139 | 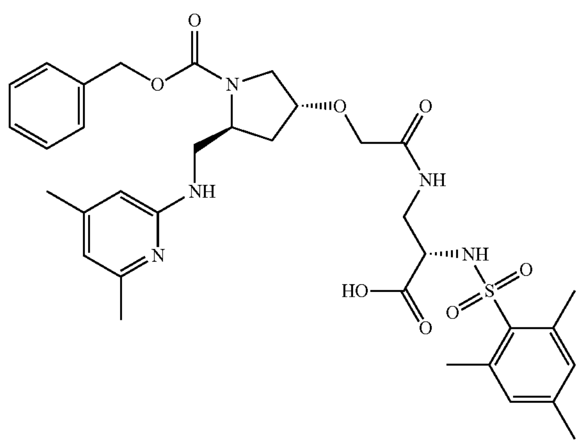 [SMILES: Cc1cc(C)nc(NC[C@@H]2C[C@@H](OCC(=O)NC[C@H](NS(=O)(=O)c3c(C)cc(C)cc3C)C(=O)O)CN2C(=O)OCc2ccccc2)c1] | 4-{[2-Carboxy-2-(2,4,6-trimethyl-benzenesulfonylamino)-ethylcarbamoyl]-methoxy}-2-[(4,6-dimethyl-pyridin-2-ylamino)-methyl]-pyrrolidine-1-carboxylic acid benzyl ester | C34H43N5O8S | 681.80 | Exp. 10 | 682.5 |

TABLE 1-continued

| No. | Name | Structure | Formula | Mol-Weight | Example | LCMS |
|---|---|---|---|---|---|---|
| 140 | 4-{[2-Carboxy-2-(2,4,6-trimethyl-benzenesulfonylamino)-ethyl]carbamoyl]-methoxy}-2-(quinolin-2-ylaminomethyl)-pyrrolidine-1-carboxylic acid benzyl ester | 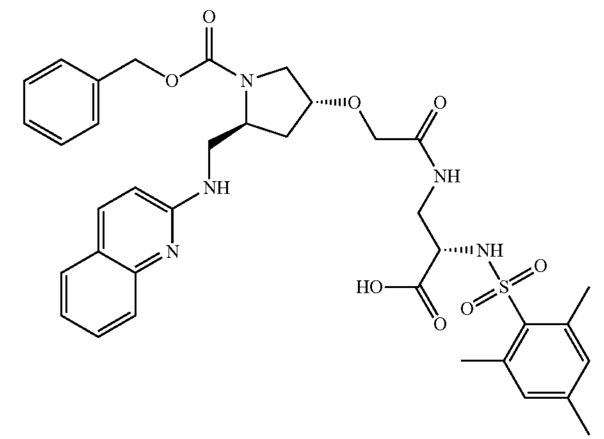 [SMILES: Cc1cc(C)c(S(=O)(=O)N[C@@H](CNC(=O)CO[C@@H]2C[C@@H](CNc3ccc4ccccc4n3)N(C(=O)OCc3ccccc3)C2)C(=O)O)c(C)c1] | C36H41N5O8S | 703.80 | Exp. 10 | 704.5 |
| 141 | 4-{[2-Carboxy-2-(2,4,6-trimethyl-benzenesulfonylamino)-ethyl]carbamoyl]-methoxy}-2-[(5-phenyl-pyridin-2-ylamino)-methyl]-pyrrolidine-1-carboxylic acid benzyl ester | 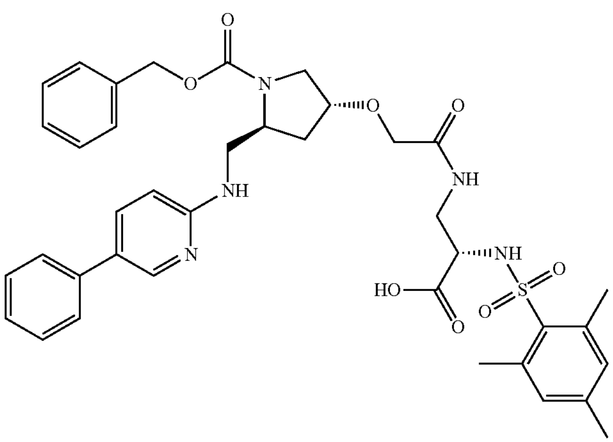 [SMILES: Cc1cc(C)c(S(=O)(=O)N[C@@H](CNC(=O)CO[C@@H]2C[C@@H](CNc3ccc(-c4ccccc4)cn3)N(C(=O)OCc3ccccc3)C2)C(=O)O)c(C)c1] | C38H43N5O8S | 729.84 | Exp. 10 | 730.6 |

TABLE 1-continued

| No. | Structure | Name | Formula | Mol-Weight | Example | LCMS |
|---|---|---|---|---|---|---|
| 142 | 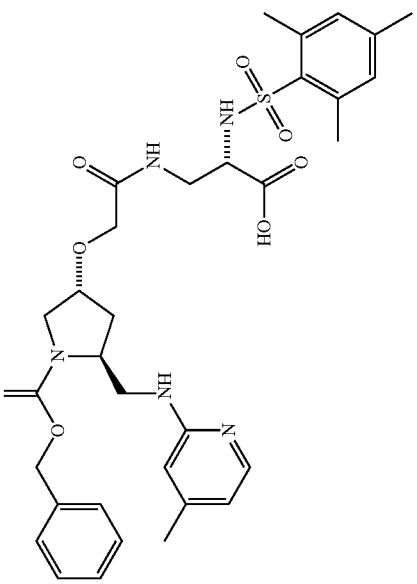 | 4-{[2-Carboxy-2-(2,4,6-trimethyl-benzenesulfonylamino)-ethylcarbamoyl]-methoxy}-2-[(4-methyl-pyridin-2-ylamino)-methyl]-pyrrolidine-1-carboxylic acid benzyl ester | C33H41N5O8S | 667.77 | Exp. 10 | 668.2 |
| 143 | 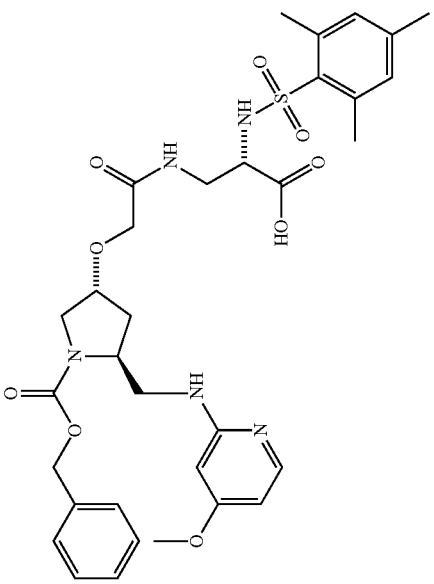 | 4-{[2-Carboxy-2-(2,4,6-trimethyl-benzenesulfonylamino)-ethylcarbamoyl]-methoxy}-2-[(4-methoxy-pyridin-2-ylamino)-methyl]-pyrrolidine-1-carboxylic acid benzyl ester | C33H41N5O9S | 683.77 | Exp. 10 | 684.3 |

TABLE 1-continued

| No. | Name | Structure | Formula | Mol-Weight | Example | LCMS |
|---|---|---|---|---|---|---|
| 144 | 4-{[2-Carboxy-2-(2,4,6-trimethyl-benzenesulfanylamino)-ethyl]carbamoyl]-methoxy}-2-[(4-chloro-pyridin-2-ylamino)-methyl]-pyrrolidine-1-carboxylic acid benzyl ester | 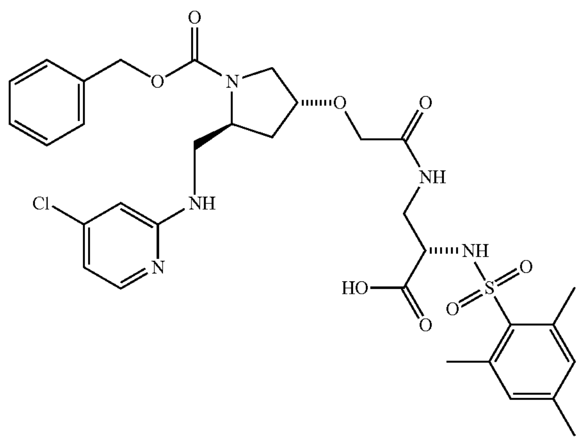 [SMILES: Cc1cc(C)c(S(=O)(=O)N[C@@H](CNC(=O)CO[C@@H]2C[C@@H](CNc3cc(Cl)ccn3)N(C(=O)OCc3ccccc3)C2)C(=O)O)c(C)c1] | C32H38ClN5O8S | 688.19 | Exp. 10 | 688.1 |
| 145 | 3-(2-{1-(3,3-Dimethyl-butyryl)-5-[(4-methoxy-pyridin-2-ylamino)-methyl]-pyrrolidin-3-yloxy}-acetylamino)-2-(2,4,6-trimethyl-benzenesulfonylamino)-propionic acid | 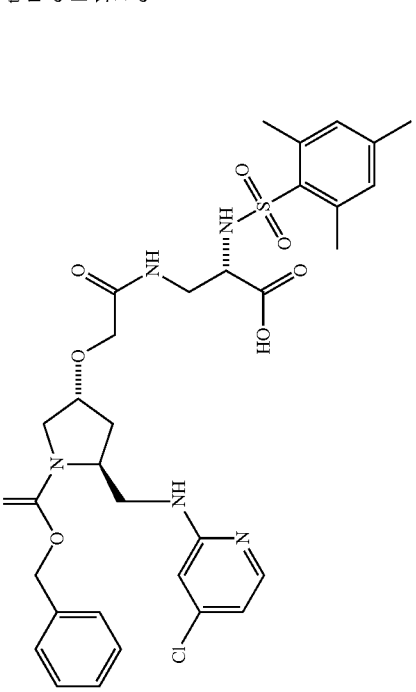 | C31H45N5O8S | 647.78 | Exp. 10 | 648.6 |

TABLE 1-continued

| No. | Structure | Name | Formula | Mol-Weight | Example | LCMS |
|---|---|---|---|---|---|---|
| 146 | 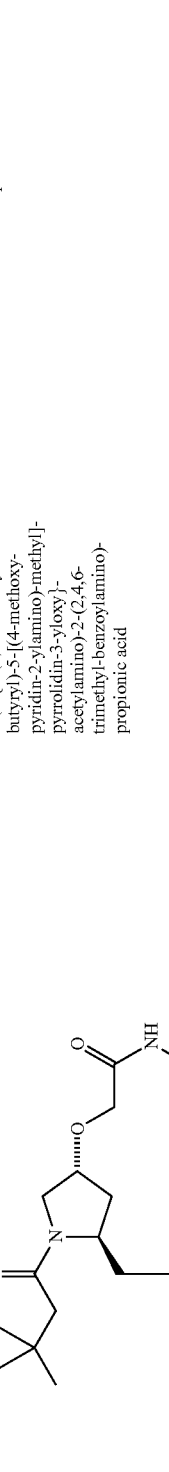 | 3-(2-{1-(3,3-Dimethyl-butyryl)-5-[(4-methoxy-pyridin-2-ylamino)-methyl]-pyrrolidin-3-yloxy}-acetylamino)-2-(2,4,6-trimethyl-benzoylamino)-propionic acid | C32H45N5O7 | 611.73 | Exp. 10 | 612.6 |
| 147 | 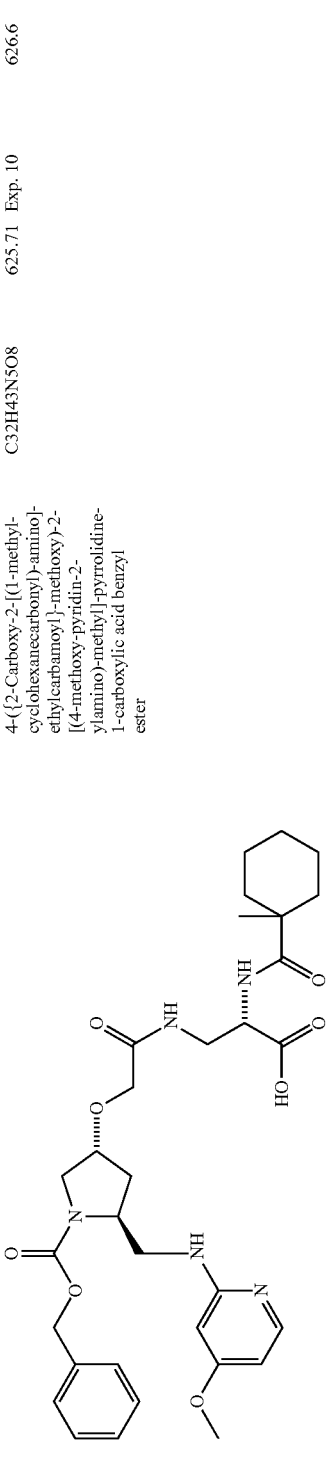 | 4-({2-Carboxy-2-[(1-methyl-cyclohexanecarbonyl)-amino]-ethyl}carbamoyl)-methoxy}-2-[(4-methoxy-pyridin-2-ylamino)-methyl]-pyrrolidine-1-carboxylic acid benzyl ester | C32H43N5O8 | 625.71 | Exp. 10 | 626.6 |
| 148 | 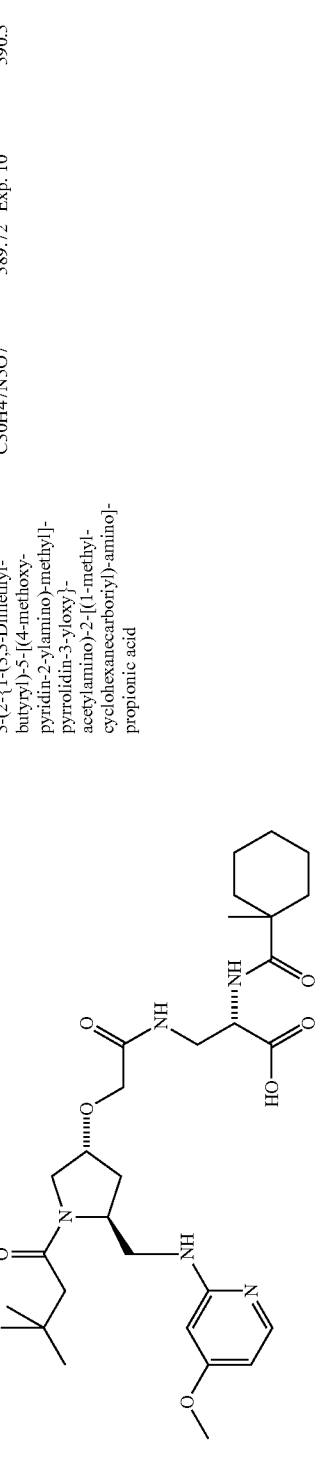 | 3-(2-{1-(3,3-Dimethyl-butyryl)-5-[(4-methoxy-pyridin-2-ylamino)-methyl]-pyrrolidin-3-yloxy}-acetylamino)-2-[(1-methyl-cyclohexanecarbonyl)-amino]-propionic acid | C30H47N5O7 | 589.72 | Exp. 10 | 590.5 |

TABLE 1-continued

| No. | Structure | Name | Formula | Mol-Weight | Example | LCMS |
|---|---|---|---|---|---|---|
| 149 | 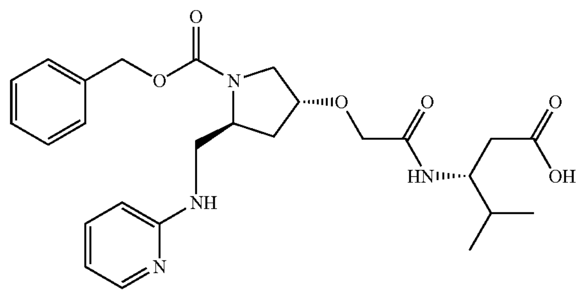 [SMILES: CC(C)[C@@H](CC(=O)O)NC(=O)CO[C@@H]1C[C@@H](CNc2ccccn2)N(C(=O)OCc2ccccc2)C1] | 4-[(1-Carboxymethyl-2-methyl-propylcarbamoyl)-methoxy]-2-(pyridin-2-ylaminomethyl)-pyrrolidine-1-carboxylic acid benzyl ester | C26H34N4O6 | 498.57 | Exp. 11 | 499 |
| 150 | 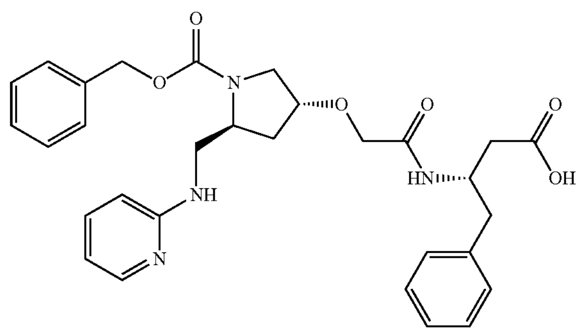 [SMILES: O=C(O)C[C@H](Cc1ccccc1)NC(=O)CO[C@@H]1C[C@@H](CNc2ccccn2)N(C(=O)OCc2ccccc2)C1] | 4-[(1-Carboxymethyl-2-phenyl-ethylcarbamoyl)-methoxy]-2-(pyridin-2-ylaminomethyl)-pyrrolidine-1-carboxylic acid benzyl ester | C30H34N4O6 | 546.61 | Exp. 11 | 547.5 |
| 151 | 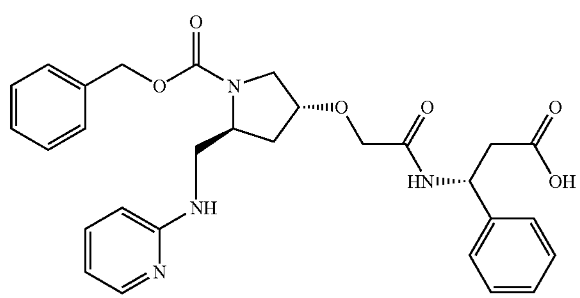 [SMILES: O=C(O)C[C@@H](NC(=O)CO[C@@H]1C[C@@H](CNc2ccccn2)N(C(=O)OCc2ccccc2)C1)c1ccccc1] | 4-[(2-Carboxy-1-phenyl-ethylcarbamoyl)-methoxy]-2-(pyridin-2-ylaminomethyl)-pyrrolidine-1-carboxylic acid benzyl ester | C29H32N4O6 | 532.59 | Exp. 11 | 533.4 |

TABLE 1-continued

| No. | Structure | Name | Formula | Mol-Weight | Example | LCMS |
|---|---|---|---|---|---|---|
| 152 | 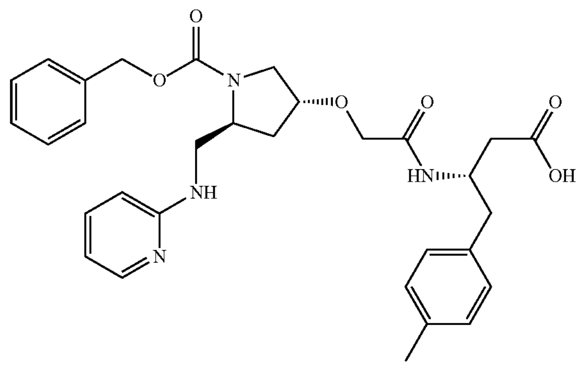 [SMILES: Cc1ccc(C[C@@H](CC(=O)O)NC(=O)CO[C@@H]2C[C@@H](CNc3ccccn3)N(C(=O)OCc3ccccc3)C2)cc1] | 4-[(1-Carboxymethyl-2-p-tolyl-ethylcarbamoyl)-methoxy]-2-(pyridin-2-ylaminomethyl)-pyrrolidine-1-carboxylic acid benzyl ester | C31H36N4O6 | 560.64 | Exp. 11 | 561.4 |
| 153 | 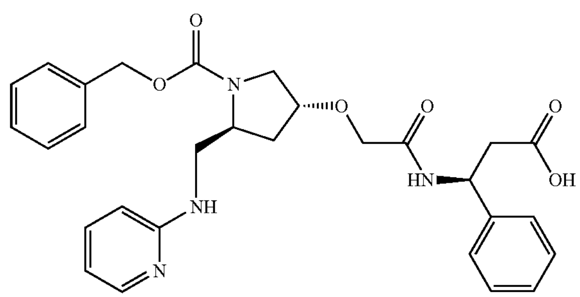 [SMILES: O=C(O)C[C@H](NC(=O)CO[C@@H]1C[C@@H](CNc2ccccn2)N(C(=O)OCc2ccccc2)C1)c1ccccc1] | 4-[(2-Carboxy-1-phenyl-ethylcarbamoyl)-methoxyl]-2-(pyridin-2-ylaminomethyl)-pyrrolidine-1-carboxylic acid benzyl ester | C29H32N4O6 | 532.59 | Exp. 11 | 533.5 |

TABLE 1-continued

| No. | Name | Structure | Formula | Mol-Weight | Example | LCMS |
|---|---|---|---|---|---|---|
| 154 | 4-{[3-Carboxy-3-(2,4,6-trimethyl-benzenesulfonyl)amino]-propylcarbamoyl]-methoxy}-2-(pyridin-2-ylaminomethyl)-pyrrolidine-1-carboxylic acid benzyl ester | 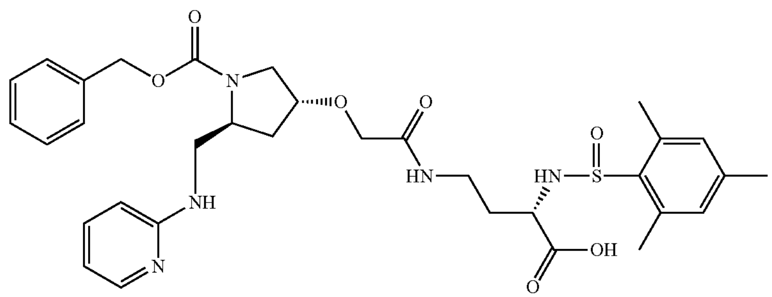 [SMILES: Cc1cc(C)c(S(=O)N[C@@H](CCNC(=O)CO[C@@H]2C[C@@H](CNc3ccccn3)N(C(=O)OCc3ccccc3)C2)C(=O)O)c(C)c1] | C33H41N5O8S | 667.77 | Exp. 11 | 668.2 |
| 155 | 4-({[2-Carboxy-2-(2,4,6-trimethyl-benzenesulfonyl)amino]-ethyl]-methyl-carbamoyl}-methoxy)-2-(pyridin-2-ylaminomethyl)-pyrrolidine-1-carboxylic acid benzyl ester | 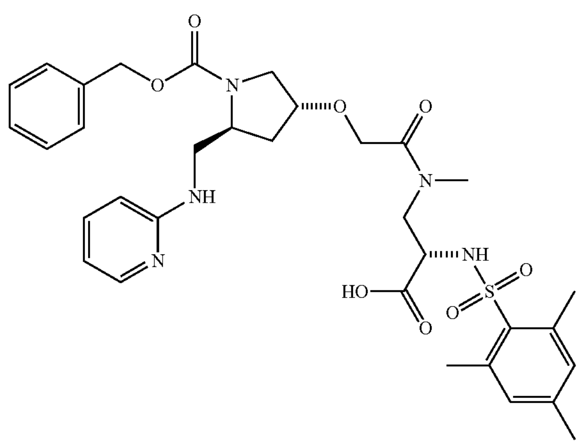 [SMILES: Cc1cc(C)c(S(=O)(=O)N[C@@H](CN(C)C(=O)CO[C@@H]2C[C@@H](CNc3ccccn3)N(C(=O)OCc3ccccc3)C2)C(=O)O)c(C)c1] | C33H41N5O8S | 667.77 | Exp. 11 | 668.2 |

TABLE 1-continued

| No. | Structure | Name | Formula | Mol-Weight | Example | LCMS |
|---|---|---|---|---|---|---|
| 156 | 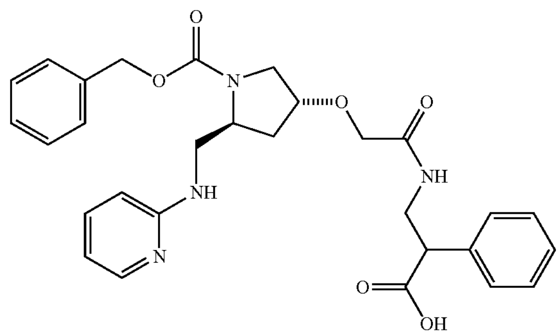 [SMILES: O=C(CO[C@@H]1C[C@@H](CNc2ccccn2)N(C(=O)OCc2ccccc2)C1)NCC(C(=O)O)c1ccccc1] | 4-[(2-Carboxy-2-phenyl-(pyridin-2-ylaminomethyl)-ethylcarbamoyl)-methoxy]-2-pyrrolidine-1-carboxylic acid benzyl ester | C29H32N4O6 | 532.59 | Exp. 11 | 533.4 |
| 157 | 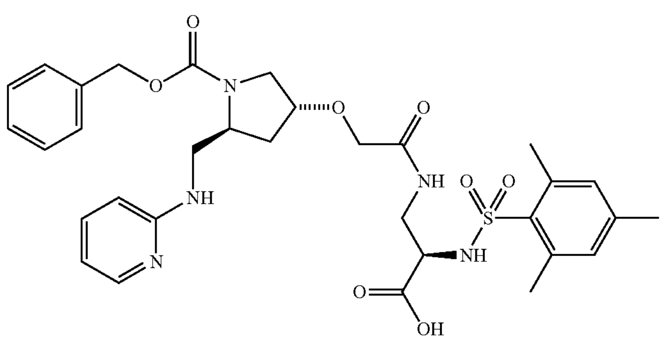 [SMILES: Cc1cc(C)c(S(=O)(=O)N[C@H](CNC(=O)CO[C@@H]2C[C@@H](CNc3ccccn3)N(C(=O)OCc3ccccc3)C2)C(=O)O)c(C)c1] | 4-{[2-Carboxy-2-(2,4,6-trimethyl-benzenesultonylamino)-ethylcarbamoyl]-methoxy}-2-(pyridin-2-ylaminomethyl)-pyrrolidine-1-carboxylic acid benzyl ester | C32H39N5O8S | 653.75 | Exp. 11 | 654.5 |

Even more preferred compounds according to the present invention are those mentioned in any of the tables herein and those further disclosed and/or characterized in the examples.

The present inventors have surprisingly found that the compounds according to the present invention are particularly suitable to interact with integrins, more particularly with integrin alpha5beta1 which is also referred to herein as alpha5beta1. Without wishing to be bound by any theory the present inventors assume that the structure underlying the compounds according to the present invention, more particularly comprising a central core structure represented by D in formula (I) and a total of three radii emerging there from, namely the radius X-A, the radius Z-G, and the radius Y-B, provides for this effect. Also, this class of compounds is advantageous in so far as it has a rather simple core structure provided by the heterocyclic and homocyclic, respectively, ring as represented by D of formula (I). It seems that this rather flexible design confers to the compounds according to the present invention the ability to specifically interact with the integrin, typically reflected in a low IC50 value. The compounds according to the present invention seem to be particularly binding and specific, respectively, for integrin alpha5beta1. However, it is also within the present invention that the compounds of the present invention show cross-reactivity with other compounds, preferably with other integrins.

According to the current understanding of the inventors and without wishing to be bound by any theory, the various radii contributing in a synergistic manner to the binding of the compounds according to the present invention to the integrins and preferably to integrin alpha5beta1, can be assigned the following functions.

The interaction of any molecule with integrins usually requires a basic and acidic moiety present in said molecule. These moieties are represented in the compounds according to the present invention by radius Z-G and radius Y-B, respectively. The compounds according to the present invention additionally comprise radius X-A, which to modulate the physico-chemical, pharmacokinetic and pharmacodynamic properties of the compound, without effecting the activity or selectivity towards the target protein. A variety of functional groups can be placed in the position of radius X-A to increase for instance the solubility or metabolic stability.

The basic radius Z-G can interact with carboxylic group(s) of the integrin protein. Basic functional groups like guanidine, amidine or aromatic nitrogen containing heterocycles are widely used as interaction partners. The term "basic" refers in so far to a functional group which is positively charged under physiologic conditions. However, also non-charged functional groups like amid or urea serve this requirement. The further design of this radius may be taken from the overall disclosure of the present application.

The acidic radius Y-B bears usually a carboxylic acid and interacts with metal ions, which are incorporated in the protein structure. Esters, such as —CO2Alk and amides such as —CONR5R6 being derivatives of this carboxylic acid group (—CO2H) may advantageously be used as prodrugs of the active compound. Such prodrugs are compounds which undergo biotransformation prior to exhibiting their pharmacological effects and the invention particularly extends to prodrugs of the acid. Such prodrugs are well known in the art, see for example International Patent Application No. WO00/26419, Bodor, N. (Alfred Benzon Symposium, 1982, 17, 156), Singh, G. et al. (J. Sci. Ind. Res., 1996, 55, 497) and Bundgaard, H., (Design of Prodrugs, 1985, Elsevier, Amsterdam). It is thus within the present invention that the compounds according to the present invention also comprise the prodrug form of the compounds disclosed herein.

For this acidic interaction realised by the compounds according to the present invention a carboxylic acid group is preferably used as interaction partner for the interacting group of the integrin. Preferably the counter ion on the integrin is a metal ion. However, this interaction does not necessarily require a carboxylic acid functional group. Other functional groups like tetrazole, phosphates and acylsulfonamides can also serve as a binding partner for the group of the integrin interacting with said compound. These groups are bioisosteres for the carboxylic group. Other bioisosters for the carboxylic group are known to the ones skilled in the art. Thus the compounds according to the present invention also comprise those compounds where the carboxylic group is replaced by a bioisoster of such carboxylic group.

As used herein, each of the following terms, used alone or in conjunction with other terms, are preferably used in the following meaning (except where noted to the contrary):

The term "alkyl" refers to a saturated aliphatic radical containing from one to ten carbon atoms or a mono- or poly-unsaturated aliphatic hydrocarbon radical containing from two to twelve carbon atoms, containing at least one double and triple bound, respectively. Thus in a preferred embodiment, the term alkyl also comprises alkenyl and alkynyl. "Alkyl" refers to both branched and unbranched, i.e. non-linear alkyl groups. Preferred alkyl groups are straight chain alkyl groups containing from one to eight carbon atoms. More preferred alkyl groups are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O). "Substituted alkyl" refers to alkyl groups straight or branched further bearing one or more substituents. One substituent also means mono-substituted and more substitutents mean poly-substituted. It should be understood that any combination term using a "substituted alkyl" prefix refers to analogs according to the above definition of "substituted alkyl". For example, a term such as "substituted alkylaryl" refers to substituted alkyl group linked to an aryl group. Additionally, it is within the present invention that the term alky, particularly in the branched embodiment, also comprises embodiments where the branch of the branched alky residue or moiety is either linear or branched in itself.

The term "cycloalkyl" refers to the cyclic analogue of an alkyl group, as defined above, optionally unsaturated and/or substituted. Preferred cycloalkyl groups are saturated cycloalkyl groups, more particularly those containing from three to eight carbon atoms, and even more preferably three to six carbon atoms. "Substituted cycloalkyl" refers to cycloalkyl groups further bearing one or more substituents. "Mono-unsaturated cycloalkyl" refers to cycloalkyl containing one double bond or one triple bond. "Poly-unsaturated cycloalkyl" refers to cycloalkyl containing at least two double bonds or two triple bonds or a combination of at least one double bond and one triple bond.

The term "alkenyl" refers to an unsaturated hydrocarbon group containing at least one carbon-carbon double bond, including straight-chain, branched-chain, and cyclic groups. Preferred alkenyl groups have one to twelve carbons. More preferred alkenyl groups have one to six carbons. "Substituted alkenyl" refers to alkenyl groups further bearing one or more substitutents.

The term "cycloalkenyl" refers to the cyclic analog of an alkenyl group, as defined above, optionally substituted. Preferred cycloalkenyl groups are containing from four to eight carbon atoms. "Substituted cycloalkenyl" refers to cycloalkenyl groups further bearing one or more substituents. "Mono-unsaturated cycloalkenyl" refers to cycloalkenyl containing one double bond. "Poly-unsaturated cycloalkenyl" refers to cycloalkenyl containing at least two double bonds.

The term "alkynyl" refers to an unsaturated hydrocarbon group containing at least one carbon-carbon triple bond, including straight-chain, branched-chain, and cyclic groups. Preferred alkynyl groups have one to twelve carbons. More preferred alkynyl groups have one to six carbons. "Substituted alkynyl" refers to alkynyl groups further bearing one or more substitutents.

The term "aryl" refers to aromatic groups having in the range of 6 to 14 carbon atoms and "substituted aryl" refers to aryl groups further bearing one or more substituents. It should be understood that any combination term using an "ar" or "aryl" prefix refers to analogs according to the above definition of "aryl". For example, a term such as "aryloxy" refers to aryl group linked to a second group via an oxygen.

Each of the above defined "alkyl", "cycloalkyl", and "aryl" shall be understood to include their halogenated analogs, whereby the halogenated analogs may comprise one or several halogen atoms. The halogenated analogs thus comprise any halogen radical as defined in the following.

The term "halo" refers to a halogen radical selected from fluoro, chloro, bromo, iodo. Preferred halo groups are fluoro, chloro and bromo.

The term "heteroaryl" refers to a stable 5 to 8 membered, preferably 5 or 6 membered monocyclic or 8 to 11 membered bicyclic aromatic heterocycle radical. Each heterocycle consists of carbon atoms and from 1 to 4 heteroatoms selected from the group consisting of nitrogen, oxygen, sulfur. The heterocycle may be attached by any atom of the cycle, which preferably results in the creation of a stable structure. Preferred heteroaryl radicals as used herein include, for example, furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthridinyl, pteridinyl, carbazolyl, acridinyl, phenazinyl, phenothiazinyl and phenoxazinyl. "Substituted heteroaryl" refers to heteroaryl groups further bearing one or more substituents.

The term "heterocyclyl" refers to a stable 5 to 8 membered, preferably 5 or 6 membered monocyclic or 8 to 11 membered bicyclic heterocycle radical which may be either saturated or unsaturated, and is non-aromatic. Each heterocycle consists of carbon atom(s) and from 1 to 4 heteroatoms selected from the group consisting of nitrogen, oxygen and sulfur. The heterocycle may be attached by any atom of the cycle, which preferably results in the creation of a stable structure. Preferred heterocycle radicals as used herein include, for example, pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione. "Mono-unsaturated heterocyclyl" refers to heterocyclyl containing one double bond or one triple bond. "Poly-unsaturated heterocyclyl" refers to heterocyclyl containing at least two double bonds or two triple bonds or a combination of at least one double bond and one triple bond.

"Substituted heterocyclyl" refers to heterocyclyl groups further bearing one or more substituents.

The terms "heterocyclyl", "heteroaryl" and "aryl", when associated with another moiety, unless otherwise specified, shall have the same meaning as given above. For example, "aroyl" refers to phenyl or naphthyl linked to a carbonyl group (C=O).

Each aryl or heteroaryl unless otherwise specified includes its partially or fully hydrogenated derivative. For example, quinolinyl may include decahydroquinolinyl and tetrahydroquinolinyl, naphthyl may include its hydrogenated derivatives such as tetrahydronaphthyl.

As used herein above and throughout this application, "nitrogen" or "N" and "sulfur" or "S" include any oxidized form of nitrogen and sulfur and the quaternized form of any basic nitrogen sulfoxide, sulfone, nitrone, N-oxide.

As used herein, the wording "and any derivative of each thereof" as contained in a recitation of a group of compounds, means that any of the compound can be present as a derivative. Such derivative can be any derivative disclosed herein and is more preferably any derivative specified in connection with said compounds and group of compounds, respectively. It is also within the present invention that any substitution of any compound can be attached to said compound at any position, preferably any position which allows the formation of a chemically stable compound.

As used herein a wording defining the limits of a range of length such as e.g. "from 1 to 5" means any integer from 1 to 5, i.e. 1, 2, 3, 4 and 5. In other words, any range defined by two integers explicitly mentioned is meant to comprise any integer defining said limits and any integer comprised in said range.

As used herein the term substituted shall mean that one or more H atom of the group or compound which is substituted, is replaced by a different atom, a group of atoms, a molecule or a molecule moiety. Such atom, group of atoms, molecule or molecule moiety is also referred to herein as substituent.

It is also within the present invention that any substituent may in turn be substituted by a substituent. A group, structure, moiety or the like which is substituted may comprise several substituents which may either be different or the same.

The substituent can be selected from any of the groups, moieties and substituents disclosed herein. However, the substituent is preferably selected from the group comprising hydroxy, alkoxy, mercapto, cycloalkyl, heterocyclic, aryl, heteroaryl, aryloxy, halogen, trifluoromethyl, difluoromethyl, cyano, nitrone, amino, amido, —C(O)H, acyl, oxyacyl, carboxyl, carbamate, sulfonyl, sulphonamide and sulfuryl. Any of the substituents may be substituted itself by any of the aforementioned substituents. This applies preferably to cycloalkyl, heterocylic, aryl, heteroaryl and aryloxy. It is also preferred that alkoxy and mercapto are those of a lower alkyl group. It is to be acknowledged that any of the definition provided herein also applies to any substituent.

As used herein in connection with an embodiment of the various aspects of the present invention the term "each and independently selected from a group" or "are independently from each other selected from the group" refers to two or more atoms, groups, substituents, moieties or whatsoever and describes that the single atom, group etc. mentioned can be selected from the group. The wording used is a truncation which avoids unnecessary repetition as otherwise for each of the atoms, groups etc. the same group definition would have to be repeated.

As used herein in connection with an embodiment of the various aspects of the present invention the term "each and individually absent" refers to two or more atoms, groups, substituents, moieties or whatsoever and describes that the single atom, group etc. mentioned can be absent regardless whether any of the other atoms, groups etc. mentioned is absent. The wording used is a truncation which avoids unnecessary repetition as otherwise for each of the atoms, groups etc. the fact that it may be absent in an embodiment of the invention would have to be repeated.

It is within the present invention that at least some of the substituents are non-symmetrical in their design and, therefore, provide different orientations and optionally reaction sites or positions which can be used to attach the substituent to another moiety of the compound. Based on this the linkage between the substituent and the respective moiety of the compound varies depending on the particular orientation and thus site(s) of the substituent used for such linkage in various embodiments of the compounds disclosed herein. It is within the present invention that any such orientation of the substituent and thus linkage is covered by the present disclosure and representations. The same applies also to other groups or moieties.

It is within the present invention that the features of the various embodiments of the present invention can be realized either alone or in combination with the features of any other embodiment(s) of the present invention. Thus any combination of an/the individual feature or the combination of features of an embodiment of the present invention with an/the individual feature(s) or the combination of features of any other embodiment(s), either alone or in combination with (an) other embodiment(s), shall be disclosed by the present specification. This applies particularly to the various embodiments and features, respectively, of the compounds disclosed herein.

In a further aspect the present invention is related to a pharmaceutical composition comprising a compound according to any of the aspects of the present invention and a pharmaceutically acceptable carrier, diluent or excipient.

Any of the compounds according to the present invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

It shall be understood by the one of ordinary skill in the art that all compounds of the invention are preferably those which are chemically stable. This applies to any of the various uses of the compounds according to the present invention disclosed herein.

In a further aspect the compounds according to the present invention comprise a further moiety. Such further moiety preferably confers functional features to the compounds. It is to be acknowledged that such further moiety is preferably attached to any other part of the compounds according to the present invention, although it is also within the present invention that the moiety and moieties, more preferably the individual chemical or functional group or arrangement of such group, present in the compounds according to the present invention provides for the functional feature(s). More preferably such further moiety is an additional moiety, most preferably a compound on its own, which is attached, preferably conjugated to any of the compounds according to the present invention. Such further moiety is preferably selected from the group comprising a detection moiety, a targeted moiety and a delivery moiety. It is to be understood that the same moiety can have several functions. Accordingly, any specification in so far is not limiting the purpose for which such further moiety is incorporated into any of the compounds according to the present invention.

A detection moiety is preferably a moiety which allows the detection of the compound in vitro, ex vivo, in vivo and/or in situ. A preferred detection moiety is a label.

In a preferred embodiment the compound according to the present invention comprises a label and is also referred to herein as a labeled compound according to the present invention. By a "labeled compound according to the present invention" herein is meant a compound according to the present invention that has at least one element, isotope or chemical compound attached to enable the detection of the compound or the compound bound to a target such as an integrin. In general, labels as used herein, may be taken from any of the following classes: a) isotopic labels, which are preferably radioactive or heavy isotopes, including paramagnetic material; b) X-ray attenuating material; c) immune labels which comprise but are not limited to antibodies, antigens, or labels recognized by antibodies or other proteins such as biotin or antibody epitopes; d) colored, chemiluminescent, luminescent or fluorescent labels; e) enzyme substrates or enzymes; and f) other labels complexing detectable ions such as hexa-histidine sequence. The labels may be incorporated into the compound at any position using well known methods, which are selected, in part, based on the chemical nature of the compound and the label. More preferred labels include $^{14}C$, $^{13}C$, $^{15}N$, $^{3}H$, biotin, and fluorescent labels as are well known in the art.

A specifically bound labeled compound could be detected by using in vivo imaging methods like radionucleotide imaging, positron emission tomography, computerized axial tomography or magnetic imaging resonance methods. The specifically bound labeled compound could be also detected using ex vivo imaging methods, wherein, following the administration isolated cells or tissue probes are obtained from the individual and the integrin bound compound will be detected in these probes. Alternatively, the labeled compound could be applied to the isolated cells or tissue probes after obtaining the probes from the individuals. The specific binding of the labeled compound to the integrin could be detected directly or via the label moiety by radioactivity, fluorescence, luminescence, immunological or enzymatic reactions. For example, the compound is directly coupled to an enzyme substrate, i.e. labeled with an enzyme substrate, which could be detected after incubation with the enzyme via an chromogenic, fluorescent or luminescent reaction, or the label could be recognized by an other molecule like antibody which is conjugated to an enzyme like horseradish peroxidase, alkaline phosphatase, beta-galactosidase and others, are well known in the art.

In a further embodiment the further moiety is a targeted moiety. Preferably, the targeted moiety is a pharmaceutically active compound, which could be targeted by the compound according to the present invention to the site of action via specific interaction of the compound according to the present invention with the integrin, more preferably alpha5beta1. As mentioned above, the targeted moiety can also be active as detection moiety. The targeted is preferably selected from the group comprising cytotoxins, radionuclides, chemotherapeutics, pharmaceutically active proteins like antibodies or cytotoxic proteins, linker molecules for delivery of gentherapeutic vectors, or liposomes.

More preferably and generally applicable to any further moiety described herein, the attachment of the chemical compound according to the present invention to the further moiety is achieved through a binding mechanism which is selected from the group comprising covalent binding, non-covalent binding. For example, where the pharmaceutical active agent is a cytotoxin coupled to the compounds according to the present invention. This complex should bind specifically to the integrin alpha5beta1, which is poorly expressed on quiescent vasculature, but significantly upregulated on endothelial cells in tumors and after stimulation with growth factors. Therefore this complex should bind only to activated endothelial cells, which are symptomatic for disorders connected with angiogenesis, kill these cells exclusively and stops consequently the pathological angiogenesis.

In a preferred embodiment the further moiety is a delivery moiety. Such delivery moiety is any agent which is suitable to improve the stability, solubility and pharmacokinetic properties of the compound to optimize the bioavailability after administration. Therefore, the compound shows improved properties through the moiety itself or in combination with a particular formulation. For example, the addition of a fluorine group to the molecule increases the solubility in polyfluorated vehicles and improves the bioavailability of the compound in combination with this special vehicle.

In an embodiment the composition comprises a further pharmaceutically active compound, preferably such further pharmaceutically active compound is selected from the group comprising chemotherapeutic agents, anti-hormones, agents influencing the vascular permeability, agents for photodynamic therapy, and anti-angiogenic drugs. The combination of anti-angiogenic drugs with different mechanisms of action may lead to synergistic anti-angiogenic effects.

Any of these agents are known to the ones skilled in the art. Preferred chemotherapeutic agents are 5-fluorouracil, gemcitabine, carboplatin, paclitaxel, taxol, oxaliplatin, irinotecan, and cisplatin. Preferred agents used as anti-hormones are cyproproterone acetate and tamoxifen. Preferred agents influencing vascular permeability and/or angiogenesis are COX-2 inhibitors, NO-synthase inhibitors, bradykinin receptor antagonists, such as Icatibant, and others. Also preferred anti-angiogenic drugs are compounds effecting VEGF activity, such as, VEGF or VEGF-receptor antibodies or fragments, e.g. Avastin, Lucentis, soluble VEGF-receptor fragments, VEGF binding aptamers (Macugen, Eye001), VEGF-receptor-kinase inhibitors e.g. SU5416 or PTK787/ZK222584, or agents affecting the action of other angiogenic growth factors such as PDGF and others. Other anti-angiogenic drugs are inhibitors of matrix metalloproteases, endogenous inhibitors, such as endostatin and angiostatin, other integrin inhibitors, thalidomide and derivatives and others. A preferred agent used for photodynamic therapy is Visudyne.

In a preferred embodiment of the composition the compound is present as a pharmaceutically acceptable salt or a pharmaceutically active solvate.

In an even more preferred embodiment the pharmaceutically active compound is either alone or in combination with any of the ingredients of the composition present in a multitude of individualized dosages and/or administration forms.

It is also within the present invention that pharmaceutical composition as well as the medicament which is manufactured using the compounds according to the present invention, is used with other therapies used in the prevention and/or treatment of any disease disclosed herein, preferably any disease for the prevention and/or treatment of which the pharmaceutical composition and/or the medicament which is manufactured using the compounds according to the present invention, is used. Such other therapies are selected from the group comprising chemotherapy, anti-hormone therapy, radiation therapy, photodynamic therapy, anti-angiogenic therapy and surgery. These other therapies are known to the ones skilled in the art. Basically chemotherapy means the standard chemotherapy usually applied to cancer patients as well as the metronomic therapy, the frequent application of low dose chemotherapeutics (Hahnfeldt, 2003, J Theor Biol., 220, 545). Anti-hormone therapy preferably means the standard hormone therapy usually applied to cancer patients with hormone dependent cancers such as breast or prostate cancer. Photodynamic therapy is the current standard treatment for defined stages of age related macular degeneration based on the photochemical injury of the blood vessels in the neovascular membranes of AMD patients, through the properties of a photo-active compound and a targeted laser treatment of the affected areas in the eye (Verteporfin in Visudyne, Novartis).

In a further aspect the present invention is related to the use of the compounds according to the present invention as a medicament and for the manufacture of a medicament, respectively. It is to be understood that any of the compounds according to the present invention can be used for the treatment of or for the manufacture of a medicament for the treatment of any of the diseases disclosed herein, irrespective of the mode of action or the causative agent involved as may be specified herein. Of course, it may particularly be used for any form of such disease where the particular causative agent is involved. Causative agent as used herein also means any agent which is observed in connection with the particular disease described and such agent is not necessarily causative in the sense that it causes the observed diseases or diseased condition. It is within the present invention that the medicament is preferably a pharmaceutical composition as described herein. The features disclosed in connection with the medicament and its manufacture are also applicable to the pharmaceutical composition and the features disclosed in connection with the pharmaceutical composition are also applicable to the medicament. More preferably, the pharmaceutical composition according to the present invention can be used for the treatment and/or prevention of any of the diseases disclosed herein.

The same applies also to each and any other use of the compounds according to the present invention, more particularly to the use of the compounds according to the present invention as diagnostic tools, the use of said compounds in the method for the treatment of any of the diseases disclosed herein and the use of said compounds for as inhibitors, preferably as inhibitors to an integrin and more preferable the alpha 5 beta1 integrin.

As used herein, the term "disease" describes any disease, diseased condition or pathological condition. Such disease may also be defined as abnormal condition, preferably connected with pathological angiogenesis or pathological proliferation and migration of cells. Also, in case of a pathogen, disease means a condition where a pathogen or an unwanted organism is present or present in a concentration or compartment where it is undesired and thus subject to reduction in numbers, removal, elimination, prevention of invasion and/or destruction by using the compounds according to the present invention.

The term "treatment" as used herein comprises both treatment and prevention of a disease. It also comprises follow-up treatment and a combination treatment of a disease. Follow-up treatment is realized upon a treatment of a disease using compounds preferably different from the one according to the present invention, for example, after a failed or insufficient pre-treatment of the targeted disease, such as chemotherapy, anti-hormone therapy, radiation therapy, photodynamic therapy, other anti-angiogenic therapy or surgical treatment. Combination treatment means the treatment of a disease with a compound according to the present invention in combination with another therapeutically active compound or method. Such compounds could be chemotherapeutic agents, anti-hormones, an agent for photodynamic therapy, agents influencing the vascular permeability or anti-angiogenic compounds, like compounds affecting the VEGF activity, or agents affecting the action of other angiogenic growth factors, such as PDGF. Such methods could be radiation therapy, or photodynamic therapy.

The term "inhibition of angiogenesis" preferably means the inhibition of angiogenesis in a tissue in an individual, by administering a compound according to the present invention, whereby the compound interacts with an integrin, preferably alpha5beta1, thereby reducing or inhibiting angiogenesis in the tissue in the individual. Such inhibition provides the reduction of severity of a pathological condition associated with angiogenesis. Inhibition of angiogenesis means also the reduction of the amount of newly formed blood vessels in a tissue in the presence of the compound according to the present invention compared to the tissue in the absence of this compound. Methods for determining the amount of blood vessel formation in a tissue are described in the example and are well known in the art.

The compounds according to the present invention can be characterized by the IC50 value, which is also referred to herein as IC50. The term "IC50" means the inhibition constant, the inhibition of the interaction between the integrin and the most preferred ligand of this integrin. The integrin is preferably alpha5beta1, but for determining the selectivity of the compound, also another integrin can be used. The term "selectivity" preferably means a more than 10-fold and more preferably a 100-fold lower IC50 value for integrin alpha5beta1 in comparison to the other integrins.

The compounds according to the present invention are understood to bind to an integrin thus interfering with the binding of the integrin to a ligand. Preferably such ligand is expressed in the extracellular matrix of a tissue or on a cell surface. The specificity of interaction of the compounds according to the present invention with the integrins, more preferably with integrin alpha5 beta1, also referred to as alpha5beta1, defines the molecular environment where the compounds according to the present invention are active in terms of integrin inhibition and as compounds for the treatment of a disease. Integrins are crucial in mediating a number of biological processes, whereby particularly integrin alpha5 beta1 is an integrin strongly associated with angiogenesis, and even more preferably related to pathological angiogenesis. As used herein, pathological angiogenesis is any angiogenesis which is undesired. An undesired angiogenesis is any angiogenesis which results in a disease or condition which is different from a desired condition, at least from a medical point of view. Additionally alpha5beta1 is also strongly associated with other processes based on pathological migration and proliferation of cells.

However, the mode of action of the compounds according to the present invention is not limited to competitive inhibition of the binding of an integrin and its ligand, but a compound according to the present invention can also change the binding characteristics of the integrin to the ligand and, optionally also vice versa, preferably through a different mechanism, such as an allosteric mechanism upon which either the integrin or the ligand is changed so as to modulate the interaction between the integrin and a ligand thereof. Finally, in principle, the compounds according to the present invention can also induce agonistic effects on integrins (Humphries, 2000, Trends Pharmacol Science, 21, 29). Any of these situations, i.e. an inhibitory as well as a stimulatory situation with regard to the binding of an integrin and a ligand thereof regardless of the particular underlying mode of action, represent an integrin associated state, which can be influenced by the compounds according to the present invention and thus be a reduction or inhibition of angiogenesis or induction of agonistic effects on integrins, as used herein. The term integrin associated state is preferably any of the diseases disclosed herein.

Given the bio distribution of the integrins and particularly of alpha5 beta1 in tissues, organs and cells, respectively and the appearance of pathological angiogenesis, the compounds according to the present invention can be used in the treatment of diseases of or involving various tissues and organs, respectively. Such tissues comprise ocular tissues, such as cornea, retina and macula, the skin, the joints and neoplasms. Further tissues are the synovial tissue, intestinal tissues and the bone tissue.

Based on this, the compounds according to the present invention are preferably used for the treatment of diabetic retinopathy and age related macular degeneration, as an example for diseases related to ocular tissues, preferably age related macular degeneration by neovascularization, for the treatment of skin diseases such as hemangioma and inflammatory diseases from the group comprising psoriasis, gingivitis, arthritic conditions such as rheumatoid arthritis and osteoarthritis, inflammatory bowel diseases, ulcerative colitis, Crohn's disease, and others. It will be acknowledged by the ones skilled in the art that some of the diseases can be grouped into different categories. In so far, the categorization presented is not limiting the actual use of the compounds according to the present invention. Rather, the compounds according to the present invention can be used for the treatment of any of the diseases disclosed herein.

Other ocular diseases contemplated to be treated using compounds according to the present invention are diseases which are connected with choroidal neovascularization such as, e.g., ocular histoplasmosis syndrome, high myopia, angoid streaks, choroidal rupture, optic disc drusen, optic pits, acute posterior multifocal placoid pigment epitheliopathy, serpiginous choroiditis, Harada's disease, Stargard's disease, toxoplasmosis, sarcoidosis, central serous retinopathy, congenital ribella, coloboma, morning glory syndrome, choroidal hemangioma, choroidal melanoma, choroidal nevus, choroidal osteoma, toxocariasis, branch retinal vein occlusion, central retinal vein occlusion, parafoveal telangiectasis, retinitis pigmentosa, Best's disease, adult foveal macular dystrophy, problems after photocoagulation or retinal vascular diseases such as, e.g., hypertensive retinopathy, diabetic retinopathy, sickle cell retinopathy, retinopathy of prematurity, background retinopathy, or other eye diseases connected with neovascularization and/or integrin mediated interactions, such as, e.g., Behçet's disease, cavernous hemangioma of the retina, choroidal rupture, retinal telangiectasia, cystoid maculopathy, Eale's disease, idiopathic central serous choroidopathy, iris neovascularization, malignant choroidal melanoma, preretinal macula fibrosis, ocular histoplasmosis, retinal capillary hemangiomaretinal tumors, tumors of the iris and ciliary body, diseases with pathological corneal neovascularization, pterygiae.

The compounds according to the present invention are also useful in for treatment of neoplasm, whereby the neoplasm is the formation of tumor, which is characterized, in part, by angiogenesis. The neoplasm can be benign such as hemangioma, glioma, teratoma or malignant, whereby the malignant neoplasm may or may not be a metastatic. The malignant neoplasm can be solid tumors, and hematopoeitic cancers such as lymphoma and leukemia. More preferably, the solid tumor is selected from the group comprising carcinoma, sarcoma, osteoma, fibrosarcoma, chondrosarcoma, glioblastoma astrocytoma, neuroblastoma, retinoblastoma, and others.

More preferably, the malignant disorder is selected from the group comprising breast cancer, prostate cancer, cervical cancer, colon cancer, ovarian cancer, brain cancer, lung cancer, pancreatic cancer, gastric cancer, bladder cancer, kidney cancer and head and neck cancer; and sarcomas such as osteosarcoma and Kaposi's sarcoma. Preferably, the lung cancer is non-small.

It is to be understood that the aforementioned diseases are particularly diseases which are based on pathological angiogenesis. However, the compounds according to the present invention are not limited to the use in connection with this kind of diseases but can in alternative embodiments also be used for the treatment of diseases which are generally based on the interaction of integrin with ligands such as fibronectin in the extracellular matrix or on a cell surface. Thereby the compounds are useful in the inhibition of the cell adhesion and migration. The following diseases are currently understood as to be based on this kind of interaction. Accordingly, the compounds according to the present invention may also be used for the treatment of immune based and/or inflammatory diseases, more preferably rheumatoid arthritis, inflammatory bowel disease, Crohn's disease and coronary thrombosis, and infectious diseases which are caused by microbial infection, including fungal infections, bacterial infections and viral infections. Again, it is to be noted, that any of the diseases specifically disclosed herein can be treated by the compound according to the present invention without being limited to the particular mode of action.

In a still further embodiment the immune based and/or inflammatory disease is an autoimmune disease or autoimmune disorder. In a further embodiment, the immune based and/or inflammatory disease is selected from the group comprising rheumatoid arthritis, juvenile arthritis, glomerulonephritis, gingivitis, inflammatory bowel disease, ulcerative colitis, systemic lupus erythematosus associated glomerulonephritis, irritable bowel syndrome, bronchial asthma, multiple sclerosis, pemphigus, pemphigoid, scleroderma, myasthenia gravis, Wegener's Granulomatosis, Churg-Strauss-allergic granulomatosis, scleroderma, Sjögren's syndrome, Sicca syndrome, Goopasture's disease, autoimmune haemolytic and thrombocytopenic states, Goodpasture's syndrome, pulmonary hemorrhage, vasculitis, Crohn's disease, and dermatomyositis.

In a still further embodiment the immune based and/or inflammatory disease is selected from the group comprising inflammation associated with ankylosing spondylitis, burns, lung injury, myocardial infarction, coronary thrombosis, vascular occlusion, post-surgical vascular reocclusion, IgA nephropathy, sarcoidosis, eosinophilic granulomata, midline granuloma, arteritis temporalis, Takayasu's arteritis, pterygia, Kawasaki's disease, atherosclerosis, traumatic central nervous system injury, ischemic heart disease and ischemia-reperfusion injury, acute respiratory distress syndrome, systemic inflammatory response syndrome, multiple organ dysfunction syndrome, tissue graft rejection and hyperacute rejection of transplanted organs.

The compounds according to the present invention are additionally useful in inhibiting pathogenic organisms and are, therefore, useful for treating infectious diseases. Many pathogens interact directly or mediated by extracellular matrix proteins with host cells, causing cell adhesion and invasion of these pathogens. This interaction is mediated by host cell integrins such as alpha5beta1 (Cue, 2000, PNAS, 97, 2858; Frankel, 1996, JBC, 271, 20359; van Putten, 1998, Mol. Microbiology, 29, 369; Finlay, 1997, Microbiol. Mol. Biol. Rev., 61, 136). Additionally pathogens can also express integrins themselves to enter the host cell.

In a preferred embodiment the infectious is selected from the group comprising fungal, viral, bacterial and parasite infection.

Fungal infections contemplated for treatment using the compounds and methods according to the present invention include systemic fungal infections, dermatophytoses and fungal infections of the genito-urinary tract. Fungal infections, preferably systemic fungal infections, include those caused by *Histoplasma, Coccidioides, Cryptococcus, Blastomyces, Paracoccidioides, Aspergillus, Nocardia, Sporothrix, Rhizopus, Absidia, Mucor, Hormodendrum, Phialophora, Rhinosporidium*, and the like. Dennatophyte infections include those caused by *Microsporum, Trichophyton, Epidermophyton, Candida, Pityrosporum*, and the like. Fungal disorders of the genito-urinary tract include infections caused by *Candida, Cryptococcus, Aspergillus, Zygomycodoides*, and the like. Infection by such organisms causes a wide variety of disorders such as ringworm, thrush or candidiasis, San Joaquin fever or Valley fever or coccidiodomycosis, Gilchrist's disease or blastomycosis, aspergillosis, cryptococcosis, histioplasmosis, paracoccidiomycosis, zygomycosis, mycotic keratitis, nail hair and skin disease, Lobo's disease, lobomycosis, chromoblastomycosis, mycetoma, and the like. These infections can be particularly serious, and even fatal, in patients with a depressed immune system such as organ transplant recipients and persons with acquired immunodefficiency syndrome (AIDS). Insofar patient groups which can be treated using the inhibitors according to the present invention are persons with AIDS, particularly those suffering from any of the infectious diseases described herein.

In a further embodiment the bacterial infection is selected from the group comprising infections caused by both Gram-positive and Gram-negative bacteria, including infections caused by *Staphylococcus, Clostridium, Streptococcus, Enterococcus, Diplococcus, Hemophilus, Neisseria, Erysipelothricosis, Listeria, Bacillus, Salmonella, Shigella, Escherichia, Klebsiella, Enterobacter, Serratia, Proteus, Morganella, Providencia, Yersinia, Camphylobacter, Mycobacteria, Helicobacter, Legionalla, Nocardia* and the like.

In a preferred embodiment the bacterial infection causes a wide variety of diseases. Said disorders are selected, among others, from the group comprising pneumonia, diarrhea, dysentery, anthrax, rheumatic fever, toxic shock syndrome, mastoiditis, meningitis, gonorrhea, typhoid fever, brucellis, Lyme disease, gastroenteritis, tuberculosis, cholera, tetanus and bubonic plague.

In another embodiment the disease is a viral infection, more particularly a viral infection caused by a virus selected from the group comprising retrovirus, HIV, Papilloma virus, Epstein-Barr, Herpes virus, Hepatitis virus, Papova virus, Influenza virus, Rabies, JC, encephalitis causing virus, hemorrhagic fever causing virus such as Ebola Virus and Marburg Virus.

In a further embodiment the parasite infection is selected from the group comprising infections caused by *Trypanosoma, Leishmania, Trichinella, Echinococcus, Nematodes,*

Classes Cestoda, Trematoda, Monogenea, Toxoplasma, Giardia, Balantidium, Parameciunm, Plasmodium or Entamoeba.

The compounds according to the present invention are useful in inhibiting and thus in the treatment of diseases involving or comprising undesired cell proliferation, including but not limited to proliferative disorders in ocular tissues such as proliferative vitreoretinopathy.

In case the disease is a non-neoplastic cell proliferative disorder, it is preferably selected from the group comprising fibrotic disorder. Preferably, the fibrotic disorder is fibrosis.

The disease may also be a non-neoplastic cell proliferative disorder which is selected from the group comprising prostatic hypertrophy, preferably benign prostatic hypertrophy, endometriosis, uterine fibroid, keloid scar formation, scleroderma, psoriasis, tissue repair and wound healing.

Fibrotic disorders which may be treated using the compounds according to the present invention are generally characterized by inappropriate overproliferation of non-cancerous fibroblasts. Examples thereof include fibromyalgia, fibrosis, more particularly cystic, hepatic, idopathic pulmonary, and pericardial fibrosis and the like, cardiac fibromas, fibromuscular hyperplasia, restenosis, atherosclerosis, fibromyositis, and the like.

In a further embodiment the compounds according to the present invention can be used as agonistic effectors on integrin thus promoting neovascularisation. Accordingly, the compounds according to the present invention are used in a preferred embodiment for the treatment of diseases which require or are treated by neovascularization or induction thereof. This kind of disease is a disease which can be selected from the group comprising wound healing, stroke, infertility, ulcer, scleroderma, and coronary heart disease.

In connection with the use of the compounds according to the present invention it seems that those compounds having a particular substitution pattern are particularly effective in being used for the treatment of any disease which is characterized by an undesired cell growth such as neoplasms and more preferably carcinoma and others which are particularly effective in the treatment of macular degeneration, preferably macular degeneration by neovascularization.

Compounds according to the present invention which are particularly useful in the treatment of undesired cell growth exhibit a moiety A, whereby A is selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl and substituted alkylthio-cycloalkyl, benzyl, substituted benzyl, phenyl, substituted phenyl, heterocyclyl, substituted heterocyclyl, aryl, substituted aryl, heterocyclyl, substituted heterocyclyl, arylalkyl substituted arylalkyl, heteroarylalkyl, substituted heteroarylalkyl, cycloalkylalkyl, substituted cycloalkylalkyl, heterocyclylalkyl substituted heterocyclylalkyl, alkyloxy-heterocyclyl substituted alkyloxy-heterocyclyl, alkyloxy-aryl, substituted alkyloxy-aryl, alkyloxy-heteroaryl, substituted alkyloxy-heteroaryl, arylthio-alkyl, substituted arylthio-alkyl, arylthio-cycloalkyl and substituted arylthio-cycloalkyl.

In a more preferred embodiment such kind of compound R2 is additionally or alternatively selected from the group comprising benzyl, substituted benzyl, phenyl, substituted phenyl, heterocyclyl, substituted heterocyclyl, aryl, substituted aryl, heterocyclyl, substituted heterocyclyl, arylalkyl substituted arylalkyl, heteroarylalkyl, substituted heteroarylalkyl, cycloalkylalkyl, substituted cycloalkylalkyl, heterocyclylalkyl substituted heterocyclylalkyl, alkyloxy-heterocyclyl substituted alkyloxy-heterocyclyl, alkyloxy-aryl, substituted alkyloxy-aryl, alkyloxy-heteroaryl, substituted alkyloxy-heteroaryl, arylthio-alkyl, substituted arylthio-alkyl, arylthio-cycloalkyl and substituted arylthio-cycloalkyl.

In an even more preferred embodiment such kind of compounds comprises either alternatively, in addition to or in any combination with R2 and A a residue Q of B, wherein Q is $C=O$ or $SO_2$.

Compounds according to the present invention which are particularly useful in the treatment of macular degeneration exhibit a moiety A, whereby A is selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl and substituted alkylthio-cycloalkyl, benzyl, substituted benzyl, phenyl, substituted phenyl, heterocyclyl, substituted heterocyclyl, aryl, substituted aryl, heterocyclyl, substituted heterocyclyl, arylalkyl substituted arylalkyl, heteroarylalkyl, substituted heteroarylalkyl, cycloalkylalkyl, substituted cycloalkylalkyl, heterocyclylalkyl substituted heterocyclylalkyl, alkyloxy-heterocyclyl substituted alkyloxy-heterocyclyl, alkyloxy-aryl, substituted alkyloxy-aryl, alkyloxy-heteroaryl, substituted allyloxy-heteroaryl, arylthio-alkyl, substituted arylthio-alkyl, arylthio-cycloalkyl and substituted arylthio-cycloalkyl.

In a more preferred embodiment such kind of compound R2 is additionally or alternatively selected from the group comprising alkyl and substituted alkyl, cycloalkyl, substituted cycloalkyl, alkyloxy-alkyl, substituted alkyloxy-alkyl, alkyloxy-cycloalkyl, substituted alkyloxy-cycloalkyl, alkylthio-alkyl, substituted alkylthio-alkyl, alkylthio-cycloalkyl and substituted alkylthio-cycloalkyl.

In an even more preferred embodiment such kind of compounds comprises either alternatively, in addition to or in any combination with R2 and A a residue Q of B, wherein Q of B is $C=O$ or $SO_2$.

It is also within the present invention that the compounds according to the present invention may be used for the treatment of a patient suffering from a disease or diseased condition as defined above. Such treatment comprises the administration of one or several of the compounds according to the present invention or a medicament or pharmaceutical composition described herein.

Toxicity and therapeutic efficacy of a compound can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages suitable for use in humans. The dosage may vary within this range depending upon a variety of factors, e.g., the dosage form employed, the route of administration utilized, the condition of the subject, and the disease, which has to be treated.

For any compound according to the present invention, the therapeutically effective dose can be estimated initially from protein binding and cell culture assays by determining an $IC_{50}$ (i.e., the concentration of the test substance which achieves a half-maximal inhibition of integrin binding or cell adhesion). A dose can then be formulated in animal models to achieve a circulating concentration range in plasma or other compartments such as, e.g., vitreous humor, synovial liquid or other, that includes the $IC_{50}$ as determined in binding assays. Such information can be used to more accurately determine useful doses in humans. Levels in plasma or other compartments may be measured, for example by HPLC, LC/MS, or ELISA.

It should be noted that the attending physician would know how to and when to terminate, interrupt, or adjust administration due to toxicity, to organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient. Typically, the dose will be between about 0.0001-100 mg/kg of body weight or 1 ng-1 mg per eye or comparable concentrations for other compartments. About 0.001 mg to about 50 mg will preferably be administered to a child, and between 0.01 mg and about 1000 mg will preferably be administered to an adult.

A program comparable to that discussed above may be used in veterinary medicine. The exact dose will depend on the disorder to be treated and will be ascertainable by one skilled in the art using known techniques.

Depending on the specific conditions to be treated, such compounds may be formulated and administrated systemically or locally. Techniques for formulation and administration may be found in "Remington's Pharmaceutical Sciences", 1990, 18$^{th}$ ed., Mack Publishing Co., Easton, Pa. The administration of a compound according to the present invention can be done in a variety of ways, including, but not limited to, orally, subcutaneously, intravenously, intranasally, transdermally, intraperitoneally, intramuscularly, intrapulmonary, vaginally, rectally, or intraocularly, periocularly, intraorbitally, intracapsulary, intrasynovially, intracisternally, topically, just to name a few. In some instances, for example, in the treatment of wounds and inflammation, the compound according to the present invention may be directly applied as a ointment, powder, solution or spray. Topical administration also comprises passive or facilitated adsorption, preferably through the skin, including skin patches and iontophoresis.

Depending on the route of administration some formulations are particularly advantageous. In case of administration of the compound to the eye the following formulations are preferred. In case of local administration, intraocular or periocular injection, local implants, drops and ointments are preferred. In case of systemic administration, injection and oral administration are preferred. In case of intraocular injection intravitreal, intracameral or sub-retinal injections are preferred. Periocular injections are selected from group comprising subconjunctival, para/retro bulbar, juxtascleral, subtenual, and others. In the case of local implants specialized sustained-release devices will be administered intraocular or periocular, to enable a constant, slow release of compound to the eye (Robinson, 2002, Exp. Eye Res, 74, 309; Geroski, 2000, 41, 961), other sustained release systems are microspheres, liposomes, nanoparticles or other polymer matrices (Bourlais, 1998, Prog. Retin Eye Res. 17, 33). In order to improve the stability and pharmacological properties of the compound for ocular administration, compound could be modified, as described before, and/or administered in combination with a special formulation, addition of penetration enhancers, bioadhesives and/or biodegradable polymers (Clark, 2003, Nature Rev. Drug Discovery, 2, 448; Sasaki, 1999, Crit Rev Ther Drug Carrier Syst., 16, 85; Kauer, 2002, Drug Dev Ind Pharm., 28, 473; Kimura, 2001, Ophthalmologica, 215, 143). An example for a sustained release of compound in the eye is the preparation of a dry compound pellet which will be coated with a silicone layer, after implantation into the eye the pharmaceutically active compound will be released constantly over a long period of time (Robinson, 2002, Exp. Eye Res, 74, 309).

In a further aspect the present invention is related to a medicament or a pharmaceutical composition comprising at least one active compound and at least one pharmaceutically acceptable carrier, excipient or diluent. As used herein, the active compound is a compound according to the present invention, a pharmaceutically salt or base thereof or a prodrug thereof, if not indicated to the contrary.

For injection, compounds of the invention may be formulated in aqueous solution, preferably in physiologically compatible buffers such as Hank's solution, Ringer's solution, or physiologically saline buffer. For transmucosal administration, penetrants appropriate to the barrier to be permeated are used in the formulation. Such penetrants are generally known in the art.

The use of pharmaceutical acceptable carriers to formulate the compounds according to the present invention into dosages or pharmaceutical compositions suitable for systemic administration is within the scope of the present invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for oral administration. Such carriers enable the compounds according to the present invention to be formulated as tablets, pills, capsules, dragees, liquids, gels, syrups, slurries, suspensions and the like, for oral ingestion by a subject to be treated.

Compounds according to the present invention or medicaments comprising them, intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Delivery systems involving liposomes are disclosed in International Patent Publication No. WO 91/19501, as well as U.S. Pat. No. 4,880,635 to Janoff et al. The publications and patents provide useful descriptions of techniques for liposome drug delivery and are incorporated by reference herein in their entirety.

Pharmaceutical compositions comprising a compound according to the present invention for parenteral administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil or castor oil, or synthetic fatty acid esters, such as ethyl oleate or triglycerides, or liposomes. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions.

Pharmaceutical compositions comprising a compound according to the present invention for oral use can be obtained by combining the active compound(s) with solid excipient, optionally grinding the resulting mixture, and processing the mixture of granules, after adding suitable auxiliaries, if desired, to obtain tablets or dragee cores.

Suitable excipients are, in particular, fillers such as sugars, including lactose, sucrose, mannitol, sorbitol, and the like; cellulose preparations, such as, for example, maize starch wheat starch, rice starch, potato starch, gelatin, gum tragacanth, methyl cellulose, hydroxypropylmethyl cellulose, sodium carboxymethyl cellulose, polyvinylpyrrolidone (PVP) and the like, as well as mixtures of any two or more thereof. If desired, disintegrating agents may be added, such as cross-linked polyvinyl pyrrolidone, agar, alginic acid or a salt thereof such as sodium alginate, and the like.

Dragee cores as a pharmaceutical composition comprising a compound according to the present invention are provided with suitable coatings. For this purpose, concentrated sugar solutions may be used, which may optionally contain gum arabic, talc, polyvinyl pyrrolidone, carbopol gel, polyethylene glycol, titanium dioxide, lacquer solutions, suitable organic solvents or solvent mixtures, and the like. Dyestuffs or pigments may be added to the tablets or dragee coatings for identification or to characterize different combinations of active compound doses.

Pharmaceutical preparations comprising a compound according to the present invention which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

A "patient" for the purposes of the present invention, i.e. to whom a compound according to the present invention or a pharmaceutical composition according to the present invention is administered, includes both humans and other animals and organisms. Thus the compounds, pharmaceutical compositions and methods are applicable to or in connection with both human therapy and veterinary applications including diagnostic(s), diagnostic procedures and methods as well as staging procedures and methods. For example, the veterinary applications include, but are not limited to, canine, bovine, feline, porcine, caprine, equine, and ovine animals, as well as other domesticated animals including reptiles, such as iguanas, turtles and snakes, birds such as finches and members of the parrot family, lagomorphs such as rabbits, rodents such as rats, mice, guinea pigs, monkeys, hamsters, amphibians, fish, and arthropods. Valuable non-domesticated animals, such as zoo animals, may also be treated. In the preferred embodiment the patient is a mammal, and in the most preferred embodiment the patient is human.

The pharmaceutical composition according to the present invention comprises at least one compound according to the present invention in a form suitable for administration to a patient. Preferably, a compound according to the present application is in a water soluble form, such as being present as a pharmaceutically acceptable salt, which is meant to include both acid and base addition salts which are also generally referred to herein as pharmaceutically acceptable salts. "Acid addition salt", and more particularly "pharmaceutically acceptable acid addition salts" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Base addition salts" and more particularly "pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The pharmaceutical compositions according to the present invention may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The compounds according to the present invention are, in a further embodiment, administered to a subject either alone or in a pharmaceutical composition where the compound(s) is mixed with suitable carriers or excipient(s). In treating a subject, a therapeutically effective dose of compound (i.e. active ingredient) is administered. A therapeutically effective dose refers to that amount of the active ingredient that produces amelioration of symptoms or a prolongation of survival of a subject which can be determined by the one skilled in the art doing routine testing.

In an embodiment of the various aspects of the present invention, a compound according to the present invention is administered together with a further pharmaceutically active compound. More preferably, such further pharmaceutically active compound is selected from the group comprising chemotherapeutic agents such as, e.g., 5-fluorouracil, gemcitabine, carboplatin, paclitaxel, cisplatin, taxol, oxaliplatin, irinotecan and others, agents for anti-hormone therapy such as, e.g., acetate, tamoxifen and others, agents for photodynamic therapy, agents influencing the vascular permeability and/or angiogenesis such as, e.g., COX2-inhibitors, NO-synthase inhibitors, bradykinin receptor antagonists or others, or anti-angiogenic compounds, like compounds affecting VEGF activity (like VEGF or VEGF-receptor antibodies, soluble VEGF-receptor fragments, VEGF-receptor-kinase inhibitors), or other agents affecting the action of angiogenic growth factors. The combination of compounds effecting different steps of angiogenic pathway or targeting different mechanism, which causes the diseases, could be beneficial for an optimal treatment of disease According to the present invention the compounds disclosed herein, referred to as compounds according to the present invention, may be used as a medicament or for the manufacture of medicament or in a method of treatment of a patient in need thereof. Insofar any of these compounds constitute a pharmaceutical compound. The use of this kind of compound also comprises the use of pharmaceutically acceptable derivatives of such compounds.

In addition, the compounds according to the present invention may be transformed upon application to an organism such as a patient, into the pharmaceutically active compound. Insofar the compounds according to the present invention may be prodrugs which, however, are nevertheless used for the manufacture of the medicaments as disclosed herein given the fact that at least in the organism they are changed in a form which allows the desired It is to be understood that any of the pharmaceutical compositions according to the present invention may be used for any of the diseases described herein.

The pharmaceutical compositions according to the present invention may be manufactured in a manner that is known as such, e.g., by means of conventional mixing, dissolving, granulating, dragee-mixing, levigating, emulsifying, encapsulating, entrapping, lyophilizing, processes, or the like.

In a further aspect, the present invention is related to the use of the compounds according to the present invention as a diagnostic means. As used herein, a diagnostic means is the same as a diagnostic or a diagnostic tool. More preferably, the compounds according to the present invention can be used for the manufacture of such diagnostic.

This use of the compounds according to the present invention is particularly based on the fact that said compounds interact specifically with integrins, more particularly integrin alpha5 beta1. Because of the very restricted expression of alpha5beta1 on activated endothelial cell in tumors and after stimulation with growth factors (Kim, 2000, Am. J. Path, 156, 1345; Collo, 1999, J. Cell Sc., 112, 569), this molecule is a suitable marker for angiogenesis in pathological conditions.

In preferred embodiments, the compounds according to the present invention are labeled compounds according to the present invention. The label is preferably a detectable label and allows the use of the respective compounds particularly in the performance of in vivo imaging methods such as radionuclide imaging, positron emission tomography, computerized axial tomography and magnetic resonance imaging. Most preferably, a radionuclide or a paramagnetic material is used as a label in the aforementioned methods. Additionally the specific interaction of the compound with the integrin could be also detected ex vivo e.g. on isolated cells and in tissues removed by biopsy.

The problem underlying the present invention is also solved by the technical teaching according to the attached independent claims. Preferred embodiments thereof may be taken from the dependent claims.

The invention is now further illustrated by reference to the following figures and examples from which further advantages, features and embodiments may be taken. It is understood that these examples are given for purpose of illustration only and not for purpose of limitation. All references cited herein are incorporated by reference.

Figure 1:
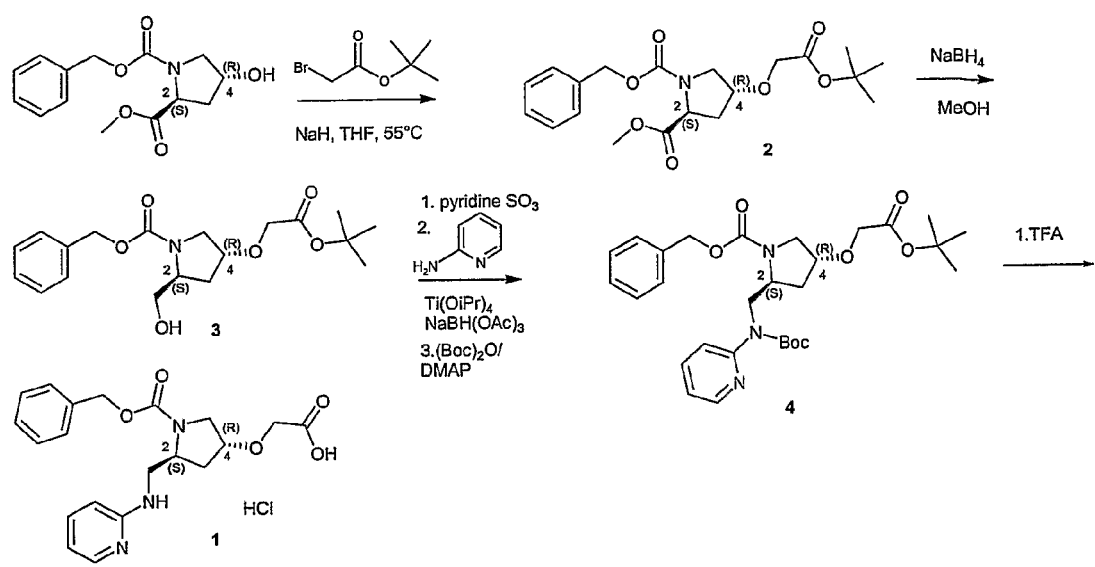
FIG. 1 shows a reaction scheme for the synthesis of 2S,4R-4-carboxymethoxy-2-(pyridin-2-ylaminomethyl)-pyrrolidine-1-carboxylic acid benzyl ester (1).

In order that the invention herein described may be more fully understood, the following detailed description is set forth. As used herein, the following abbreviations are used:
AIDS Acquired immunodefficiency syndrome
AMD Age related macular degeneration
bFGF Basic fibroblast growth factor
Boc tert.-Buthoxycarbonyl
BSA Bovine serum albulmin
CD31 Endothelial cell marker-platelet/endothelial cell adhesion molecule
Cox Cyclooxygenase
Cpd. Compound
d Doublet
DCM Dichloromethan
DIC Diisopropylcarbodiimide
DIPEA N,N-Diisopropylethylamine
DMF N,N-Dimethylformamide
DMSO Dimethylsulfoxid
DMSZ Deutsche Sammlung von Mikroorganismen und Zellkulturen
EC Endothelial cells
ECM extracellular matrix
EDTA ethylenediaminetetra-acetate
ELISA Enzyme-linked immunosorbent assay
eq. equivalent(s)
Fc Fragment of constant region of human immunoglobuline G1
FITC Fluorescein isothiocyanate
Fmoc 9-Fluorenylmethyloxycarbonyl
h Hour
HBTU O-(Benzotriazol-1-yl)-1,1,3,3-tetramethyluronium-Hexafluorophosphat
Hepes N-2-Hydroxyethylpiperazine-N'-2-ethanesulfonic acid
HIV Human immuno-deficiency virus
HPLC high-pressure liquid chromatography
HRP Horseradish peroxidase
LC/MS Liquid chromatography-mass spectrometry
m Multiples
Me Methyl
MES 2-(N-Morpholino)-ethanesulfonic acid
min Minute(n)
mL Milliliter
MTBE Methyl-tert-buthyl ether
NMR nuclear magnetic resonance
NO Nitric oxide OD Optical density
PBS Phosphate buffered saline
PMA Phorbol 12-myristate 13-acetate
PDR Diabetic retinopathy
PVP polyvinylpyrrolidone
PDGF Platelet derived growth factor
PIDA Iodbenzol-diacetate
RGD Arginine-glycine-aspartate
RPE Retinal pigment epithelium
RPMI Medium developed at Roswell Park Memorial Institute
RT Room temperature
s Singulett
$^t$Bu tert-Butyl
TFA Trifluoroacetic acid
THF Tetrahydrofuran
TIBS Tributhylsilane
TMB 3.3.5.5'-tetramethylethylenediamine
Tris Tris(hydroxymethyl)-aminomethane
TRITC Tetramethylrhodamine isothiocyanate
VEGF Vascular endothelial growth factor The following materials in methods were used to in the described examples.

Solvents:

Solvents were used in the assigned quality without further purification.

Acetonitril (Gradient grade, J.T. Baker); dichlormethan (for synthesis, Merck Eurolab); diethylether (for synthesis, Merck Eurolab); N,N-dimethylformamide (LAB, Merck Eurolab); dioxan (for synthesis, Aldrich); methanol (for synthesis, Merck Eurolab).

Water:

Milli-Q Plus, Millipore, demineralized.

Chemicals:

Were purchased from Advanced ChemTech (Bamberg, Deutschland), Sigma-Aldrich-Fluka (Deisenhofen, Deutschland), Bachem (Heidelberg, Deutschland), J.T. Baker (Phillipsburg, USA), Lancaster (Mühlheim/Main, Deutschland), Merck Eurolab (Darmstadt, Deutschland), Neosystem (Strassburg, Frankreich), Novabiochem (Bad Soden, Deutschland, ab 2003 Merck Biosciences, Darmstadt, Deutschland) und Acros (Geel, Belgien, Vertriebsgesellschaft Fisher Scientific GmbH, Schwerte, Deutschland), Peptech (Cambridge, Mass., USA), Synthetech (Albany, Oreg., USA), Pharmacore (High Point, N.C., USA), Anaspec (San Jose, Calif., USA) and used in the assigned quality without further purification.

Plastic ware for biochemical assays were purchased from Greiner Bio-one (Germany), Nunc (Nalge Europe Ltd)

EXAMPLE 1

2S,4R-4-carboxymethoxy-2-(pyridin-2-ylaminomethyl)-pyrrolidine-1-carboxylic acid benzyl ester (1)

The synthesis of the title compound is depicted in FIG. 1 a) Synthesis of 2S,4R-4-tert-butoxycarbonyl-methoxy-pyrrolidine-1,2-dicarboxylic acid 1-benzyl ester 2-methyl ester (2)

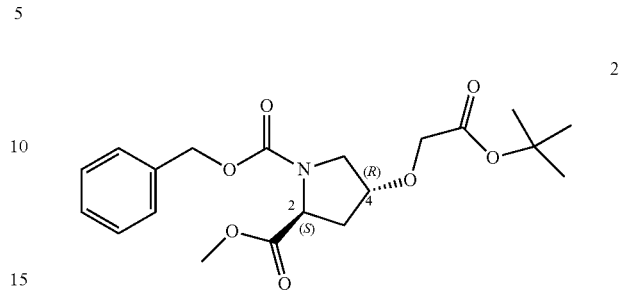

4.8 g (120 mmol) of NaH (60% in paraffin) were suspended under Ar in 50 mL of absolute THF and cooled down to 0° C. 16.8 g (60 mmol) of Z-Hyp-OMe, dissolved in 100 mL of absolute THF, were added slowly to the reaction mixture and stirred for 30 min at 0° C. 41 mL (278 mmol) of tert-butyl bromoacetate were added to the suspension and the reaction mixture was heated up to 55° C. stirred for 12 h. After addition of 7.5 mL of THF/H$_2$O (1:1), the reaction mixture was dried with Na$_2$SO$_4$ and the precipitate was filtered off. The solvent was removed at the evaporator and the crude reaction mixture was taken up in 200 mL of MeOH. The paraffin oil was removed. After evaporation of the solvent the crude product was chromatographed on silica gel using ethyl acetate/hexane.

Yield 12.91 g (77%). NMR-$^1$H (DMSO-d$_6$): δ=7.42-7.24 (m, 5H), 5.09 (s, 2H), 4.96 (d, 1H, J=9.6), 4.31 (dt, 1H, J=16.1, 7.8), 4.18 (m, 1H), 3.65 (s, 2H), 3.54 (s, 3H), 3.54 (dt, 1H, J=4.4, 11.7), 2.37 (m, 1H), 2.00 (m, 1H), 1.42 (s, 9H). NMR-$^{13}$C (DMSO-d$_6$) (partial signal doubling due Cbz-rotameres): δ=172.6 (C$_q$), 172.3 (C$_q$), 169.4 (C$_q$), 154.1 (C$_q$), 153.5 (C$_q$), 136.7 (C$_q$), 136.5 (C$_q$), 128.5 (CH), 128.4 (CH), 128.3 (CH), 127.9 (CH), 127.8 (CH), 127.5 (CH), 127.3 (CH), 80.8 (C$_q$), 77.63 (CH$_2$), 76.8 (CH$_2$), 69.2 (CH), 66.2 (CH$_2$), 66.2 (CH$_2$), 57.7 (CH$_2$), 57.3 (CH$_2$), 52.2 (CH$_2$), 52.0 (CH$_2$), 5.18 (CH), 35.8 (CH$_2$), 34.9 (CH$_2$), 27.7 (CH$_3$). LCMS: m/z: 394.5 [M$^+$].

b) Synthesis of 2S,4R-4-tert-butoxycarbonyl-methoxy-2-hydroxymethyl-pyrrolidine-1-carboxylic acid benzyl ester (3)

5 g (12.71 mmol) of 2 were dissolved in 70 mL of MeOH and 10.08 g (266.91 mmol) of NaBH$_4$ were added in small portions over a period of 6 h. The reaction mixture was stirred over night and the solvent was removed at the evaporator. The crude reaction mixture was taken up in 150 mL of ethyl acetate and extracted with saturated NaHCO$_3$ and NaCl solution. The organic layer was dried over Na$_2$SO$_4$ and the solvent was removed at the evaporator.

Yield 2.85 g (58%). NMR-$^1$H (DMSO-d$_6$): δ=7.40-7.28 (m, 5H), 5.05 (s, 2H), 4.73 (m, 1H), 4.13 (m, 1H), 3.97 (s, 2H), 3.84 (m, 1H), 3.60-3.29 (m, 4H), 2.00 (m, 2H), 1.41 (s, 9H). NMR-$^{13}$C (DMSO-d$_6$) partial signal doubling due to Cbz-rotameres): δ=169.4 (C$_q$), 154.2 (C$_q$), 137.0 (C$_q$), 128.3 (CH), 127.7 (CH), 127.5 (CH), 127.4 (CH), 127.4 (CH), 80.7 (C$_q$), 77.6 (CH$_2$), 77.0 (CH$_2$), 67.4 (CH), 65.9 (CH$_2$), 65.7 (CH$_2$), 66.2 (CH$_2$), 61.2 (CH$_2$), 59.7 (CH), 57.8 (CH$_2$), 57.2 (CH$_2$), 52.4 (CH$_2$), 52.0 (CH$_2$), 27.7 (CH$_3$). LCMS: m/z: 366.4 [M$^+$].

c) Synthesis of 2S,4R-4-tert-butoxycarbonyl-methoxy-2-[(tert-butoxycarbonyl-pyridin-2-yl-amino)-methyl]-pyrrolidine-1-carboxylic acid benzyl ester (4)

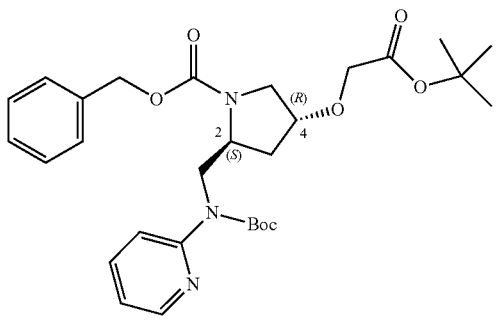

4

7.2 g (19.8 mmol) of 3 and 44 mL (317 mmol) of NEt$_3$ were dissolved in 300 mL of DCM/DMSO (v/v=3/1) and cooled to 0° C. 47.3 g (297.2 mmol) of SO$_3$-pyridine-complex were added and the reaction mixture was stirred for 40 min. DCM was removed at the evaporator and the crude reaction mixture was poured into 500 mL of ethyl acetate. The organic layer was extracted with H$_2$O, saturated NaHCO$_3$ and NaCl solution. The organic layer was dried over Na$_2$SO$_4$ and the solvent was removed at the evaporator.

The crude reaction mixture was dissolved in 500 mL of dichloroethane and 2.24 g (23.76 mmol) of 2-aminopyridine and 7.1 mL (29.78 mmol) of Ti(OiPr)$_4$ were added. After 30 min 29.4 g (138.6 mmol) of NaBH(OAc)$_3$ were added and the reaction was stirred for 4 h. 10 mL of saturated NaHCO$_3$ were added, the reaction mixture was dried with Na$_2$SO$_4$ and the precipitate was filtered of. The solvent was removed at the evaporator and the crude reaction mixture was taken up in 150 mL of absolute THF. 12.9 g (59.4 mmol) of (BocO)$_2$O and 200 mg DMAP were added. After 12 h of stirring at room temperature 4.3 g (19.8 mmol) of (BocO)$_2$O and 1.7 mL (9.9 mmol) of DIPEA were added and reaction mixture was stirred for 12 h. After removal of the solvent at the evaporator the crude product was chromatographed on silica gel using ethyl acetate/hexane.

Yield 5.17 g (51%). NMR-$^1$H (DMSO-d$_6$): δ=8.29 (dd, 1H, J=3.9, 13.2), 7.70 (t, 1H, J=7.3), 7.46 (dd, 1H, J=4.4, 7.8), 7.39-7.23 (m, 5H), 7.10 (dd, 1H, J=4.9, 7.3), 5.05-4.84 (m, 2H), 4.25-4.04 (m, 4H), 3.94 (s, 2H), 3.44 (t, 1H, J=12.2), 3.21 (dd, 1H, J=4.9, 11.7), 1.92 (m, 2H), 1.43 (s, 9H), 1.40 (s, 3H). NMR-$^{13}$C (DMSO-d$_6$) (partial signal doubling due to Cbz-rotameres): δ=169.3 (C$_q$), 160.1 (C$_q$), 154.1 (C$_q$), 153.6 (C$_q$), 147.3 (CH), 137.0 (CH), 136.9 (C$_q$), 128.3 (CH), 127.7 (CH), 127.4 (CH), 120.4 (CH), 120.0 (CH), 80.7 (C$_q$), 80.6 (C$_q$), 80.4 (C$_q$), 77.6 (CH), 77.0 (CH), 66.2 (CH$_2$), 65.7 (CH$_2$), 55.4 (CH), 54.9 (CH), 51.4 (CH$_2$), 51.2 (CH$_2$), 48.3 (CH$_2$), 48.2 (CH$_2$), 34.6 (CH$_2$), 33.7 (CH$_2$), 27.7 (CH$_2$), (CH$_3$). LCMS: m/z: 542.4 [M$^+$].

d) Synthesis of 2S,4R-4-carboxymethoxy-2-(pyridin-2-ylaminomethyl)-pyrrolidine-1-carboxylic acid benzyl ester (1)

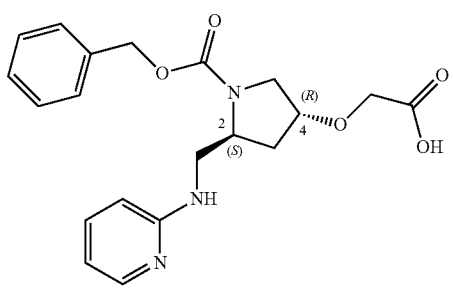

1

400 mg (0.74 mmol) of 4 were dissolved in 5 mL of TFA and stirred for 1 h at room temperature. The solvent was removed at the evaporator and the crude product was freeze dried using 0.5M HCl and ACN/H$_2$O.

Yield 328 mg (105%, HCl-salt). NMR-$^1$H (DMSO-d$_6$): δ=8.87 (s, broad, 1H), 8.01-7.82 (m, 2H), 7.34 (m, 5H), 7.17 (t, 1H, J=8.8), 7.02-6.78 (s, 2H), 5.07 (m, 2H), 4.23-4.08 (m, 2H), 4.02 (s, 2H), 3.74-3.34 (m, 4H), 2.20 (m, 1H), 1.92 (m, 1H). NMR-$^{13}$C (DMSO-d$_6$) (partial signal doubling due Cbz-rotameres): δ=171.5 (C$_q$), 171.3 (C$_q$), 154.9 (C$_q$), 154.5 (C$_q$), 153.1 (C$_q$), 152.9 (C$_q$), 136.7 (C$_q$), 136.5 (C$_q$), 128.7 (CH), 128.6 (CH), 128.3 (CH), 128.2 (CH), 127.7 (CH), 127.6 (CH), 127.3 (CH), 112.6 (CH), 111.9 (CH), 85.9 (CH), 77.2 (CH), 77.0 (CH), 66.0 (CH$_2$), 65.5 (CH$_2$), 55.0 (CH), 54.4 (CH), 51.8 (CH$_2$), 49.8 (CH$_2$), 46.2 (CH$_2$), 44 (CH$_2$), 34.2 (CH$_2$), 33.9 (CH$_2$). LCMS: m/z: 386.3 [M$^+$].

EXAMPLE 2

Synthesis of 12S,14R,30S-4-{[2-Carboxy-2-(2,4,6-trimethyl-benzenesulfonylamino)-ethylcarbamoyl]-methoxy}-2-(pyridin-2-ylaminomethyl)-pyrrolidine-1-carboxylic acid benzyl ester (5)

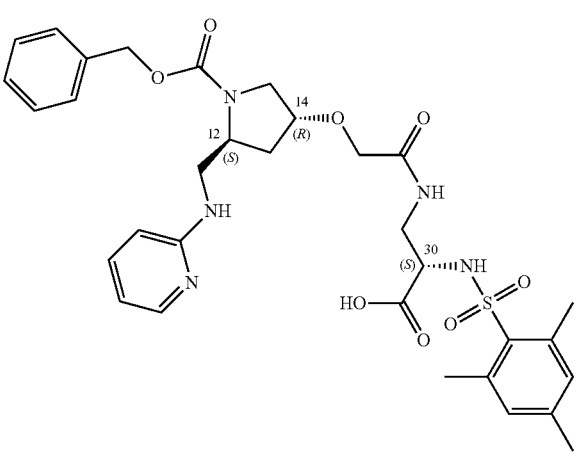

5

17 mg (0.04 mmol) of 1 as prepared in example 1, 14 mg (0.0409 mmol) of 3S-3-amino-2-(2,4,6-trimethyl-benzene-sulfonylamino)-propionic acid tert-butyl ester, 20 mg (0.0409 mmol) of HBTU and 16 mL (0.12 mmol) of DIPEA were dissolved in 2 mL of DMF and stirred for 2 h. The solvent was removed at the evaporator and the crude product was purified by HPLC. The product was dissolved in 2 mL of TFA and stirred for 2 h at room temperature. After evaporation of the TFA the crude product was freeze dried using ACN/H$_2$O.

Yield 14.4 mg (47%, TFA-salt) NMR-$^1$H (DMSO-d$_6$): δ=8.59 (s, broad, 1H) 7.94 (d, 1H, J=8.8), 7.94 (s, broad, 1H), 7.70 (t, 1H, J=5.8), 7.35 (s, broad, 3H), 7.31 (s, broad, 2H), 7.11 (d, 1H, J=9.2), 6.96 (s, 2H), 6.92-6.76 (m, 2H), 5.09 (s, 2H), 5.02 (t, 1H, J=12.2), 4.11 (s, broad, 2H), 3.88-3.35 (m, 8H) 2.52 (s, 6H), 2.22 (s, 3H), 1.89 (m, 1H). NMR-$^{13}$C (DMSO-d$_6$): δ=171.2 (C$_q$), 169.2 (C$_q$), 153.3 (C$_q$), 141.3 (C$_q$), 138.4 (C$_q$), 136.7 (C$_q$), 134.5 (C$_q$), 131.4 (CH), 128.4 (CH), 127.8 (CH), 127.5 (CH), 112.1 (CH), 77.2 (CH), 73.2 (CH$_2$), 67.5 (CH$_2$), 66.4 (CH$_2$), 66.1 (CH$_2$), 55.0 (CH), 54.3 (CH), 51.6 (CH$_2$), 44.0 (CH$_2$), 22.5 (CH$_3$), 20.3 (CH$_3$). LCMS: m/z: 654.6 [M$^+$].

EXAMPLE 3

Synthesis of 12S,14R,30S-4-(2-{[2-tert-butoxycarbonyl-2-(2,4,6-trimethyl-benzenesulfonyl-tert-Butoxycarbonyl-amino)-2-(tert-Butoxycarbonyl)-ethyl]-amino}-2-oxo-ethoxy)-2-[(tert-butoxycarbonyl-pyridin-2-yl-amino)-methyl]-pyrrolidine-1-carboxylic acid benzyl ester (6)

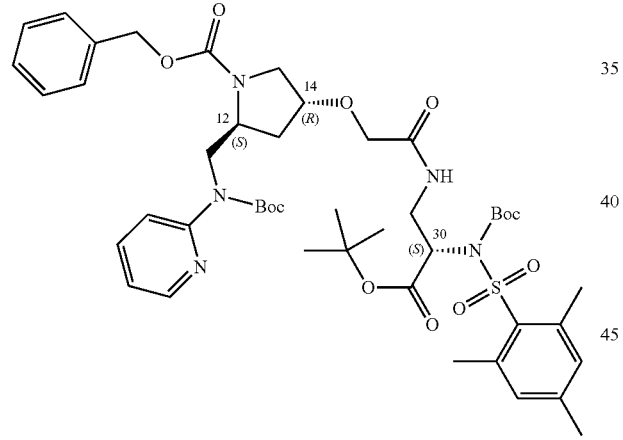

6

3 g (7.1 mmol) of 1 as prepared in example 1, 2.67 g (7.8 mmol) of 3S-3-amino-2-(2,4,6-trimethyl-benzenesulfonylamino)-propionic acid tert-butyl ester, 3.26 g (7.8 mmol) of HBTU and 4.5 mL (31.2 mmol) of DIPEA were dissolved in 50 mL of DMF and stirred for 2.5 h. The solvent was removed at the evaporator and the crude product was taken up in 600 mL of ethyl acetate. The organic layer was extracted with saturated NaHCO$_3$ and NaCl solution, dried with Na$_2$SO$_4$ and the solvent was removed at the evaporator. The crude reaction mixture was taken up in 100 mL of absolute THF. 2.77 g (59.4 mmol) of (BocO)$_2$O and DMAP were added. After 3 days at room temperature additional 0.92 g (4.2 mmol) of (BocO)$_2$O and after 1 day additional 1.84 g (8.5 mmol) of (BocO)$_2$O were added and stirred for 24 h. The solvent was removed at the evaporator and the crude product was taken up in 500 mL of ethyl acetate. The organic layer was extracted with saturated NaHCO$_3$ and NaCl solution, dried with Na$_2$SO$_4$ and the solvent was removed at the evaporator. The crude product was chromatographed on silica gel using ethyl acetate/hexane.

Yield 3.11 g (48%). NMR-$^1$H (DMSO-d$_6$): δ=8.27 (dd, 1H, J=3.4, 13.2), 7.75-7.61 (m, 2H), 7.44 (t, 1H, J=5.8), 7.38-7.22 7.07 (m, 3H), 5.03 (dd, 1H, J=5.3, 7.8), 4.99-4.82 (m, 2H), 4.18 (m, 2H), 4.08 (m, 2H), 3.82 (s, 2H), 3.75 (m, 2H), 3.51 (dd, 1H, J=12.2, 21.9), 3.21 (dd, 1H, J=4.4, 11.2), 2.54 (s, 6H), 2.06 (m, 2H), 1.92 (m, 2H), 1.39 (s, 21H), 1.28 (s, 9H). NMR-$^{13}$C (DMSO-d$_6$): δ=169.2 (C$_q$), 166.6 (C$_q$), 162.2 (C$_q$), 153.5 (C$_q$), 150.2 (C$_q$), 147.2 (CH), 143.1 (CH), 140.0 (CH), 131.7 (CH), 128.2 (CH), 127.6 (CH), 127.4 (CH), 127.3 (CH), 84.3 (C$_q$), 82.16 (C$_q$), 80.6 (C$_q$), 80.4 (C$_q$), 77.6 (CH$_2$), 73.5 (CH), 67.8 (CH$_2$), 66.0 (CH$_2$), 65.8 (CH), 57.8 (CH$_2$), 55.4 (CH), 35.7 (CH$_2$), 30.7 (CH$_2$), 27.7 (CH$_3$), 27.4 (CH$_3$), 27.3 (CH$_3$), 22.4 (CH$_3$), 20.5 (CH$_3$). LCMS: m/z: 910.6 [M$^+$].

EXAMPLE 4

Synthesis of 2S,4R,20S-3-[tert-butoxycarbonyl-(2-{5-[(tert-butoxycarbonyl-pyridin-2-yl-amino)-methyl]-pyrrolidin-3-yloxy}-acetyl)-amino]-2-(2,4,6-trimethyl-benzenesulfonylamino)-propionic acid tert-butyl ester (7)

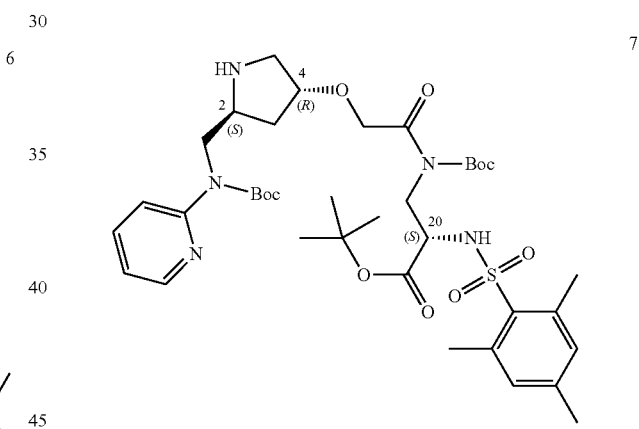

7

1.3 g (1.42 mmol) of 6 as prepared in example 3 were dissolved in 25 mL of isopropanol and 130 mg Pd (10% on carbon) were added. The reaction mixture was stirred under H$_2$-atmosphere for 12 h, filtered over cellite and the solvent was removed at the evaporator. The crude product was chromatographed on silica gel using ethyl acetate/MeOH.

Yield 820 mg (74%). NMR-$^1$H (DMSO-d$_6$): δ=8.27 (dd, 1H, J=0.9, 4.9), 7.72-7.62 (m, 2H), 7.47 (d, 1H, J=8.3), 7.07 (m, 3H), 5.02 (dd, 1H, J=4.9, 8.3), 4.03 (m, 1H), 3.92-3.62 (m, 7H), 3.43 (t, 1H, J=6.8), 2.80 (d, 2H, J=2.9), 2.53 (s, 6H), 1.84 (dd, 1H, J=7.3, 14.2), 1.40 (s, 21H), 1.28 (s, 9H). NMR-$^{13}$C (DMSO-d$_6$): δ=169.6 (C$_q$), 166.7 (C$_q$), 154.3 (C$_q$), 153.5 (C$_q$), 150.2 (C$_q$), 147.3 (CH), 143.1 (C$_q$), 140.0 (C$_q$), 137.2 (CH), 133.6 (C$_q$), 131.7 (CH), 120.4 (CH), 119.9 (CH), 84.3 (C$_q$), 82.2 (C$_q$), 80.8 (CH), 80.3 (C$_q$), 67.5 (CH$_2$), 59.7 (CH$_2$), 57.9 (CH), 55.9 (CH), 51.3 (CH$_2$), 50.4 (CH$_2$), 35.9 (CH$_2$), 27.8 (CH$_3$), 27.5 (CH$_3$), 27.3 (CH$_3$), 22.4 (CH$_3$), 20.5 (CH$_3$). LCMS: m/z: 778.6 [M$^+$].

EXAMPLE 5

Synthesis of 2S,4R,20S-4-[(2-amino-2-tert-butoxy-carbonyl-ethylcarbamoyl)-methoxy]-2-[(tert-butoxy-carbonyl-pyridin-2-yl-amino)-methyl]-pyrrolidine-1-carboxylic acid benzyl ester (8)

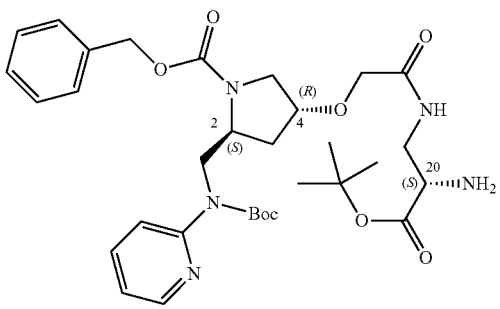

2.58 g (6.12 mmol) of 1 as prepared in example 1, 2.34 g (6.12 mmol) of 3S-3-Amino-2-(9H-fluoren-9-ylmethoxycarbonylamino)-propionic acid tert-butyl ester, 2.55 g (6.73 mmol) of HBTU and 4.2 mL (24.5 mmol) of DIPEA were dissolved in 40 mL of DMF and stirred for 2.5 h at room temperature. The solvent was removed under vacuum and the crude product was taken up in 600 mL of ethyl acetate. The organic layer was extracted with saturated $NaHCO_3$ and NaCl solution, dried with $Na_2SO_4$ and the solvent was removed at the evaporator. The crude reaction mixture was taken up in 70 mL of absolute THF. 5.34 g (24.5 mmol) of $(BocO)_2O$, 150 mg (1.22 mmol) of DMAP and 1.28 (12.24 mmol) of DIPEA were added. After 12 h at room temperature 2.67 g (12.2 mmol) of $(BocO)_2O$ and 150 mg (1.22 mmol) of DMAP were added and stirred for additional 12 h at room temperature. The solvent was removed at the evaporator and the crude product was pored into 500 mL of ethyl acetate. The organic layer was extracted with saturated $NaHCO_3$ and NaCl solution, dried with $Na_2SO_4$ and the solvent was removed at the evaporator. The crude product was chromatographed on silica gel using ethyl acetate/hexane.

The product was dissolved in 25 mL of absolute DCM and 1.6 g (18.4 mmol) of morpholine were added and stirred for 12 h at room temperature. The solvent was removed and the crude reaction mixture was taken up in MeOH. The precipitate was filtered off and the solvent was removed at the evaporator. The crude product was chromatographed on silica gel using ethyl acetate/hexane.

Yield 588 mg (15%). NMR-$^1$H (DMSO-$d_6$): δ=8.31 (dd, 1H, J=3.4, 12.7), 7.70 (tm, 1H, J=8.3), 7.55 (t, 1H, J=5.4), 7.46 (tm, 1H, J=6.3), 7.39-7.23 (m, 6H), 7.10 (ddd, 1H, J=1.0, 4.9, 7.3), 5.05-4.81 (m, 2H), 4.20 (m, 1H), 4.11 (m, 3H), 3.81 (d, 2H, J=2.0), 3.50 (ddm, 2H, J=12.2, 20.0), 3.33 (m, 2H), 3.22 (m, 3H), 2.17 (m, 1H), 1.97 (m, 2H), 1.41 (s, 9H), 1.36 (s, 9H). NMR-$^{13}$C (DMSO-$d_6$) (partial signal doubling due Cbz-rotameres): δ=173.1 ($C_q$), 168.8 ($C_q$), 154.0 ($C_q$), 153.9 ($C_q$), 153.5 ($C_q$), 147.3 (CH), 137.2 (CH), 137.0 (CH), 136.8 ($C_q$), 128.3 (CH), 127.7 (CH), 127.4 (CH), 120.0 (CH), 80.6 ($C_q$), 80.4 ($C_q$), 80.2 ($C_q$), 77.6 (CH), 77.1 (CH), 67.8 ($CH_2$), 66.0 ($CH_2$), 65.7 ($CH_2$), 55.4 ($CH_2$), 55.0 ($CH_2$), 54.1 (CH), 51.1 ($CH_2$), 50.8 ($CH_2$), 48.3 ($CH_2$), 42.2 ($CH_2$), 27.8 (CH), 27.6 ($CH_3$). LCMS: m/z: 628.3 [M$^+$].

EXAMPLE 6

Derivatization of 2S,4R,20S-3-[tert-butoxycarbonyl-(2-{5-[(tert-butoxycarbonyl-pyridin-2-yl-amino)-methyl]-pyrrolidin-3-yloxy}-acetyl)-amino]-2-(2,4,6-trimethyl-benzenesulfonylamino)-propionic acid tert-butyl ester (7)

Starting from synthesis of 2S,4R,20S-3-[tert-butoxycarbonyl-(2-{5-[(tert-butoxycarbonyl-pyridin-2-yl-amino)-methyl]-pyrrolidin-3-yloxy}-acetyl)-amino]-2-(2,4,6-trimethyl-benzenesulfonylamino)-propionic acid tert-butyl ester (7) as prepared in example 4 various derivatives thereof were synthesized according to the following protocols.

Figure 2:
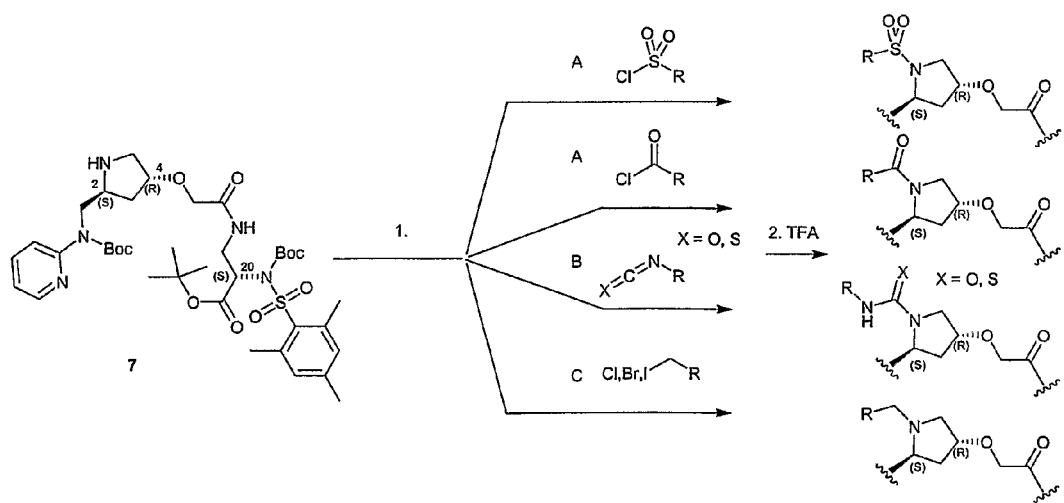
FIG. 2 shows a reaction scheme for the derivatization of 2S,4R,20S-3-[tert-butoxycarbonyl-(2-{5-[(tert-butoxycarbonyl-pyridin-2-yl-amino)-methyl]-pyrrolidin-3-yloxy}-acetyl)-amino]-2-(2,4,6-trimethyl-benzenesulfonylamino)-propionic acid tert-butyl ester (7). The rest R is specified in table 1.

The reaction scheme is shown in FIG. 2.

Protocol A:

15 mg (0.019 mmol) of 7 as prepared in example 4, and 7 mL (0.039 mmol) of DIPEA were dissolved in 300 mL of DCM and cooled to 0° C. 0.057 mmol of $ClSO_2$—R or ClCO—R, dissolved in 200 mL of DCM, were added and stirred for 2 h under slowly warn up to room temperature. The solvent was removed at the evaporator and to the crude product were added to 300 mL of TFA. After 4 h at room temperature the solvent was removed at the evaporator. The crude product was purified by HPLC and was freeze dried using ACN/$H_2O$.

Protocol B:

15 mg (0.019 mmol) of 7 as prepared in example 4, and 7 mL (0.039 mmol) of DIPEA were dissolved in 300 mL DCM. 0.057 mmol of OCN—R or SCN—R, dissolved in 200 mL of DCM, were added and stirred for 2 h at 40° C. The solvent was removed at the evaporator and to the crude product were added to 300 mL of TFA. After 4 h at room temperature the solvent was removed at the evaporator. The crude product was purified by HPLC and was freeze dried using ACN/$H_2O$.

Protocol C:

15 mg (0.019 mmol) of 7 as prepared in example 4, and 7 mL (0.039 mmol) of DIPEA were dissolved in 500 mL DCM. 0.057 mmol Cl—R, Br—R or I—R were added and stirred for 12 h at 40° C. The solvent was removed at the evaporator and to the crude product were added to 300 mL of TFA. After 4 h at room temperature the solvent was removed at the evaporator. The crude product was purified by HPLC and was freeze dried using ACN/$H_2O$.

EXAMPLE 7

Synthesis of 2S,4R,20S-3-{2-[1-phenylacetyl-5-(pyridin-2-ylaminomethyl)-pyrrolidin-3-yloxy]-acetylamino}-2-(2,4,6-trimethyl-benzenesulfonylamino)-propionic acid (9)

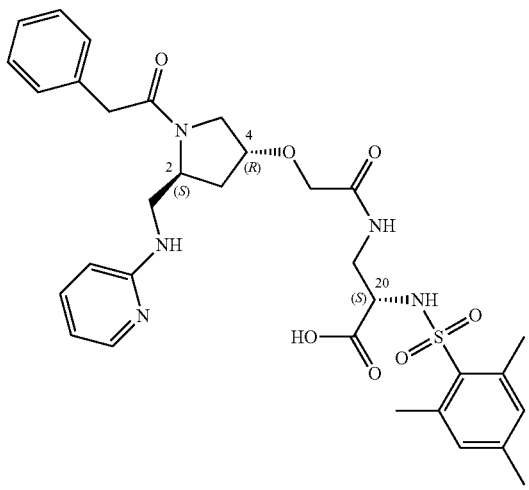

Protocol A (see example 6): 15 mg (0.019 mmol) of 7 and 7 mL (0.039 mmol) of DIPEA were dissolved in 300 mL DCM and cooled down to 0° C. 4.6 mg (0.057 mmol) of phenyl-acetyl chlorid, dissolved in 200 mL of DCM, were added and stirred for 2 h under slowly warm up to room temperature. The solvent was removed at the evaporator and 300 mL of TFA were added to the crude product. After 4 h at room temperature the solvent was removed at the evaporator. The crude product was purified by HPLC and was freeze dried using ACN/H$_2$O.

Yield 8.9 mg (61%, TFA-salt). NMR-$^1$H (DMSO-d$_6$): δ=8.67 (s, broad, 1H), 8.03-7.86 (m, 3H), 7.73 (t, 1H, J=5.4), 7.34-7.09 (m, 6H), 6.97 (s, 2H), 6.86 (t, 1H, J=6.8), 4.28-3.36 (m, 9H), 3.18 (m, 2H), 2.52 (s, 6H), 2.23 (s, 3H), 2.17 (m, 1H), 1.97 (m, 1H), 1.26 (m, 1H). LCMS: m/z: 638.5 [M$^+$].

It is to be acknowledged that according to the protocol described herein any of compounds 13 to 65 as specified in Table 1 herein, can be synthesized.

EXAMPLE 8

Derivatization of 2S,4R,20S-4-[(2-amino-2-tert-butoxycarbonyl-ethylcarbamoyl)-methoxy]-2-[(tert-butoxycarbonyl-pyridin-2-yl-amino)-methyl]-pyrrolidine-1-carboxylic acid benzyl ester (8)

Starting from 2S,4R,20S-4-[(2-amino-2-tert-butoxycarbonyl-ethylcarbamoyl)-methoxy]-2-[(tert-butoxycarbonyl-pyridin-2-yl-amino)-methyl]-pyrrolidine-1-carboxylic acid benzyl ester (8), as prepared in example 5 various derivatives thereof were synthesized according to the following protocols.

Figure 3:
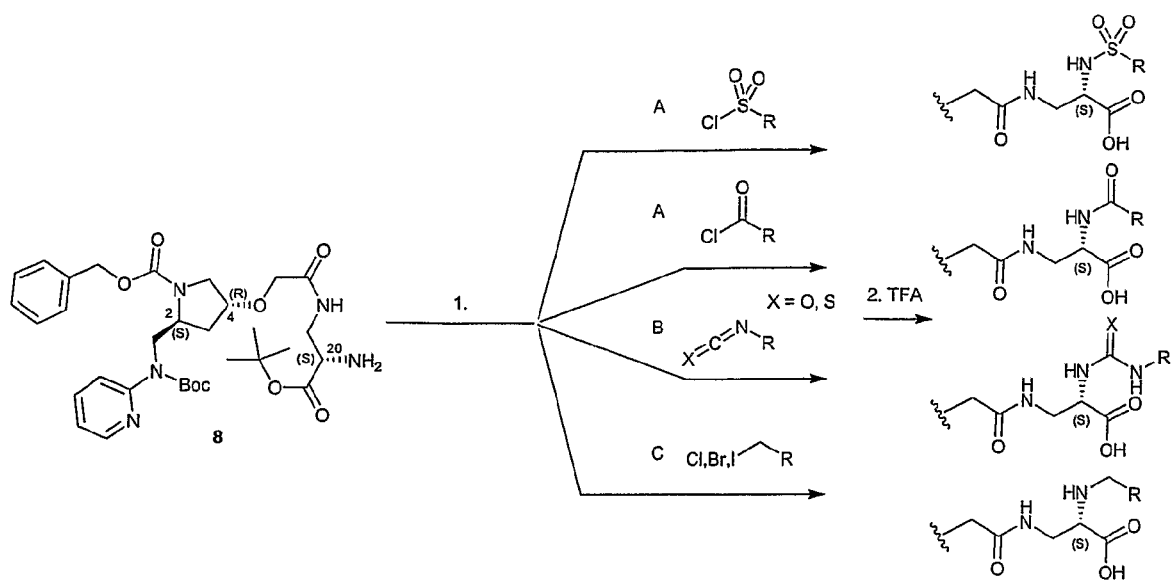
FIG. 3 shows a reaction scheme for the derivatization of 2S,4R,20S-4-[(2-amino-2-tert-butoxycarbonyl-ethylcarbamoyl)-methoxy]-2-[(tert-butoxycarbonyl-pyridin-2-yl-amino)-methyl]-pyrrolidine-1-carboxylic acid benzyl ester (8). The rest R is specified in table 1.

The reaction scheme is shown in FIG. 3.

Protocol A:

15 mg (0.0318 mmol) of 8 and 16 mL (0.0954 mmol) of DIPEA were dissolved in 300 mL of DCM and cooled down to 0° C. 0.0954 mmol of ClSO$_2$—R or ClCO—R, dissolved in 200 mL of DCM, were added and stirred for 2 h under slowly warm up to room temperature. The solvent was removed at the evaporator and 300 mL of TFA were added to the crude product. After 4 h at room temperature the solvent was removed at the evaporator. The crude product was purified by HPLC and was freeze dried using ACN/H$_2$O.

Protocol B 15 mg (0.0318 mmol) of 8 and 16 mL (0.0954 mmol) of DIPEA were dissolved in 300 mL DCM. 0.0954 mmol OCN—R or SCN—R, dissolved in 200 mL of DCM, were added and stirred for 2 h at 40° C. The solvent was removed at the evaporator and 300 mL of TFA were added to the crude product. After 4 h at room temperature the solvent was removed at the evaporator. The crude product was purified by HPLC and was freeze dried using ACN/H$_2$O.

Protocol C 15 mg (0.0318 mmol) of 8 and 16 mL (0.0954 mmol) of DIPEA were dissolved in 500 mL DCM. 0.0954 mmol Cl—R, Br—R or I—R were added and stirred for 12 h at 40° C. The solvent was removed at the evaporator and 300 mL of TFA were added to the crude product. The crude product was purified by HPLC and was freeze dried using ACN/H$_2$O.

EXAMPLE 9

Synthesis of 2S,4R,20S-4-[(2-benzenesulfonylamino-2-carboxy-ethylcarbamoyl)-methoxy]-2-(pyridin-2-ylaminomethyl)-pyrrolidine-1-carboxylic acid benzyl ester (10)

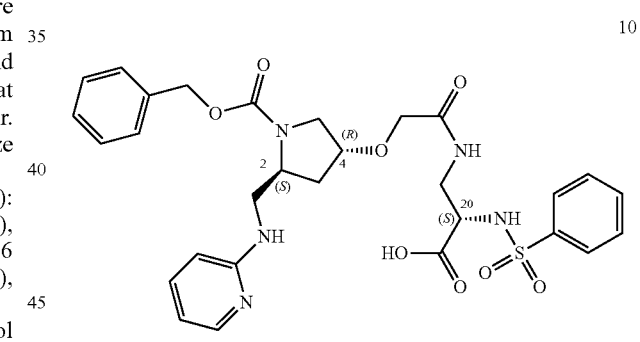

Protocol A (see example 8): 15 mg (0.0318 mmol) of 8 and 16 mL (0.0954 mmol) of DIPEA were dissolved in 300 mL DCM and cooled down to 0° C. 16.8 mg (0.0954 mmol) of benzenesulfonyl chloride, dissolved in 200 mL of DCM, were added and stirred for 2 h under slowly warm up to room temperature. The solvent was removed at the evaporator and to the crude product were added to 300 mL of TFA. After 4 h at room temperature the solvent was removed at the evaporator. The crude product was purified by HPLC and was freeze dried using ACN/H2O.

Yield 10.7 mg (46%, TFA-salt). NMR-$^1$H (DMSO-d$_6$): δ=8.25 (s, broad, 1H), 8.18 (d, 1H, J=8.3), 7.98-7.67 (m, 5H), 7.67-7.48 (m, 4H), 7.35 (m, 6H), 7.02 (dm, 1H, J=8.3), 6.81 (tm, 1H, J=5.9), 5.08 (s, 1H), 4.10 (m, 3H), 3.95-3.34 (m, 6H), 3.14 (m, 1H), 2.17 (m, 1H), 1.91 (m, 1H). LCMS: m/z: 612.5 [M$^+$].

It is to be acknowledged that according to the protocol described herein any of the compounds 66 to 128 as specified in Table 1 herein, can be synthesized.

EXAMPLE 10

Synthesis of Derivatives of 11

Figure 4:
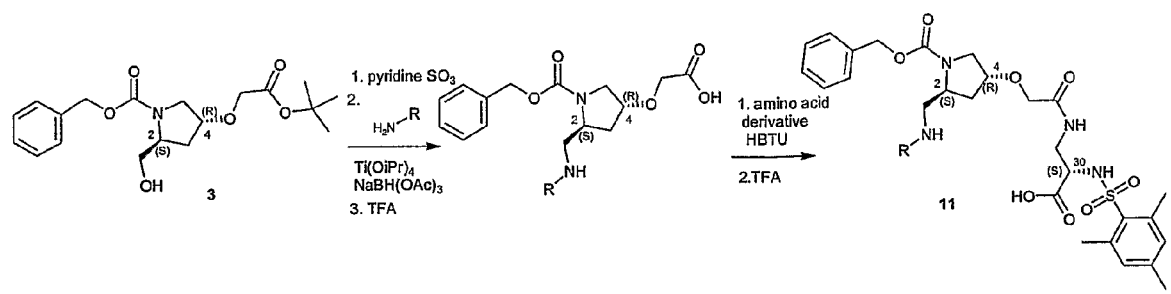
FIG. 4 shows a reaction scheme for the synthesis of derivatives of 2S,4R-4-carboxymethoxy-2-(pyridin-2-ylaminomethyl)-pyrrolidine-1-carboxylic acid benzyl ester (1) starting from 2S,4R-4-tert-butoxycarbonylmethoxy-2-hydroxymethyl-pyrrolidine-1-carboxylic acid benzyl ester (3) to give derivatives of 11. The rest R is specified in table 1.

FIG. 4 shows a reaction scheme for the synthesis of derivatives of 2S,4R-4-carboxymethoxy-2-(pyridin-2-ylaminomethyl)-pyrrolidine-1-carboxylic acid benzyl ester (1) starting from 2S,4R-4-tert-butoxycarbonylmethoxy-2-hydroxymethyl-pyrrolidine-1-carboxylic acid benzyl ester (2) to give derivatives of 11. The syntheses of the derivatives of 11 were performed using a modified protocol (without utilizing Boc-protection groups) from the synthesis of 4, 1 and 5 and purified by HPLC.

It is to be acknowledged that according to the protocol described herein any of the compounds 129-148 as specified in Table 1 herein, can be synthesized.

EXAMPLE 11

Solid Phase Synthesis of Derivatives of 12

Figure 5:
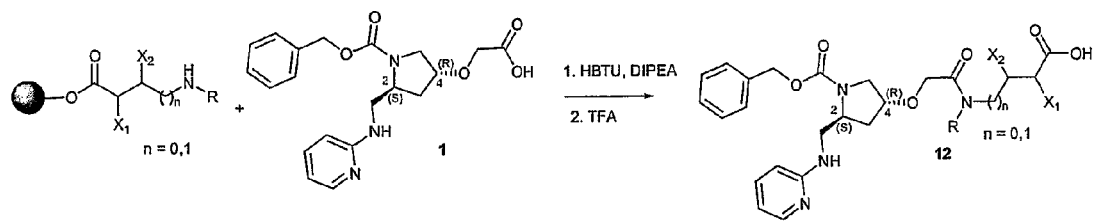
FIG. 5 shows a reaction scheme for the solid phase synthesis employing [2S,4R-4-carboxymethoxy-2-(pyridin-2-ylaminomethyl)-pyrrolidine-1-carboxylic acid benzyl ester (1) to give derivatives of 12. The rest $X_1$, $X_2$ and R is specified in table 1.

FIG. 5 shows a reaction scheme for the solid phase synthesis employing [2S,4R-4-carboxymethoxy-2-(pyridin-2-ylaminomethyl)-pyrrolidine-1-carboxylic acid benzyl ester (1) to give derivatives of 12. The derivatives of 12 were synthesized by standard solid phase peptide synthesis using triethyl-resin and purified by HPLC.

It is to be acknowledged that according to the protocol described herein any of the compounds 149-157 as specified in Table 1 herein, can be synthesized.

It is also possible to use derivatives of the staring materials 1, 3, 8 and 7 in example 6, 8, 10 and 11 to give other derivatives of the described compounds in table 1, using the described protocols. These minor changes in the staring materials 1, 3, 8 and 7 can be preformed by any person skilled in the art, more particularly by any organic chemist.

EXAMPLE 12

Biological Characterization of the Compounds

1. Integrin Receptor Binding Assays

The IC50 values of selected inhibitors were determined using competitive ELISA studies by inhibition of binding of integrin to the most active ligand of the integrin. The optimal concentrations of integrin and ligand were selected from ELISA binding studies with variable concentrations of both to obtain optimal signal noise ratio for further studies. IC50 studies were performed with fixed concentration of ligand and integrin and a serial dilution of inhibitor. The plates were measured with SpectraMax Plus reader (Molecular Devices). The resulting inhibition curves were analyzed using Soft-MaxPro 4.0 software, the turning point describes the IC50 value.

Fibronectin and Vitronectin were purchased from Sigma, fibrinogen from Calbiochem. (EMD Biosciences, Darmstadt, Germany) The integrin alpha5beta1 extracellular domain Fc-fusion was expressed and purified as described in (Coe, 2001, JBC, 276, 35854). Integrins alphavbeta3 and alphavbeta5 were purchased from Chemicon (Chemicon Europe, Germany) and alphaIIbbeta3 form Kordia (Kordia Life Science, Leiden, Netherlands)

1.1. Alpha5beta1—Fibronectin Binding Assay

Fibronectin was diluted with coating buffer (15 mM $Na_2CO_3$, 35 mM $NaHCO_3$, pH9.6) and coated with 100 µL/well to Nunc-Immuno maxisorp plates (Nalge Nunc Europe Ltd) over night at 4° C. After discarding the coating solution plates were washed 3 times with buffer 1 (25 nM Tris, pH7.6, 150 mM NaCl, 1 mM $MnCu_2$, 1 mg/mL BSA) and blocked with 100 µL blocking buffer (3% BSA in PBS 0.1% Tween20) for 1 hour at room temperature. After washing the blocked plates (3 times) with buffer 1, integrin (50 µL) and either inhibitor (serial dilution in buffer 1) or buffer 1 (50 µL) were added to the wells and incubated for one hour at RT. Plates were then washed (3 times) with buffer 1 and incubated with 100 µL of anti-human-Fc-HRP antibody conjugate (Sigma-Aldrich, Taufkirchen, Germany) in buffer 1 for 1 hour at RT. After additional washing steps (3 times) with buffer 1 50 µL of HRP substrate solution TMB (Seramun, Germany) were added to the wells. Colour development was stopped after 3-5 minutes with 50 µL 1M $H_2SO_4$. The developed colour was measured at 450 nm and analyzed as described above.

1.2. Vitronectin Binding Assay 1.2.1. Alphavbeta3

Vitronectin was diluted with coating buffer (15 mM $Na_2CO_3$, 35 mM $NaHCO_3$, pH9.6) and coated with 100 µL/well to Nunc-Immuno maxisorp plates over night at 4° C. After discarding the coating solution plates were washed 3 times with buffer 1 (25 mM Tris, pH7.6, 150 mM NaCl, 1 mM $MnCl_2$, 1 mg/mL BSA) and blocked with 100 µL blocking buffer (3% BSA in PBS 0.1% Tween20) for 1 hour at room temperature. After washing the blocked plates (3 times) with buffer 1, integrin alphavbeta3 (50 µL) and either inhibitor (serial dilution in buffer 1) or buffer 1 (50 µL) were added to the wells and incubated for one hour at RT. Plates were then washed (3 times) with buffer 1 and incubated with 100 µL of anti-avbeta3 antibody (Pharmingen, BD Bioscience Europe) in buffer 1 for 1 hour at RT. Plates were washed (3 times) with buffer 1 and incubated for 1 hour with 100 µL secondary antibody (anti-mouse-HRP conjugate, Sigma) in buffer 1. After additional washing step (3 times) with buffer 1 50 µL of HRP substrate solution TMB (Seramun) were added to the wells. Colour development was stopped after 3-5 minutes with 50 µL 1M $H_2SO_4$. The developed colour was measured at 450 nm and analyzed as described above.

1.2.2. Alphavbeta5

Vitronectin was diluted with coating buffer (15 mM $Na_2CO_3$, 35 mM $NaHCO_3$, pH9.6) and coated with 50 µL/well to Nunc-Immuno maxisorp plates over night at 4° C. After discarding the coating solution plates were washed 3 times with buffer 1 (25 mM Tris, pH7.6, 150 mM NaCl, 1 mM $MnCl_2$, 1 mg/mL BSA) and blocked with 100 µL blocking buffer (3% BSA in PBS 0.1% Tween20) for 1 hour at room temperature. After washing the blocked plates (3 times) with buffer 1, integrin alphavbeta5 (25 µL) and either inhibitor (serial dilution in buffer 2: 25 mM Tris, pH7.6, 150 mM NaCl, 1 mM $MnCl_2$, 1 mM $MgCl_2$, 1 mM $CaCl_2$, 1 mg/mL BSA, 0.05% Tween20) or buffer 2 (25 µL) were added to the wells and incubated for one hour at RT.

Plates were then washed (3 times) with buffer 2 and incubated with 50 µL of anti-alphavbeta5 antibody (Chemicon) in buffer 2 for 1 hour at RT. Plates were washed (3 times) with buffer 2 and incubated for 1 hour with 50 µL secondary antibody (anti-mouse-HRP conjugate, Sigma) in buffer 2. After additional washing step (3 times) with buffer 2 50 µL of HRP substrate solution TMB (Seramun) were added to the wells. Colour development was stopped after 3-5 minutes with 50 µL 1M $H_2SO_4$. The developed colour was measured at 450 nm and analyzed as described above.

1.3. AlphaIIbbeta3—Fibrinogen Binding Assay

Fibrinogen was diluted with coating buffer (15 mM $Na_2CO_3$, 35 mM $NaHCO_3$, pH9.6) and coated with 100 µL/well to Nunc-Immuno maxisorp plates over night at 4° C.

After discarding the coating solution plates were washed 3 times with buffer 1 (25 mM Tris, pH7.6, 150 mM NaCl, 1 mM MnCl$_2$, 1 mg/mL BSA) and blocked with 100 μL blocking buffer (3% BSA in PBS 0.1% Tween20) for 1 hour at room temperature. After washing the blocked plates (3 times) with buffer 1, integrin alphaIIbbeta3 (50 μL) and either inhibitor (serial dilution in buffer 3, 25 mM Tris, pH7.6, 150 mM NaCl, 1 mM MnCl$_2$, 1 mg/mL BSA 1 mM MgCl$_2$, 1 mM CaCl$_2$,) or buffer 3 (50 μL) were added to the wells and incubated for one hour at RT. Plates were then washed (3 times) with buffer 3 and incubated with 100 μL of anti-alphaIIbbeta3 antibody (anti CD41b, Pharmingen) in buffer 3 for 1 hour at RT. Plates were washed (3 times) with buffer 3 and incubated for 1 hour with 100 μL secondary antibody (anti-mouse-HRP conjugate, Sigma) in buffer 3. After additional washing steps (3 times) with buffer 3 50 μL of HRP substrate solution TMB (Seramun) were added to the wells. Colour development was stopped after 3-5 minutes with 50 μL 1M H$_2$SO$_4$. The developed colour was measured at 450 nm and analyzed as described above.

The results of the various assays performed on some of the compounds according to the present invention are depicted as IC50 values in table 2.

TABLE 2

IC50 values of selected compounds with different integrins

| Compound Nr. | IC$_{50}$ alpha5beta1 in nM | IC$_{50}$ alphavbeta3 in nM | IC$_{50}$ alphavbeta5 in nM | IC$_{50}$ alphaIIbbeta3 in nM |
|---|---|---|---|---|
| 5 | 3.7 | 11.6 | 230 | 9000 |
| 71 | 2.4 | ~30,000 | >50,000 | >50,000 |
| 44 | 5.8 | — | — | — |
| 38 | 11.9 | — | — | — |
| 20 | 6.6 | — | — | — |
| 15 | 11.3 | — | — | — |
| 25 | 18.1 | — | — | — |

TABLE 3

Binding activities of selected compounds to integrin alpha5beta1 determined in accordance with the method described in section 1.1 above. Based on the binding activities the various compounds disclosed herein can be grouped as follows:
Group A: less than 10 nM
Group B: between 10 nM and 500 nM
Group C: more than 500 nM

| Compound Nr. | Group |
|---|---|
| 5 | A |
| 15 | B |
| 18 | B |
| 20 | A |
| 25 | B |
| 31 | A |
| 35 | B |
| 36 | B |
| 38 | B |
| 41 | A |
| 44 | A |
| 61 | B |
| 63 | C |
| 69 | C |
| 71 | A |
| 74 | B |
| 80 | B |
| 81 | C |
| 82 | C |
| 86 | C |
| 90 | A |
| 91 | A |
| 92 | A |
| 96 | A |
| 97 | A |
| 104 | B |
| 106 | B |
| 117 | A |
| 118 | A |
| 126 | C |
| 127 | B |
| 130 | C |
| 135 | C |
| 148 | A |
| 150 | C |
| 152 | C |

2. Cellular Inhibition Assays 2.1. Cell Adhesion Assay with K562

K562 erythroleukemia cells were obtained from the German Collection of Microorganisms and Cell Cultures GmbH (DMSZ, Braunschweig, Germany). Cells were cultured in RPMI medium containing 10% fetal calf serum, 2 mM glutamine and 100 U/mL penicillin-streptomycin (all from Biochrom AG, Germany).

The cell adhesion assays were performed in 96-well Nunc-Immuno maxisorp plates. The wells were coated for 1 h at 37° C. with 100 μL aliquots of fibronectin (10 μg/mL in phosphate-buffered-saline, 120-kDa fragment, Chemicon Europe, Germany), then blocked with 10 mg/mL heat denatured BSA in phosphate buffer for 30 min.

K562 cells were resuspended to 4×10$^6$ cells/mL in 150 mL NaCl, 25 mM Hepes, 2 mM EDTA, pH 7.4, and incubated for 30 min at 37° C. As a next step the cells were washed two times with the same buffer. 100 μL cell aliquots were then added to 100 μL aliquots of the same buffer with in addition 4 mM MgCl$_2$, 100 mM PMA and different concentrations of compounds. These samples were preincubated for 30 min at 37° C. After that 100 μL aliquots were transferred to the microtiter wells and the cells were allowed to adhere to the substrate for 30 min at 37° C. in a humidified atmosphere of 5% CO$_2$. To determine the reference value for 100% attachment, cells were seeded on poly-L-Lysin (0.01% solution) coated wells and for detection of minimum attachment, cells were seeded on uncoated wells.

Adherent cells were then fixed by addition of 5% glutaraldehyde (100 μL/well) for 30 min at room temperature. After three wash steps with phosphate buffer the cells were stained with Crystal Violet (0.1% in 200 mM MES buffer, pH 6.0) for 1 h at room temperature. Excess dye was removed by three washes with phosphate buffer, and bound dye was solubilized with 100 μL of 10% acetic acid.

The absorbance of each well at 570 nm was then measured using the SpectraMax Plus reader. Each sample was assayed in quadruplicate, and minimum attachment was subtracted from all measurements.

Figure 6:
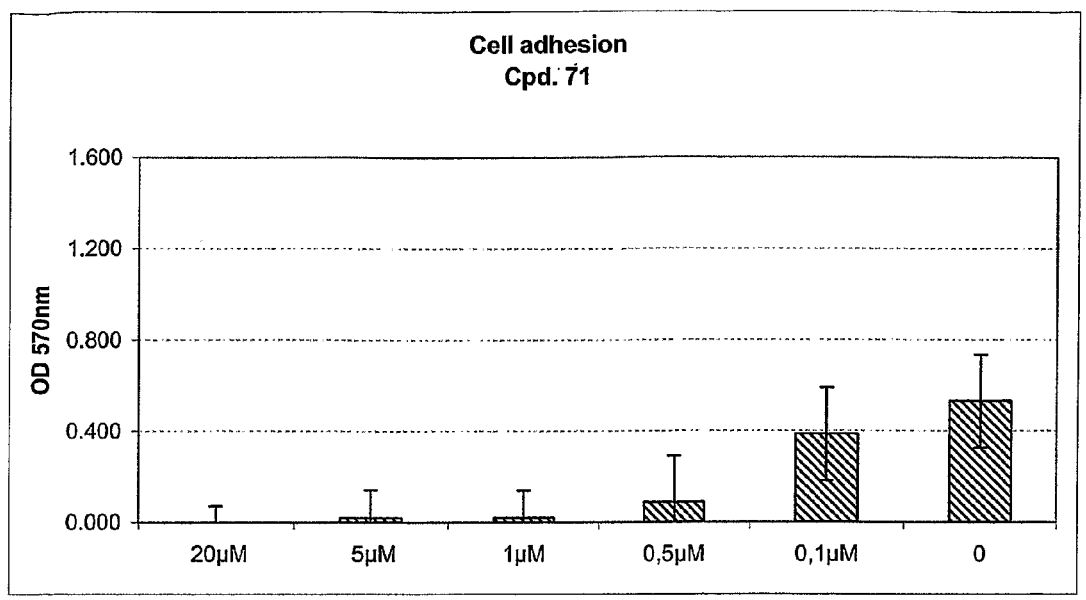
FIG. 6 shows a graph indicating the inhibition of K562 cell adhesion to fibronectin coated microtiter plates expressed as OD 570, using different concentrations of compound 71 being a compound according to the present invention.

The result is depicted in FIG. 6. As may be taken from FIG. 6 compound 71 and the other compounds from activity group A are significantly active in inhibiting cell adhesion in the above described assay at 0.5 μM.

3. In Vivo Studies
3.1. Physiological Retinal Angiogenesis at Newborn Rats

Rats are born with a completely avascular retina with physiological retinal vascular development occurring in a centripetal manner within the first two weeks of life. At postnatal day P6 approximately 65% is physiologically vascularized, with vascularization being complete by P10-14.

Sprague Dawley rats were used according to protocols which are in conformity with the Association for Research in Vision and Ophthalmology's statements on the Use of Animals in Ophthalmic Research.

Rat pups were taken from within 24 h of birth and injected intravitreally at P1 with 3 µL of selected compound solved in saline. The same injection was repeated at P3. Controls include vehicle injected, as well as uninjected eyes. The animals were sacrificed by decapitation at P6. Upon sacrifice the eyes were enucleated and fixed in 10% buffered formalin phosphate (Fisher Scientific) for 30 minutes at RT. The retinas were dissected and post-fixed in methanol for 10 minutes at −20° C. The retinas were washed with 1% Triton X-100 in PBS and incubated overnight with a 1/100 solution of TRITC conjugated lectin griffonia simplicifolia (Sigma-Aldrich) in 1% Triton X-100 in PBS. After washing with PBS, the retinas were flatmounted, viewed and photographed with an epifluorescent microscope (Nikon) and a digital camera set-up (Act1). The percentage of total vascularized area was calculated as a percent of the vascularized area over the total surface area (Adobe-Photoshop).

Figure 7:
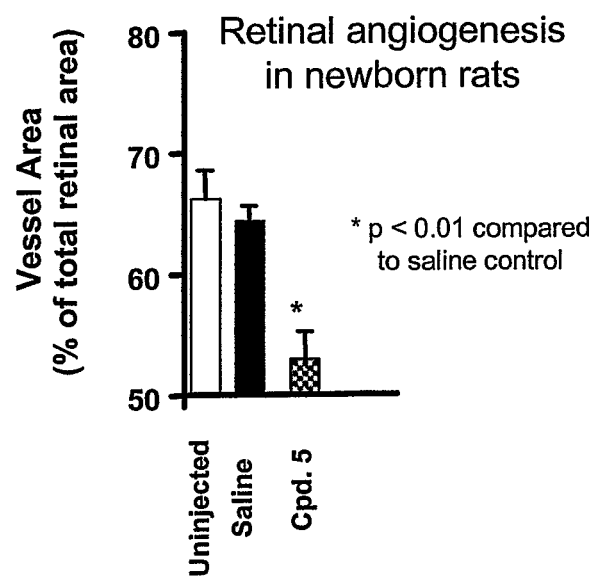
FIG. 7 shows a graph illustrating the effect of compound 5 being a compound according to the present invention on retinal angiogenesis in newborn rats expressed as vessel area, more particularly % of total retinal area.

The results are represented in FIG. 7. Under the influence of compound 5 retinal angiogenesis was significantly reduced compared to the vehicle treated and non-treated eye.

3.2. Corneal Angiogenesis in Mice

Induction of neovascularization in the cornea: 1 month old mice (C57) were anesthetized with a mixture of Rompun und Ketanest. For local anesthesia of eyes Novesine (0.4%, Novartis) was used. Neovascularization was induced by application of 2 µL of 0.15 M NaOH to the cornea of each mouse and the corneal and limbal epithet were scraped with a Tooke Corneal Knife (Arista Surgical Supply, New York). To prevent infection the eyes were treated with antibiotic ointment. Treatment: 7-10 days after induction of neovascularization mini-osmotic pumps (Alzet model 2001, Alza Corporation, Mountain View Calif.) were implanted intraperitoneally. Mice were implanted with pumps containing the test compound or vehicle, respectively. The pump rate was 1.0 µL/h. Treatment was carried out for 7 days.

Visualization of vessels: At the end of the experiment mice were euthanized using $CO_2$. The Corneas were flatmounted and stained with FITC anti-CD31 antibody for endothelial cells. Therefore corneas were fixed for 20 min in ice-cold acetone (100%). After washing 2-3 times with PBS corneas were incubated over night at 4° C. with fluorescence coupled antibodies (FITC-anti-CD31 (558738, BD Pharmingen) in PBS with 2% BSA). After incubation corneas were washed for 5-10 min in PBS and embedded with mounting medium (Sigma). The corneal neovascularization was quantified using fluorescence microscope and digitalization software (Zeiss improvisation open lab, NIH Image).

Activity group A compounds are able to inhibit significantly the corneal neovascularization in mice.

3.3. Oxygen Induced Retinal Angiogenesis in Rat

Animals: Sprague Dawley rats were used according to a protocol in conformity with the Association for Research in Vision and Ophthalmology's statement on the Use of Animals in Ophthalmic Research.

Rat pups were exposed to 8 cycles of hyperoxia (80% $O_2$, 21 h), hypercapnia (10% $CO_2$) and hypoxia (8% $O_2$, 1 h) with a gradual return to 80% $O_2$, from P1 to P8 (Modification of the model of Holmes et al.: Holmes, 1996. Curr Eye Res 15, 403, Holmes, 1997. Curr Eye Res 16, 725). The rats were returned to room-air and neovascularization was evaluated at P13, after 5 days of relative ischemia.

Drug administration: Rat pups were injected during the ischemic phase that follows the oxygen exposure. Rat pups were injected with 5 µL of test compound (in the right eye and vehicle in the left eye at P9 and P11 and sacrificed at P13.

Quantification of intravitreal neovascularization: Upon sacrifice the eyes were enucleated and fixed in 10% buffered formalin phosphate (Fisher Scientific) for 30 min at room temperature.

The retinas were dissected and post-fixed in methanol for 10 min at −20° C. The retinas were washed with 1% Triton X-100 in PBS and incubated overnight with a 1/100 solution of TRITC conjugated lectin griffonia simplicifolia (Sigma-Aldrich) in 1% Triton X-100 in PBS. After washing with PBS, the retinas were flatmounted, viewed and photographed with an epifluorescent microscope (Nikon) and digital camera set-up (Act-1). Clock hours of abnormal neovascularization were counted.

Statistical Analysis: Statistically significant differences among treated and untreated eye of the same animals were determined by paired t-test.

Activity group A compounds are able to inhibit significantly the oxygen induced neovascularization in rat.

The features of the present invention disclosed in the specification, the claims and/or the drawing may both separately and in any combination thereof be material for realizing the invention in various forms thereof.

The invention claimed is:

1. A compound of the formula (I)

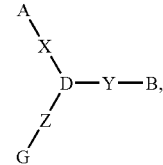

wherein

D is pyrrolidine,

X is a radical selected from the group consisting of C=O and (C=O)—O, wherein X is attached to the nitrogen atom of D, Y is a radical selected from the group consisting of —OCH$_n$—NH—(CH$_2$)$_n$ and —(CH$_2$)$_n$-E-(CH$_2$)$_m$-L-(CH$_2$)$_k$ wherein E is an O radical, k, m and n are individually and independently 0, 1, 2 and 3, Z is an alkyl radical, wherein the alkyl is CH$_2$ or CH$_2$CH$_2$, A is a radical selected from the group consisting of benzyl, phenyl, and alkyl, B is a radical having formula (II)

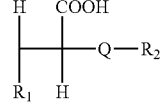

wherein

R$_1$ is H,

R$_2$ is selected from the group consisting of 1-methyl cyclohexyl, alkyl and, cycloalkyl, cycloalkylalkyl, G is pyridine-2-yl, and wherein Q and L are each and independently from each other a radical selected from the group consisting of (C=O)—NH, C=O, C=S, NH, O, S, CH$_2$, NH—NH, N=N, CH=N, N=CH, NH—(C=O)—NH, NH—(C=O), O—(C=O)—NH, NH—(C=O)—O, (C=O)—O, O—(C=O), NH—(C=S), (C=S)—NH, NH—(C=S)—NH, SO₂, NH—SO₂, SO₂—NH.

2. The compound according to claim 1, wherein Z is CH₂.
3. The compound according to claim 1, wherein A is a phenyl group or a benzyl group having the formula (IV) or (V)

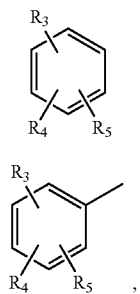

wherein $R_3$, $R_4$, and $R_5$ is each and independently a radical selected from the group consisting of H, halogen, alkyl, and alkoxy.

4. The compound according to claim 3, wherein alkyl is selected from the group consisting of methyl, ethyl, propyl, butyl, pentyl, hexyl, whereby any of the residues is straight, branched, branched-linear or branched non-linear.
5. The compound according to claim 3, wherein alkoxy is selected from the group consisting of methoxy, ethoxy, propoxy, butoxy, pentoxy, hexoxy.
6. The compound according to claim 3, wherein the halogen is independently selected from the group consisting of I, Br, Cl and F.
7. The compound according to claim 1, wherein $R_2$ is

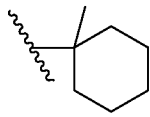

8. The compound according to claim 1, wherein Q of B is C=O.
9. The compound according to claim 1, wherein G is 3,4,5,6-tetrahydro-pyridin-2-ylamine.
10. The compound according to claim 1, wherein G is 4 methoxy-pyridin-2-ylamine.
11. A compound having the formula (VIII)

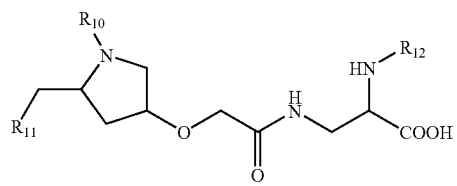

wherein $R_{10}$ is CO—O—$R_{13}$ or —CO—$R_{13}$,
wherein $R_{11}$ is pyridine-2-ylamine,
wherein $R_{12}$ is —CO—$R_{13}$, —SO₂—$R_{13}$, and
wherein $R_{13}$ is a radical selected from the group consisting of alkyl, cycloalkyl, and aryl.

12. The compound according to claim 11, whereby the compound has the formula (IX)

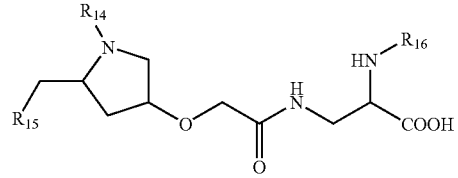

wherein $R_{14}$ is 3-carboxy-phenyl or 3,3-dimethyl-butyryl,
wherein $R_{15}$ is pyridin-2-ylamine or 4-methoxy-pyridin-2-ylamine,
wherein $R_{16}$ is —CO—$R_{17}$, and
wherein $R_{17}$ 1 methyl cyclohexyl.

13. A compound selected from the group consisting of
compound 91: 4-{[2-Carboxy-2-(cyclohexanecarbonyl-amino)-ethylcarbamoyl]-methoxy}-2-(pyridin-2-ylaminomethyl)-pyrrolidine-1-carboxylic acid benzyl ester
compound 101: 4-({2-Carboxy-2-[(1-methyl-cyclohexanecarbonyl)-amino]-ethylcarbamoyl}-methoxy)-2-(pyridin-2-ylaminomethyl)-pyrrolidine-1-carboxylic acid benzyl ester
compound 105: 4-({2-Carboxy-2-[(2-methyl-cyclohexanecarbonyl)-amino]-ethylcarbamoyl}-methoxy)-2-(pyridin-2-ylaminomethyl)-pyrrolidine-1-carboxylic acid benzyl ester
compound 119: 4-{[2-Carboxy-2-(cyclopropanecarbonyl-amino)-ethylcarbamoyl]-methoxy}-2-(pyridin-2-ylaminomethyl)-pyrrolidine-1-carboxylic acid benzyl ester
compound 120: 4-{[2-Carboxy-2-(2-cyclopentyl-acetylamino)-ethylcarbamoyl]-methoxy}-2-(pyridin-2-ylaminomethyl)-pyrrolidine-1-carboxylic acid benzyl ester
compound 121: 4-[(2-Carboxy-2-isobutyrylamino-ethylcarbamoyl)-methoxy]-2-(pyridin-2-ylaminomethyl)-pyrrolidine-1-carboxylic acid benzyl ester
compound 122: 4-{[2-Carboxy-2-(2-cyclohexyl-acetylamino)-ethylcarbamoyl]-methoxy}-2-(pyridin-2-ylaminomethyl)-pyrrolidine-1-carboxylic acid benzyl ester
compound 123: 4-{[2-Carboxy-2-(2-propyl-pentanoylamino)-ethylcarbamoyl]-methoxy}-2-(pyridin-2-ylaminomethyl)-pyrrolidine-1-carboxylic acid benzyl ester
compound 124: 4-{[2-Carboxy-2-(4-methyl-pentanoylamino)-ethylcarbamoyl]-methoxy}-2-(pyridin-2-ylaminomethyl)-pyrrolidine-1-carboxylic acid benzyl ester
compound 125: 4-{[2-Carboxy-2-(2-cycloheptyl-acetylamino)-ethylcarbamoyl]-methoxy}-2-(pyridin-2-ylaminomethyl)-pyrrolidine-1-carboxylic acid benzyl ester
compound 147: 4-({2-Carboxy-2-[(1-methyl-cyclohexanecarbonyl)-amino]-ethylcarbamoyl}-methoxy)-2-[(4-methoxy-pyridin-2-ylamino)-methyl]-pyrrolidine-1-carboxylic acid benzyl ester
compound 148: 3-(2-{1-(3,3-Dimethyl-butyryl)-5-[(4-methoxy-pyridin-2-ylamino)-methyl]-pyrrolidin-3-yloxy}-acetylamino)-2-[(1-methyl-cyclohexanecarbonyl)-amino]-propionic acid.

14. A pharmaceutical composition comprising a compound according to claim 1 and a pharmaceutically acceptable carrier, diluent or excipient.
15. The pharmaceutical composition according to claim 14, wherein the compound is present as a pharmaceutically acceptable salt.

16. The compound according to claim 1, wherein n is 0, E is 0, m is 1, L is (C=O)—NH and k is 0.

17. A compound of the formula (I)

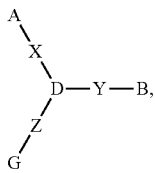

wherein

D is pyrrolidine,

X is a C=O radical, wherein X is attached to the nitrogen atom of D,

Y is a —(CH$_2$)$_n$-E-(CH$_2$)$_m$-L-(CH$_2$)$_k$ radical, wherein E is an O radical, n is 0, m is 1, k is 0, Z is an alkyl radical, wherein the alkyl is CH$_2$, A is an alkyl radical, B is a radical having formula (II)

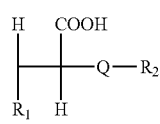

wherein

R$_1$ is H,

R$_2$ is

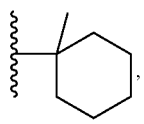

G is 4-methoxy-pyridin-2-ylamine, and wherein Q and L are each and independently from each other a radical selected from the group consisting of (C=O)—NH, NH and NH—(C=O), or a pharmaceutically acceptable salt thereof.

18. A compound of the formula:

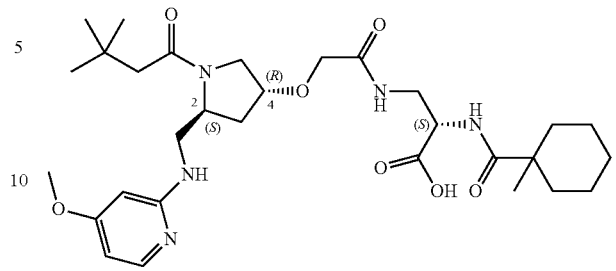

or a pharmacologically acceptable salt thereof.

19. The compound according to claim 18, wherein the compound is 3-(2-{1-(3,3-Dimethyl-butyryl)-2-[(4-methoxy-pyridin-2-ylamino)-methyl]-pyrrolidin-3-yloxy}-acetylamino)-2-[(1-methyl-cyclohexanecarbonyl)-amino]-propionic acid.

20. A pharmaceutical composition comprising a compound according to claim 18 or claim 19 and a pharmaceutically acceptable carrier, diluent or excipient.

21. A compound of the formula

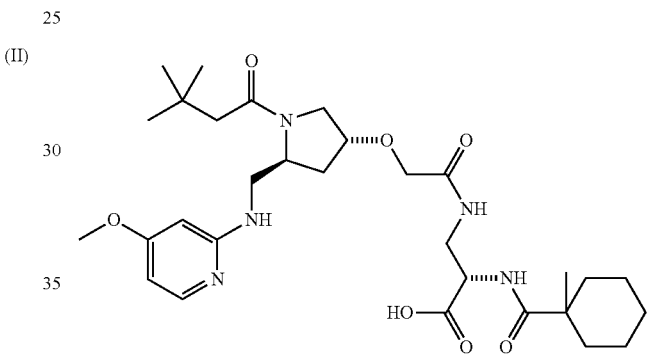

or a pharmaceutically acceptable salt thereof.

22. The compound according to claim 21, wherein the compound is compound 148: 3-(2-{1-(3,3-Dimethyl-butyryl)-5-[(4-methoxy-pyridin-2-ylamino)-methyl]-pyrrolidin-3-yloxy}-acetylamino)-2-[(1-methyl-cyclohexanecarbonyl)-amino]-propionic acid.

23. A pharmaceutical composition comprising a compound according to claim 21 or claim 22 and a pharmaceutically acceptable carrier, diluent or excipient.

* * * * *

UNITED STATES PATENT AND TRADEMARK OFFICE
CERTIFICATE OF CORRECTION

| | | |
|---|---|---|
| PATENT NO. | : 8,501,787 B2 | Page 1 of 1 |
| APPLICATION NO. | : 10/593801 | |
| DATED | : August 6, 2013 | |
| INVENTOR(S) | : Zahn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1677 days.

Signed and Sealed this
Seventeenth Day of February, 2015

Michelle K. Lee
*Deputy Director of the United States Patent and Trademark Office*